(12) United States Patent
Havenga et al.

(10) Patent No.: US 7,749,493 B2
(45) Date of Patent: *Jul. 6, 2010

(54) CHIMERIC ADENOVIRUSES

(75) Inventors: Menzo Havenga, Alphen Aan Den Rijn (NL); Ronald Vogels, Linschoten (NL); Abraham Bout, Moerkapelle (NL)

(73) Assignee: Crucell Holland B.V., Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 11/207,626

(22) Filed: Aug. 18, 2005

(65) Prior Publication Data

US 2006/0014276 A1    Jan. 19, 2006

Related U.S. Application Data

(63) Continuation of application No. 09/348,354, filed on Jul. 7, 1999, now abandoned.

(30) Foreign Application Priority Data

Jul. 8, 1998    (EP) .................................. 98202297

(51) Int. Cl.
| | |
|---|---|
| A61K 48/00 | (2006.01) |
| C12N 15/00 | (2006.01) |
| C12N 15/09 | (2006.01) |
| C12N 15/11 | (2006.01) |
| C12N 15/34 | (2006.01) |

(52) U.S. Cl. .................. 424/93.2; 435/320.1; 435/440; 435/69.1

(58) Field of Classification Search ........................ None
See application file for complete search history.

(56) References Cited

U.S. PATENT DOCUMENTS

| | | | |
|---|---|---|---|
| 4,487,829 A | 12/1984 | Sharp et al. | |
| 4,517,686 A | 5/1985 | Ruoslahti et al. | |
| 4,578,079 A | 3/1986 | Ruoslahti et al. | |
| 4,589,881 A | 5/1986 | Pierschbacher et al. | |
| 4,593,002 A | 6/1986 | Dulbecco | |
| 4,792,525 A | 12/1988 | Ruoslahti et al. | |
| 4,797,368 A | 1/1989 | Carter et al. | |
| 4,956,281 A | 9/1990 | Wallner et al. | |
| 5,024,939 A | 6/1991 | Gorman | |
| 5,096,815 A | 3/1992 | Ladner et al. | |
| 5,166,320 A | 11/1992 | Wu et al. | |
| 5,198,346 A | 3/1993 | Ladner et al. | |
| 5,204,445 A | 4/1993 | Plow et al. | |
| 5,223,394 A | 6/1993 | Wallner | |
| 5,223,409 A | 6/1993 | Ladner et al. | |
| 5,240,846 A | 8/1993 | Collins et al. | |
| 5,246,921 A | 9/1993 | Reddy et al. | |
| 5,332,567 A | 7/1994 | Goldenberg | |
| 5,349,053 A | 9/1994 | Landolfi | |
| 5,403,484 A | 4/1995 | Ladner et al. | |
| 5,436,146 A | 7/1995 | Shenk et al. | |
| 5,443,953 A | 8/1995 | Hansen et al. | |
| 5,474,935 A | 12/1995 | Chatterjee et al. | |
| 5,521,291 A | 5/1996 | Curiel et al. | |
| 5,534,423 A | 7/1996 | Plasson et al. | |
| 5,543,328 A | 8/1996 | Mcclelland et al. | |
| 5,547,932 A | 8/1996 | Curiel et al. | |
| 5,552,311 A | 9/1996 | Sorscher et al. | |
| 5,559,099 A | 9/1996 | Wickham et al. | |
| 5,571,698 A | 11/1996 | Ladner et al. | |
| 5,622,699 A | 4/1997 | Ruoslahti et al. | |
| 5,712,136 A | 1/1998 | Wickham et al. | |
| 5,731,190 A | 3/1998 | Wickham et al. | |
| 5,756,086 A | 5/1998 | Mcclelland et al. | |
| 5,770,442 A | 6/1998 | Wickham et al. | |
| 5,837,511 A | 11/1998 | Flack-Pedersen et al. | |
| 5,846,782 A | 12/1998 | Wickham et al. | |
| 5,849,561 A | 12/1998 | Falck-Pedersen | |
| 5,856,152 A | 1/1999 | Wilson et al. | |
| 5,871,727 A | 2/1999 | Curiel | |
| 5,871,982 A | 2/1999 | Wilson et al. | |

(Continued)

FOREIGN PATENT DOCUMENTS

EP    259212    8/1987

(Continued)

OTHER PUBLICATIONS

Abrahamsen et al., "Construction of an Adenovirus Type 7a E1A Vector," Journal of Virology, Nov. 1997, p. 8946-8951 vol. 71, No. 11.

(Continued)

*Primary Examiner*—Maria B Marvich
(74) *Attorney, Agent, or Firm*—TraskBritt

(57) ABSTRACT

The present invention provides methods and vector systems for the generation of chimeric recombinant adenoviruses. These hybrid adenoviruses contain a genome that is derived from different adenovirus serotypes. In particular, novel hybrid adenoviruses are disclosed with improved properties for gene therapy purposes. These properties include: a decreased sensitivity towards neutralizing antibodies, a modified host range, a change in the titer to which adenovirus can be grown, the ability to escape trapping in the liver upon in vivo systemic delivery, and absence or decreased infection of antigen presenting cells (APC) of the immune system, such as macrophages or dendritic cells. These chimeric adenoviruses thus represent improved tools for gene therapy and vaccination since they overcome the limitations observed with the currently used serotype subgroup C adenoviruses.

5 Claims, 16 Drawing Sheets

U.S. PATENT DOCUMENTS

| | | | |
|---|---|---|---|
| 5,877,011 A | 3/1999 | Armentano et al. | |
| 5,922,315 A | 7/1999 | Roy | |
| 5,994,128 A | 11/1999 | Fallaux et al. | |
| 6,033,908 A | 3/2000 | Bout et al. | |
| 6,057,155 A | 5/2000 | Wickham et al. | |
| 6,100,086 A | 8/2000 | Kaplan et al. | |
| 6,127,525 A * | 10/2000 | Crystal et al. | 530/388.22 |
| 6,287,857 B1 | 9/2001 | O'riordan et al. | |
| 6,306,652 B1 | 10/2001 | Fallaux et al. | |
| 6,486,133 B1 | 11/2002 | Herlyn et al. | |
| 6,492,169 B1 | 12/2002 | Vogels et al. | |
| 6,669,942 B2 | 12/2003 | Perricaudet et al. | |
| 6,803,234 B2 * | 10/2004 | Havenga et al. | 435/456 |
| 6,869,936 B1 * | 3/2005 | Vogels et al. | 514/44 R |
| 6,905,678 B2 * | 6/2005 | Havenga et al. | 424/93.2 |
| 7,238,528 B2 * | 7/2007 | Vogels et al. | 435/455 |
| 2004/0142473 A1 * | 7/2004 | Vogels et al. | 435/456 |

FOREIGN PATENT DOCUMENTS

| | | |
|---|---|---|
| EP | 1016726 | 12/1998 |
| EP | 99201545.3 | 5/1999 |
| EP | 1067188 | 7/1999 |
| EP | 1020529 | 11/1999 |
| EP | 0 978 566 A2 | 2/2000 |
| WO | WO 91/00360 | 1/1991 |
| WO | WO 91/05805 | 5/1991 |
| WO | WO 91/05871 | 5/1991 |
| WO | WO 92/02553 | 2/1992 |
| WO | WO 92/13081 | 8/1992 |
| WO | WO 93/03769 | 3/1993 |
| WO | WO 93/06223 | 4/1993 |
| WO | WO 93/07282 | 4/1993 |
| WO | WO 93/07283 | 4/1993 |
| WO | WO 94/08026 | 4/1994 |
| WO | WO 94/10323 | 5/1994 |
| WO | WO 94/11506 | 5/1994 |
| WO | WO 94/15644 | 7/1994 |
| WO | WO 94/17832 | 8/1994 |
| WO | WO 94/24299 | 10/1994 |
| WO | WO 94/26915 | 11/1994 |
| WO | WO 95/05201 | 2/1995 |
| WO | WO 95/06745 | 3/1995 |
| WO | WO 95/14785 | 6/1995 |
| WO | WO 95/16037 | 6/1995 |
| WO | WO 95/21259 | 8/1995 |
| WO | WO 95/26412 | 10/1995 |
| WO | WO 95/27071 | 10/1995 |
| WO | WO 95/31187 | 11/1995 |
| WO | WO 95/31566 | 11/1995 |
| WO | WO 96/00326 | 1/1996 |
| WO | WO 96/00790 | 1/1996 |
| WO | WO 96/07739 | 3/1996 |
| WO | WO 96/10087 | 4/1996 |
| WO | WO 96/12030 | 4/1996 |
| WO | WO 96/13597 | 5/1996 |
| WO | WO 96/13598 | 5/1996 |
| WO | WO 96/14837 | 5/1996 |
| WO | WO 96/17073 | 6/1996 |
| WO | WO 96/18740 | 6/1996 |
| WO | WO 96/24453 | 8/1996 |
| WO | WO 96/26281 * | 8/1996 |
| WO | WO 96/35798 | 11/1996 |
| WO | WO 97/00326 | 1/1997 |
| WO | WO 97/12986 | 4/1997 |
| WO | WO 97/20575 | 6/1997 |
| WO | WO 97/38723 | 10/1997 |
| WO | WO 98/07865 | 2/1998 |
| WO | WO 98/11221 | 3/1998 |
| WO | WO 98/13499 | 4/1998 |
| WO | WO 98/22609 | 5/1998 |
| WO | WO 98/32842 | 7/1998 |
| WO | WO 98/40509 | 9/1998 |
| WO | WO 98/49300 | 11/1998 |
| WO | WO 98/50053 A1 | 11/1998 |
| WO | WO 99/32647 | 7/1999 |
| WO | WO 99/47180 A1 | 9/1999 |
| WO | WO 99/55132 | 11/1999 |
| WO | WO 99/58646 | 11/1999 |
| WO | WO 00/03029 | 1/2000 |
| WO | WO 00/24730 A2 | 5/2000 |
| WO | WO 00/31285 | 6/2000 |
| WO | WO 00/52186 | 9/2000 |
| WO | WO 00/70071 A1 | 11/2000 |
| WO | WO 01/04334 | 1/2001 |
| WO | WO 01/90158 A1 | 11/2001 |
| WO | WO 02/24730 | 3/2002 |
| WO | WO 02/27006 | 4/2002 |

OTHER PUBLICATIONS

Albiges-Rizo et al., "Human Adenovirus Serotype 3 Fiber Protein," Journal of Biological Chemistry, 266(6), 3961-3967 (1991).

Anderson, Nature, "Human gene therapy," Apr. 1998, vol. 392, pp. 25-30.

Athappilly et al., "The Refined Crystal Structure of Hexon, the Major Coat Protein of Adenovirus Type 2, at 29 A Resolution," J. Mol. Biol. (1994) 242, 430-455.

Bai et al., "Mutations That Alter an Arg-Gly-Asp (RGD) Sequence in the Adenovirus Type 2 Penton Base Protein Abolish Its Cell-Rounding Activity and Delay Virus Reproduction in Flat Cells," Journal of Virology, 67(9), 5198-5205 (1993).

Bailey et al., "Phylogenetic Relationships among Adenovirus Serotypes," Virology, 205, 439-452 (1994).

Ball-Goodrich et al., "Parvoviral Target Cell Specificity: Acquisition of Fibrotropism by a Mutant of the Lymphotropic Strain of Minute Virus of Mice Involves Multiple Amino Acid Substitutions within the Capsid," Virology, 184, 175-186, (1991).

Basler et al., Sequence of the immunoregulatory early region 3 and flanking sequences of adenovirus type 35, 1996, Gene 170:249-254.

Basler et al., "Subgroup B Adenovirus Type 35 Early Region 3 mRNAs Differ from Those of the Subgroup C Adenoviruses," Virology 215,165-177 (1996).

Batra et al., "Receptor-mediated gene delivery employing lectinbinding specificity," Gene Therapy, 1, 255-260 (1994).

Berendsen, Herman J.C., A Glimpse of the Holy Grail, Science, 1998, vol. 282, pp. 642-643.

Boursnell et al., "In vitro construction of a recombinant adenovirus Ad2:Ad5," Gene, 13, 311-317 (1981).

Bridge et al., "Adenovirus Early Region 4 and Viral DNA Synthesis," Virology 193, 794-801 (1993).

Brody et al., "Adenovirus-Mediated in Vivo Gene Transfer," Annals New York Academy of Sciences pp. 90-100.

Caillet-Boudin et al., "Functional and Structural Effects of an Ala to Val Mutation in the Adenovirus Serotype 2 Fibre," J. Mol. Biol., 217, 477-486 (1991).

Chiu et al., Folding & Design, "Optimizing energy potentials for success in proteirtertiary structure prediction," May 1998, 3:223-228.

Chroboczek et al., "The Sequence of the Genome of Adenovirus Type 5 and Its Comparison with the Genome of Adenovirus Type 2," Virology, 186, 280-285 (1992).

Chroboczek et al., Adenovirus Fiber, Current Topics in Microbiology and Immunology 1995;199 (Pt 1) pp. 163-200.

Chu et al., "Cell targeting with retroviral vector particles containing antibodyenvelope fusion proteins," Gene Therapy, 1, 292-299 (1994).

Cotton et al., "Transferrin-polycation-mediated introduction of DNA into human leukemic cells: Stimulation by agents that affect the survival of transfected DNA or modulate transferring receptor levels," Pro. Natl. Acad. Sci. USA, 87, 4033-4037 (1990).

Cotton et al., "High-efficiency receptor-mediated delivery of small and large (48 kilobase gene constructs using the endosome-disruption activity of defective or chemically inactivatedadenovirus particles," Proc. Natl. Acad. Sci. USA, 89, 6094-6098 (1992).

Crawford-Miksza et al., "Adenovirus Serotype Evolution Is Driven by Illegitimate Recombination in the Hypervariable Regions of the Hexon Protein," Virology, 224, 357-367 (1996).

Crawford-Miksza et al., "Analysis of 15 Adenovirus Hexon Proteins Reveals the Location and Structure of Seven Hypervariable Regions Containing SerotypeSpecific Residues," Journal of Virology, Mar. 1996, p. 1836-1844.

Crompton et al., "Expression of a foreign epitope on the surface of the adenovirus hexon," J. Gen. Virol., 75(1), 131-139 (1994).

Crystal, Ronald G., "Transfer of Genes to Humans: Early Lessons and Obstacles to Success," Science, 270, 404-410 (1995).

Curiel et al., "High-Efficiency Gene Transfer Mediated by Adenovirus Coupled to DNABPolylysine Complexes," Human Gene Therapy, 3, 147-154 (1992).

Curiel et al., "Adenovirus enhancement of transferringpolylysine-mediated gene delivery," Proc. Natl. Acad. Sci. USA, 88, 8850-8854 (1991).

De Jong et al., "Adenovirus Isolates From Urine of Patients with Acquired Immunodeficiency Syndrome," The Lancet, Jun. 11, 1983 pp. 1293-1296.

De Jong et al., Adenoviruses from Human Immunodeficiency VirusInfected Individuals, Including Two Strains That Represent New Candidate Serotypes Ad50 and Ad51 of Species B1 and D, Respectively, Journal of Clinical Microbiology, Dec. 1999, p. 3940-45, vol. 37, No. 12, American Society for Microbiology.

Defer at al., "Human Adenovirus-Host Cell Interactions: Comparative Study with Members of Subgroups B and C," Journal of Virology, 64(8), 3661-3673 (1990).

Deonarain, "Ligand-targeted receptor-mediated vectors for gene delivery," (1998) Expert Opin. Ther. Pat. 8: 53-69.

Dijkema et al., "Transformation of Primary Rat Kidney Cells by DNA Fragments of Weakly Oncogenic Adenoviruses," Journal of Virology, Dec. 1979, p. 943-950.

Douglas J T et al.: "Strategies to accomplish targeted gene delivery to musclecells employing tropism-modified adenoviral vectors" Neuromuscular Disorders, Pergamon Press, GB, vol. 7, Jul. 1997, pp. 284-298, XP002079944 ISSN: 0960-8966.

Dupuit et al., "Regenerating Cells in Human Airway Surface Epithelium Represent Preferential Targets for Recombinant Adenovirus," Human Gene Therapy, 6, 1185-1193 (1995).

Eck et al., "Gene-Based Therapy," (1996) Goodman & Gillman's The Pharmacological Bais of Therapeutics, McGraw-Hill, New York, N.Y., pp. 77-101.

Etienne-Julan et al., "The efficiency of cell targeting by recombinant retroviruses depends on the nature of the receptor and the composition of the artificial cell-virus linker," Journal of General Virology, 73, 3251-3255 (1992).

Falgout et al., "Characterization of Adenovirus Particles Made by Deletion Mutants Lacking the Fiber Gene," Journal of Virology, 62(2), 622-625 (1988).

Flomenberg et al., "Molecular Epidemiology of Adenovirus Type 35 Infections in Immunocompromised Hosts," The Journal Of Infectious Diseases vol. 155, No. 6, Jun. 1987.

Flomenberg et al., "Sequence and genetic Organization of Adenovirus Type 35 Early Region 3," Journal of Virology, Nov. 1988, pp. 4431-4437.

Francki et al., "Classification and Nomenclature of Viruses," Fifth Report of the International Committee on Taxonomy of Viruses; Virology Division of the International Union of Microbiology Societies pp. 140-143.

Gahery-Segard et al., "Immune response torecombinant Capsid Proteins of Adenovirus in Humans: Antifiber and Anti Penton Base Antibodies Have a Synergistic Effect on Neutralizing Activity," Journal of Virology, Mar. 1998, pp. 2388-2397, vol. 72, No. 3.

Gall et al., "Construction and characterization of Hexon-Chimeric Adenoviruses: Specification of adenovirus serotype," 72(12) Journal of Virology 10260-64 (1998).

Gall et al., "Adenovirus Type 5 and 7 Capsid Chimera: Fiber Replacement Alters ReceptorTropism without Affecting Primary Immune Neutralization Epitopes," Journal Of Virology, Apr. 1996, p. 2116-2123.

George et al., "Gene therapy progress and prospects: adenoviral vectors," Gene Therapy (2003) 10, 1135-1141.

Gorecki, "Prospects and problems of gene therapy: an update," (2001) Expert Opin. Emerging Drugs 6(2): 187-98.

Greber et al., "Stepwise Dismantling of Adenovirus 2 during Entry into Cells," Cell, 75477-486 (1993).

Green et al., "Evidence for a repeating cross- sheet structure in the adenovirus fibre," EMBO Journal, 2(8), 1357-1365 (1983).

Grubb et al., Inefficientgene transfer by adenovirus vector to cystic fibrosis airway epithelia of mice and humans, Nature, 371, 802-806 (1994).

Gurunathan et al., American Association of Immunologists, "CD40 Ligand/Trimer DNA Enhances Bth Humoral and Cellular Immune Responses and Indicates Protective Immunity to Infectious and Tumor Challenge," 1998, 161:abstract only.

Han et al., "Ligand-directed retroviral targeting of human breast cancer cells,"Proc. Natl. Acad. Sci. USA, 92, 9747-9751 (1995).

He et al., "A simplified system for generating recombinant adenoviruses," Proc. Natl. Acad. Sci. USA vol. 95, pp. 2509-2514, Mar. 1998.

Henry et al., "Characterization of the Knob Domain of the Adenovirus Type 5 Fiber Protein Expressed in *Escherichia coli*," Journal of Virology, 68(8), 5239-5246 (1994).

Hidaka, Chisa, et al., "CAR-dependent and CAR-independent pathways of adenovirus vector-mediated gene transfer and expression in human fibroblasts," 103(4) The Journal of Clinical Investigation pp. 579-587 (Feb. 1999).

Hierholzer et al., "Adenoviruses from Patients with AIDS: A Plethora of Serotypes and A Description of Five New Serotypes of Subgenus D (Types 43-47)," The Journal Of Infectious Diseases vol. 158, No. 4 Oct. 1988.

Hong et al., "The Amino Terminus of the Adenovirus FiberProtein Encodes the Nuclear Localization Signal,"Virology, 185(2), 758-767 (1991).

Horvath et al., "Nonpermissivity of Human Peripheral Blood Lymphocytes to Adenovirus Type 2 Infection," Journal of Virology, 62(1), 341-345 (1988).

Huang et al., "Upregulation of Integrins alpha-v-beta-3 and alpha-v-beta-5 on Human Monocytes and TLymphocytes Facilitates Adenovirus-Mediated Gene Delivery," Journal of Virology, 69(4), 2257-2263 (1995).

Imler et al., "Novel complementation cell lines derived from human lung carcinoma A549 cells support the growth of E1-deleted adenovirus vectors," Gene Therapy, vol. 3: p. 75-84, 1996.

Jolly; viral vector systems for gene therapy, 1994, Cancer Gene Therapy, vol. 1, No. 1: pp. 51-64.

Kang et al., "Molecular Cloning And Physical Mapping of the DNA of Human Adenovirus Type 35," Acta Microbiologica Hungarica 36 (1), pp. 67-75 (1989).

Kang et al., "Relationship Of E1 And E3 Regions of Human Adenovirus 35 To Those Of Human Adenovirus Subgroups A, C And D," Acta Microbiologica Hungarica 36 (4), pp. 445-457 (1989).

Karayan et al., "Oligomerization of Recombinant Penton Base of Adenovirus Type 2 and Its Assembly with Fiber in Baculovirus-Infected Cells," Virology, 202, 782-795 (1994).

Kass-Eisler et al., "Quantitative determination of adenovirusmediated gene delivery to rat cardiac myocytes in vitro and in vivo," Proc. Natl. Acad. Sci. USA, 90, 11498-11502 (1993).

Kmiec, "Gene Therapy,"American Scientist, vol. 87, pp. 240, (1999).

Komoriya et al., The Minimal Essential Sequence for a Major Cell Typespecific Adhesion Site (CS1) within the Alternatively Spliced Type III Connecting Segment Domain of Fibronectin Is LeucineAspartic Acid-Valine,: Journal of Biological Chemistry, 266(23), 15075-15079 (1991).

Krasnykh et al.: "Generation Of Recombinant Adenovirus Vectors With Modified Fibers For Altering Viral Tropism" Journal Of Virology, The American Society For Microbiology, US, vol. 70, No. 10, Oct. 1, 1996, pp. 6839-6846, XP002067518 ISSN: 0022-538X.

Lattanzi, Laura, et al., "High Efficiency Myogenic Conversion of Human Fibroblasts by Adenoviral Vectemediated MyoD Gene Transfer," 101(10) J. Clin. Invest. 2119-28 (May 1998).

Lee et al., "The constitutive expression of the immunomodulatory gp 19k protein in E1, E3- adenoviral vectors strongly reduces the host cytotoxic T cell response against the vector," Gene Therapy (1995)2, 256262.

Levrero et al., "Defective and nondefective adenovirus vectors for expressing foreign genes in vitro and in vivo," Gene, 101 (1991) 195-202.

Li et al., "Genetic Relationship between Thirteen Genome Types of Adenovirusl 1, 34, and 35 with Different Tropisms," Intervirology 1991; 32:338-350.

Liu et al., Molecular Basis of the inflammatory response to adenovirus vectors. Gene Therapy (2003 10, 935-940.

Maraveyas et al., "Targeted Immunotherapy B An update with special emphasis on ovarian cancer," Acta Oncologica, 32(7/8), 741-746 (1993).

Mastrangeli et al., "Sero-Switch" Adenovirus-Mediated In Vivo Gene Transfer: Circumvention of Anti-Adenovirus Humoral Immune Defenses Against Repeat Adenovirus Vector Administration by Changing the Adenovirus Serotype, Human Gene Therapy, 7, 79-87 (1996).

Mathias et al., "Multiple Adenovirus Serotypes Use alpha-v Integrins for Infection," Journal of Virology, 68(10), 6811-6814 (1994).

Mautner et al., "Recombination in Adenovirus: DNA Sequence Analysis of Crossover Sites in Intertpic Recombinants," Virology, 131, 1-10 (1983).

Mautner et al., "Recombination in Adenovirus: Analysis of Crossover Sites in Intertypic Overlap Recombinants," Virology, 139, 43-52, (1984).

Merriam-Webster Dictionary (on line) retrieved from the internet<URL:htpp://www. mw.com/cgi-bin/dictionary, "derive," 2002.

Michael et al., "Addition of a short peptide ligand to the adenovirusfiber protein," Gene Therapy, 2, 660-668 (1995).

Michael et al., "Binding-incompetent Adenovirus Facilitates Molecular Conjugatemediated Gene Transfer by the Receptor-mediated Endocytosis Pathway," Journal of Biological Chemistry, 268(10), 68666869 (1993).

Miller et al., "Targeted vectors for gene therapy," FASEB Journal, 9, 190199 (1995).

Neda et al., "Chemical Modification of an Ecotropic Murine Leukemia Virus Results in Redirection of Its Target Cell Specificity," Journal of Biological Chemistry, 266(22), 1414314146 (1991).

Nemerow et al., "The Role of alpha-v Integrins in Adenovirus Infection," Biology of Vitronectins and their Receptors, 177-184 (1993).

Nemerow et al., "Adenovirus entry into host cells: a role for alphasub-v integrins," Trends In Cell Biology, 4, 52-55 (1994).

Ngo et al., The Protein Folding Problem and Tertiary Structure Prediction, "Computational Complexity, Protein Structure Prediction, and the Levinthal Paradox," 1994, Merz et al. (Editors), Birkhauser, Boston, MA, pp. 433 and 492-495.

Notice of Opposition to a European Patent, Patent No. 1054064, by Cell Genesys Inc., dated Jul. 5, 2005.

Novelli et al., "Deletion Analysis of Functional Domains in BaculovirusExpressed Adenovirus Type 2 Fiber," Virology, 185, 365-376 (1991).

Orkin et al., "Report and Recommendations of the Panel to Assess the NIH Investment in Research on Gene Therapy," (1995), <http://www.nih.gov/news/panelrep.html>.

Peteranderl et al., "Trimerization of the Heat Shock Transcription Factor by a TripleStranded -Helical Coiled-Coil," Biochemistry, 31, 12272-12276 (1992).

Prince, "Gene Transfer: A Review Of Methods and Applications," Pathology (1998), 30, pp. 335-347.

Pring-Åkerblom et al., "Sequence Characterization and Comparison of Human Adenovirus Subgenus B and E Hexons," Virology, 212, 232-36 (1995).

Ragot et al.,: "Efficient adenovirus-mediated transfer of a human minidystrophin gene to skeletal muscle of mdx mice" Nature, Macmillan Journals Ltd. London, GB, vol. 361, No. 6413, 1993, pages, XP00266251 ISSN: 0028-0836, abstract only.

Rea et al., "Highly efficient transduction of human monocytederived dendritic cells with subgroup B fiber-modified adenovirus vectors enhances transgene-encoded antigen presentation to cytotoxic T cells." Journal Of Immunology, (Apr. 15, 2000) 166 (8) 5236-44. ,—Apr. 15, 2001 XP002192775.

Robbins et al., "Viral Vectors for Gene Therapy," Pharmacol. Ther. vol. 80, No. 1, pp. 35-47, 1998.

Roberts et al., "Three-Dimensional Structure of the Adenovirus Major Coat Protein Hexon," Science, 232, pp. 1148-1151 (1986).

Roelvink et al., The Coxsackievirus-Adenovirus Receptor Protein Can Function as a Cellular Attachment Protein for Adenovirus Serotypes from Subgroups A, C, D, E, and F, Journal Of Virology, Oct. 1998, p. 7909-7915, vol. 72, No. 10.

Romano, "Gene Transfer in Experimental Medicine," Drug & News Perspectives, vol. 16, No. 5, 2003, 13 pages.

Rosenfeld et al., Adenovirus-Mediated Transfer of a recombinant alpha-1-Antitrypsin Gene to the Lung Epithelium in Vivo, Science, Apr. 19, 1991, pp. 431-434, vol. 252.

Roy et al., "Circumvention of Immunity to the Adenovirus major Coat Protein Hexon," Journal of Virology, Aug. 1998, pp. 6875-6879, vol. 72, No. 8.

Russell et al., "Retroviral vectors displaying functional antbody fragments," Nucleic Acids Research, 21(5), 1081-1085 (1993).

Russell, "Replicating Vectors for Gene Therapy of Cancer: Risks, Limitations and Prospects," European Journal of Cancer, vol. 30A, No. 8, pp. 1165-1171, (1994).

Sabourin et al., "The molecular regulation of myogenesis," (2000) Clin.' Genet. 57(1): 16-25.

Schnurr et al., "Two New Candidate Adenovirus Serotypes," Intervirology 1993, 36:79-83.

Schulick et al., "Established Immunity Precludes Adenovirusmediated Gene Transfer in Rat Carotid Arteries," The Journal of Clinical Investigation vol. 99, No. 2, Jan. 1997, 209-219.

Segerman et al.: "Adenovirus types 11p and 35p show high binding efficiencies for committed hematopoietic cell lines and are infective to these cell lines" Journal of Virology, The American Society for Microbiology, US, vlo. 74, No. 3, Feb. 2000, pp. 1457-1467, XP002161682 ISSN: 0022-538X.

Shayakhmetov et al., "Efficient Gene Transfer into Human CD34+ Cells by a Retargeted Adenovirus Vector," Joural Of Virology, Mar. 2000, p. 2567-2583.

Signäs et al., "Adenovirus 3 Fiber Polypeptide Gene: Implications for the Structure of the Fiber Protein," Journal of Virology, 53(2), 672-678 (1985).

Silver et al., "Interaction of Human Adenovirus Serotype 2 with Human Lymphoid Cells," Virology, 165, 377-387 (1988).

Stevenson et al., "Human Adenovirus Serotypes 3 and 5 Bind to Two Differen Cellular receptors via the Fiber Head Domain," Journal of Virology, May 1995, pp. 2850-2857, vol. 69, No. 5.

Stevenson et al.; Selective Targeting of Human Cells by a Chimeric Adenovirus Vector Containing a Modied Fiber Protein, 1997, Journal of Virology, vol. 71: 4782-4790.

Stewart et al., "Difference imaging of adenovirus: bridging the resolution gap between Xray crystallography and electron microscopy," EMBO Journal, 12(7), 2589-2599 (1993).

Stratford-Perricaudet LD et al.: "Widespread Long-Term Gene Transfer To Mouse Skeletal Muscles And Heart" Journal Of Clinical Investigation, New York, NY, US, vol. 90 No. 2, Aug. 1992, ISSN: 0021-9738, pp. 626-630.

Toogood et al., "The Adenovirus Type 40 Hexon: Sequence, Predicated Structure and Relationship to Other Adenovirus Hexons," J. gen. Virol (1989), 70, 3203-3214.

Valderrama-Leon et al., "Restriction Endonuclease Mapping of Adenovirus 35, a Type Isolated from Immunocompromised Hosts," Journal Of Virology, Nov. 1985, p. 647-650.

Verma et al., Nature, "Gene therapy-promises, problems and prospects," Sep. 1997, vol. 389, pp. 239-242.

Wadell, "Molecular Epidemiology of Human Adenoviruses," Microbiology and Immunology, vol. 110 pp. 191-220.

Wagner et al., "Coupling of adenovirus to transferringpolylysine/DNA complexes greatly enhances receptor-mediated gene delivery and expression of transfected genes," Proc. Natl. Acad. Sci. USA, 89, 6099-6103 (1992).

Watson et al., "An Antigenic Analysis of the Adenovirus Type 2 Fibre Polypeptide," Journal of Virology, 69, 525-535 (1988).

Wickham et al., "Integrins alpha-v-beta-3 and alpha-v-beta-5 Promote Adenovirus Internalization but Not Virus Attachment," Cell, 73, 309-319 (1993).

Wickham et al., "Integrin alpha-v-beta-5 Selectively Promotes Adenovirus Mediated Cell Membrane Permeabilization," Journal of Cell Biology, 127(1), 257-264 (1994).

Wickham et al.: "Increased In Vitro and In Vivo Gene Transfer by Adenovirus Vectors Containing Chimeric Fiber Proteins," Journal of Virology, Nov. 1997, p. 8221-8229.

Zhong et al.: "Recombinant Advenovirus Is An Efficient and NonPerturbing Genetic Vector For Human Dendritic Cells" European Journal Of Immunology, Weinheim, DE, vol. 29, No. 3, 1999, pages, abstract only, XP000938797 ISSN: 0014-2980.

Frank-Kamenetskii, Maxim D., Glossary, Unraveling DNA, 1993, p. 191, VCH Publishers, Inc.

Old, et al., Construction of genes for chimaeric proteins, Studies in Microbiology, Principles of Gene Manipulation an Introuction to Genetic Engineering, 1980, pp. 199-201, Blackwell Science Ltd.

Brody et al., "Adenovirus-Mediated in Vivo Gene Transfer," Annals New York Academy of Sciences, 1994, pp. 90-100.

Francki et al., "Classification and Nomenclature of Viruses," Fifth Report of the International Committee on Taxonomy of Viruses; Virology Division of the International Union of Microbiology Societies, 1991, pp. 140-143.

* cited by examiner 1.1: Serotype 8 fiber protein (SEQ ID NO:14)
SCSCPSAPTIFMLLQMKRARPSEDTFNPVYPYGYARNQNIPFLTPPFVSSNGFQ
NFPPGVLSLKLADPITINNQNVSLKVGGGLTQEETGKLTVNTEPPLHLTNNKLGI
ALDAPFDVIDNKLTLLAGHGLSUTKETSTLPGLVNTLVVLTGKGIGTDLSNNGGN
ICVRVGEGGGLSFNDNGDLVAFNKKEDKRTLWTTPDTSPNCRIDQDKDSKLTLV
LTKCGSQILANVSLIVVAGRYKIINNNTNPALKGFTIKLLFDKNGVLMESSNLGKS
YWNFRNQNSIMSTAYEKAIGFMPNLVAYPKPTTGSKKYARDIVYGNIYLGGKPH
QPVTIKTTFNQETGCEYSITFDFSWAKTYVNVEFETTSFTFSYIAQE 1.2: Serotype 9 fiber protein (SEQ ID NO:15)
SCSCPSAPTIFMLLQMKRARPSEDTFNPVYPYGYARNQNIPFLTPPFVSSDGFQ
NFPPGVLSLKLADPIAIVNGNVSLKVGGGLTQDGTGKLTVNADPPLQLTNNKL
GIALDAPFDVIDNKLTLLAGHGLSIITKETSTLPGLINTLVVLTGKGIGTESTDNGG
SVCVRVGEGGGLSFNNDGDLVAFNKKEDKRTLWTTPDTSPNCKIDQDKDSKLTL
VLTKCGSQILANVSLIVVAGKYKIINNNTQPALKGFTIKLLFDENGVLMESSNLGK
SYWNFRNENSIMSTAYEKAIGFMPNLVAYPKPTAGSKKYARDIVYGNIYLGGKP
DQPVTIKTTFNQETGCEYSITFDFSWAKTYVNVEFETTSFTFSYIAQE 1.3: Serotype 13 fiber protein (SEQ ID NO:16)
XXXXXSAPTIFMLLQMKRARSSXDTFNPVYPYGYARNQNIXFXTPPFVXSDGF
KNFPPGVLSLKLADPITIANGDVSLKVGGGLTLQEGSLTVDPKAPLQLANDKKLE
LVYDDPFEVSTNKLSLKVGHGLKVLDDKSAGGLKDLIGKLVVLTGKGIGIENLQ
NDDGSSRGVGINVRLGTDGGLSFDRKGELVAWNRKDDRRTLWTTPDPSPNCKA
ETEKDSKLTLVLTKCGSQILATVSIIVLKGKYEFVKKETEPKSFDVKLLFDSKGVL
LPTSNLSKEYWNYRSYDNNIGTPYENAVPFMPNLKAYPKPTKTASDKAENKISS
AKNKIVSNFYFGGQAYQPGTIIIKFNEEIDETCAYSITFNFGWGKVYDNPFPFDTTS
FTXSYIAQE 1.4: Serotype 14 fiber protein (SEQ ID NO:17)
HPFINPGFISPNGFTQSPDGVLTLKCLTPLTTTGGSLQLKVGGGLTVDDTDGTLQE
NIGATTPLVKTGHSIGLSLGAGLGTDENKLCTKLGEGLTFNSNNICIDDNINTLWT
GVNPTEANCQMMDSSESNDCKLILTLVKTGALVTAFVYVIGVSNNFNMLTTYRN
INFTAELFFDSAGNLLTSLSSLKTPLNHKSGQTWLLVPLLMLKVSCPAQLLILSIIIL
EKNKTTFTELVTTQLVITLLFPLTISVMLNQRAIRADTSYCIRITWSWNTGDAPEG
QTSATTLVTS 1.5: Serotype 20 fiber protein (SEQ ID NO:18)
IQNIPFLTPPFVSSDGLQNFPPGVLSLKLADPIAIVNGNVSLKVGGGITVEQDSGQL
IANPKAPLQVANDKLELSYAYPFETSANKLSLKVGQGLKVLDEKDSGGLQNLLG
KLVVLTGKGIGVEELKNPDNTRGVGINVRLGKDGGLSFNKNGELVAWNKHND
TGTLWTTPDPSPNCKIEEVKDSKLTLVLTKCGSQILATMAFQVVKGTYENISKNT
AKNSFSIKLLFDDNGKLLEGSSLDKDYWNFRSDDSIIPNQYDNAVPFMPNLKAYP
KPSTVLPSTDKNSNGKNTIVSNLYLEGKAYQPVAVTITFNKEIGCTYSITFDFGWA
KTYDVPIPFDSSSFT

FIG. 7

1.6: Serotype 23 fiber protein (SEQ ID NO:19)
QNIPFLTPPFVSSDGFQNFPPGVLSLKLADPIAITNGDVSLKVGGGLTVEQDSGNL
KVNTKAPLQVAADKQLEIALADPFEVSKGRLGIKAGHGLKVIDNSISGLEGLVGT
LVVLTGHGIGTENLLNNDGSSRGVGINVRLGKDGGLSFDKKGDLVAWNKKYDT
RTLWTTPDPSPNCKVIEAKDSKLTLVLTKCGSQILANMSLLILKGTYEYISNAIAN
KSFTIKLLFNDKGVLMDGSSLDKDYWNYKSDDSVMSKAYENAVPFMPNLKAYP
NPTTSTTNPSTDKKSNGKNAIVSNVYLEGRAYQPVAITITFNKETGCTYSMTFDF
GWSKVYNDPIPFDTSSLT 1.7: Serotype 24 fiber protein (SEQ ID NO:20)
SCSCPSAPTIFMLLQMKRARPSEDTFNPVYPYGYARNQNIPFLTPPFVSSDGFQ
NFPPGVLSLKLADPIAITNGDVSLKVGGGLTVEKDSGNLKVNPKAPLQVTTDKQL
EIALAYPFEVSNGKLGIKAGHGLKVIDKIAGLEGLAGTLVVLTGKGIGTENLENS
DGSSRGVGINVRLAKDGGLSFDKKGDLVAWNKHDDRRTLWTTPDPSPNCTIDQ
ERDSKLTLVLTKCGSQILANVSLLVVKGKFSNINNNTNPTDKKITVKLLFNEKGV
LMDSSTLKKEYWNYRNDNSTVSQAYDNAVPFMPNIKAYPKPTTDTSAKPEDKK
SAAKRYIVSNVYIGGLPDKTVVITIKFNAETECAYSITFEFTWAKTFEDVQFDSSSF
TFSYIAQE 1.8: Serotype 25 fiber protein (SEQ ID NO:21)
SCSCPSAPTIFMLLQMKRARPSEDTFNPVYPYGYARNQNIPFLTPPFVSSDGFQ
NFPPGVLSLKLADPITISNGDVSLKVGGGLTVEQDSGNLSVNPKAPLQVGTDKKL
ELALAPPFNVKDNKLDLLVGDGLKVIDKSISXLPGLLNYLVVLTGKGIGNEELKN
DDGSNKGVGLCVRIGEGGGLTFDDKGYLVAWNKKHDIRTLWTTLDPSPNCRID
VDKDSKLTLVLTKCGSQILANVSLLVVKGRFQNLNYKTNPNLPKTFTIKLLFDEN
GILKDSSNLDKNYWNYRNGNSILAEQYKNAVGFMPNLAAYPKSTTTQSKLYAR
NTIFGNIYLDSQAYNPVVIKITFNQEADSAYSITLNYSWGKDYENIPFDS 1.9: Serotype 27 fiber protein (SEQ ID NO:22)
IPFLTPPFVSSDGFKNFPPGVLSLKLADPITITNGDVSLKVGGGLVVEKESGKLSV
DPKTPLQVASDNKLELSYNAPFKVENDKLSLDVGHGLKVIGNEVSSLPGLINKLV
VLTGKGIGTEELKEQNSDKIIGVGINVRARGGLSFDNDGYLVAWNPKYDTRTLW
TTPDTSPNCKMLTKKDSKLTLTLTKCGSQILGNVSLLAVSGKYLNMTKDETGVKI
ILLFDRNGVLMQESSLDKEYWNYRNDNNVIGTPYENAVGFMPNLVAYPKPTSA
DAKNYSRSKIISNVYLKGLIYQPVIIIASFNQETTNGCVYSISFDFTCSKDYTGQQF
DVTSF 1.10: Serotype 28 fiber protein (SEQ ID NO:23)
SCSCPSAPTIFMLLQMKRARPSEDTFNPVYPYGYARNQNIPFLTPPFVSSDGFQ
NFPPGVLSLKLADPITIANGDVSLKLGGGLTVEKESGNLTVNPKAPLQVASGQLE
LAYYSPFDVKNNMLTLKAGHGLAVVTKDNTDLQPLMGTLVVLTGKGIGTGTSA
HGGTIDVRIGKNGSLAFDKNGDLVAWDKENDRRTLWTTPDTSPNCKMSEVKDS
KLTLILTKCGSQILGSVSLLAVKGEYQNMTASTNKNVKITLLFDANGVLLEGSSL
DKEYWNFRNNDSTVSGKYENAVPFMPNITAYKPVNSKSYARSHIFGNVYIDAKP
YNPVVIKISFNQETQNNCVYSISFDYTCSKEYTGMQFDVTSFTFSYIAQE

FIG. 7 (continued)

1.11: Serotype 29 fiber protein (SEQ ID NO:24)
QNIPFLTPPFVSSDGFKNFPPGVLSLKLADPIAITNGDVSLKVGGGLTVEQDSGNL
SVNPKAPLQVGTDKKLELALAPPFDVRDNKLAILVGDGLKVIDRSISDLPGLLNY
LVVLTGKGIGNEELKNDDGSNKGVGLCVRIGEGGGLTFDDKGYLVAWNNKHDI
RTLWTTLDPSPNCKIDIEKDSKLTLVLTKCGSQILANVSLIIVNGKFKILNNKTDPS
LPKSFNIKLLFDQNGVLLENSNIEKQYLNFRSGDSILPEPYKNAIGFMPNLLAYAK
ATTDQSKIYARNTTYGNTYLDNQPYNPVVIKITFNNEADSAYSITFNYSWTKDYD
NIPFDSTSFTS 1.12: Serotype 30 fiber protein (SEQ ID NO:25)
SCSCPSAPTIFMLLQMKRARPSXDTFNPVYPYGYARNQNIPFXTPPFVXSDGFK
NFPPGVLSLKLADPIAITNGDVSLKVGGGLTVEQDSGNLSVNXKAPLQVGTDKK
LELALAPPFDVRDNKLAILVGDGLKVIDRSISDLPGLLNYLVVXTGKGIGNEELK
NDDGSNKGVGLCVRIGEGGGLTXDDKGYLVAWNNKHDIRTLWTTLDPSPNCKI
DIEKDSKLTLVLTKCGSQILANVSLIIVNGKFKILNNKTDPSLPKSFNIKLLFDQNG
VLLENSNIEKQYLNFRSGDSILPEPYKNAIGFMPNLLAYAKATTDQSKIYARNTIY
GNIYLDNQPYNPVVIKITFNNEADSAYSITFNYSWTKDYDNIPFDSTSFTFSYIAQE 1.13: Serotype 32 fiber protein (SEQ ID NO:26)
SCSCPSAPTIFMLLQMKRARPSEDTFNPVYPYGYARNQNIPFLTPPFVSSDGFQ
NFPPGVLSLKLADPITIANGNVSLKVGGGLTLEQDSGKLIVNPKAPLQVANDKLE
LSYADPFETSANKLSLKVGHGLKVLDEKNAGGLKDLIGTLVVLTGKGIGVEELK
NADNTNRGVGINVRLGKDGGLSFDKKGDLVAWNKHDDRRTLWTTPDPSPNCTI
DEERDSKLTLVLTKCGSQILANVSLLVVKGKFSNINNNTNPTDKKITVKLLFNEK
GVLMDSSSLKKEYWNYRNDNSTVSQAYDNAVPFMPNIKAYPKPTTDTSAKPED
KKSAAKRYIVSNVYIGGLPDKTVVITIKLNAETESAYSMTFEFTWAKTFENLQFD
SSSFTFSYIAQE 1.14: Serotype 33 fiber protein (SEQ ID NO:27)
SCSCPSAPTIFMLLQMKRARPSEDTFNPVYPYGYARNQNIPFLTPPFVSSDGFK
NFPPGVLSLKLADPITITNGDVSLKVGGGLTLQEGSLTVNPKAPLQLANDKKLEL
VYDDPFEVSTNKLSLKVGHGLKVLDDKSAGGLQDLIGKLVVLTGKGIGIENLQN
DDGSSRGVGINVRLGTDGGLSFDRKGELVAWNRKDDRRTLWTTPDPSPNCKAE
TEKDSKLTLVLTKCGSQILATVSIIVLKGKYEFVKKETEPKSFDVKLLFDSKGVLL
PTSNLSKEYWNYRSYDNNIGTPYENAVPFMPNLKAYPKPTKTASDKAENKISSA
KNKIVSNFYFGGQAYQPGTIIIKFNEEIDETCAYSITFNFGWGKVYDNPFPFDTTSF
TFSYIAQE 1.15: Serotype 34 fiber protein (SEQ ID NO:28)
SCSCPSAPTIFMLLQMKRARPSEDTFNPVYPYEDESTSQHPFINPGFISPNGFTQ
SPDGVLTLKCLTPLTTGGSLQLKVGGGLTVDDTGTLQKNIRATTPITKNNHSV
ELTIGNGLETQHNKLCAKLGNGLKFNNGDICIKDSINTLWTGINPPPNCQIVENTN
TNDGKLTLVLVKNGGLVNGYVSLVGVSDTVNQMFTQKTANIQLRLYFDSSGNL
LTDESDLKIPLKNKSSTATSETVASSKAFMPSTTAYPFNTTTRDSENYIHGICYYM
TSYDRSLFPLNISIMLNSRMISSNVAYAIQFEWNLNASESPEKQHMTLTTSPFFFSY
IIEDDN

FIG. 7 (continued)

1.16: Serotype 35 fiber protein (SEQ ID NO:29)
SCSCPSAPTIFMLLQMKRARPSEDTFNPVYPYEDESTSQHPFINPGFISPNGFTQ
SPDGVLTLKCLTPLTTTGGSLQLKVGGGLTVDDTGTLQENIRATAPITKNNHSV
ELSIGNGLETQNNKLCAKLGNGLKFNNGDICIKDSINTLWTGINPPPNCQIVENTN
TNDGKLTLVLVKNGGLVNGYVSLVGVSDTVNQMFTQKTANIQLRLYFDSSGNL
LTEESDLKIPLKNKSSTATSETVASSKAFMPSTTAYPFNTTTRDSENYIHGICYYM
TSYDRSLFPLNISIMLNSRMISSNVAYAIQFEWNLNASESPESNIMTLTTSPFFFSYI
TEDDN 1.17: Serotype 36 fiber protein (SEQ ID NO:30)
SCSCPSAPTIFMLLQMKRARPSEDTFNPVYPYGYARNQNIPFLTPPFVSSDGFK
NFPPGVLSLKLADPIAIVNGDVSLKVGGGLTVEQDSGKLKVNPKIPLQVVNDQLE
LATDKPFKIENNKLALDVGHGLKVIDKTISDLQGLVGKLVVLTGVGIGTETLKDK
NDKVIGSAVNVRLGKDGGLDFNKKGDLVAWNRYDDRRTLWTTPDPSPNCKVS
EAKDSKLTLVLTKCGSQILASVALLIVKGKYQTISESTIPKDQRNFSVKLMFDEKG
KLLDKSSLDKEYWNFRSNDSVVGTAYDNAVPFMPNLKAYPKNTTTSSTNPDDKI
SAGKKNIVSNVYLEGRVYQPVALTVKFNSENDCAYSITFDFVWSKTYESPVAFD
SSSFTFSYIAQE 1.18: Serotype 37 fiber protein (SEQ ID NO:31)
SCSCPSAPTIFMLLQMKRARPSEDTFNPVYPYGYARNQNIPFLTPPFVSSDGFK
NFPPGVLSLKLADPITITNGDVSLKVGGGLTLQDGSLTVNPKAPLQVNTDKKLEL
AYDNPFESSANKLSLKVGHGLKVLDEKSAAGLKDLIGKLVVLTGKGIGTENLEN
TDGSSRGIGINVRAREGLTFDNDGYLVAWNPKYDLRTLWTTPDTSPNCTIAQDK
DSKLTLVLTKCGSQILANVSLIVVAGKYHIINNKTNPKIKSFTIKLLFNKNGVLLD
NSNLGKAYWNFRSGNSNVSTAYEKAIGFMPNLVAVSKPSNSKKYARDIVYGNIY
LGGKPDQPGVIKTTFNQETGCEYSITFNFSWSKTYENVEFETTSFTFSYIAQE 1.19: Serotype 38 fiber protein (SEQ ID NO:32)
SCSCPSAPTIFMLLQMKRARPSEDTFNPVYPYGYARNQNIPFXTPPFVXSDGFQ
NFPPGVLSLKLADPITIANGNVSLKVGGGLTLEQDSGKLIVNXKAPLQVANDKLE
LSYADPFETSANKLSLKVGHGLKVLDEKNAGGLKDLIGTLVVLTGKGIGVEELK
NADNTNRGVGINVRLGKDGGLSFDKKGDXVAWNKHDDRRTLWTTPDPSPNCTI
DEERDSKLTLVLTKCGSQILANVSLLVVKGKFSNINNNTNPTDKKITVKLLFNEK
GVLMDSSSLKKEYWNYRNDNSTVSQAYDNAVPFMPNIKAYPKPTTDTSAKPED
KKSAAKRYIVSNVYIGGLPDKTVVITIKLNAETESAYSMTFEFTWAKTFENLQFD
SSSFTFSYIAQE 1.20: Serotype 39 fiber protein (SEQ ID NO:33)
IRISPSSLPPLSPPMDSKTSPLGCYHSNWLTQSPSPMGMSHSRWEGGSPWQEGTG
DLKVNAKSPLQVATNKQLEIALAKPFEEKDGKLALKIGHGLAVVDENHTHLQSL
IGTLVILTGKGIGTGRAESGGTIDVRLGSGGGLSFDKDGNLVAWNKDDDRRTLW
TTPDPSPNCKIDQDKDSKLTFVLTKCGSQILANMSLLVVKGKFSMINNKVNGTD
DYKKFTIKLLFDEKGVLLKDSSLDKEYWNYRSNNNNVGSAYEEAVGFMPSTTA
YPKPPTPPTNPTTPLEKSQAKNKYVSNVYLGGQAGNPVATTVSFNKETGCTYSIT
FDFAWNKTYENVQC 1.21: Serotype 42 fiber protein (SEQ ID NO:34)
SCSCPSAPTIFMLLQMKRARPSEDTFNPVYPYGYARNQNIPFLTPPFVSSDGFK
NFPPGVLSLKLANPIAITNGDVSLKVGGGLTQDGTGKLTIDTKTPLQVANNKLE
LAFDAPLYEKNGKLALKTGHGLAVLTKDIGIPELIGSLVILTGKGIGTGTVAGGGT
IDVRLGDDGGLSFDKKGDLVAWNKKNDRRTLWTTPDPSPNCRVSEDKDSKLTLI
LTKCGSQILASFSLLVVXGTYTTVDKNTTNKQFSIKLLFDANGKLKSESNLSGYW
NYRSDNSVVSTPYDNAVPFMPNTTAYPKIINSTTDPENKKSSAKKTIVGNVYLEG
NAGQPVAVAISFNKETTADYSITFDFAWSKAYETPVPFDTSSMTFSYIAQE 1.22: Serotype 43 fiber protein (SEQ ID NO:35)
NIPXLTPPFVSSDGFKNFPPGVLSLKLADPITITNGDVSLKVGGGLTVEKESGNLT
VNPKAPLQVAKGQLELAYDSPFDVKNNMLTLKAGHGLAVVTKDNTDLQPLMG
TLVVLTGKGIGTGTSAHGGTIDVRIGKNGSLAFDKGDLVAWDKENDRRTLWT
TPDTSPNCKMSEAKDSKLTLILTKCGSQILGSVSLLAVKGEYQNMTANTKKNVKI
TLLFDANGVLLAGSSXXKEYWNFRSNDSTVSGNYENAVQFMPNITAYKPTNSKS
YARSVIFGNVYIDAKPYNPVVIKISFNQETQNNCVYSISFDYTLSKDYPNMQFDV
TLS 1.23: Serotype 44 fiber protein (SEQ ID NO:36)
NIPFLTPPFVSSDGFQNFPPGVLSLKLADPITITNGNVSLKVGGGLTLQEGTGDLK
VNAKSPLQVATNKQLEIALAKPFEEKDGKLALKIGHGLAVVDENHTHLQSLIGTL
VILTGKGIGTGSAESGGTIDVRLGSGGGLSFDKDGNLVAWNKDDDRRTLWTTPD
PSPNCKIDQKDSKLTFVLTKCGSQILANMSLLVVKGKFSMINNKVNGTDDYKK
FTIKLLFDEKGVLLKDSSLDKEYWNYRSNNNNVGSAYEEAVGFMPSTTAYPKPP
TPPTNPTTPLEKSQAKNKYVSNVYLGGQAGNPVATTVSFNKETGCTYSITFDFA
WNKTYENVQFDSSF 1.24: Serotype 45 fiber protein (SEQ ID NO:37)
NIPFLTPPFVSSDGFQNFPPGVLSLKLADPIAITNGDVSLKVGGGLTVEKDSGNLK
VNPKAPLQVTTDKQLEIALAYPFEVSNGKLGIKAGHGLKVIDKIAGLEGLAGTLV
VLTGKGIGTENLENSDGSSRGVGINVRLAKDGVLAFDKKGDLVAWNKHDDRRT
LWTTPDPSPNCTIDQERDSKLTLVLTKCGSQILANVSLLVVKGKFSNINNNANPT
DKKITVKLLFNEKGVLMDSSTLKKEYWNYRNDNSTVSQAYDNAVPFMPNIKAY
PKPSTDTSAKPEDKKSAAKRYIVSNVYIGGLPDKTVVITIKFNAETECAYSITFEFT
WAKTFEDVQCDSSSFT 1.25: Serotype 46 fiber protein (SEQ ID NO:38)
NIPFLTPPFVSSDGFKNFPPGVLSLKLADPIAIVNGDVSLKVGGGLTLQEGNLTVD
AKAPLQVANDNKLELSYADPFEVKDTKLQLKVGHGLKVIDEKTSSGLQSLIGNL
VVLTGKGIGTQELKDKDDETKNIGVGINVRIGKNESLAFDKDGNLVAWDNENDR
RTLWTTPDTSSKFVKISTEKDSKLTLVLTKCGSQILASVSLLAVAGSYLNMTAST
QKSIKVSLMFDSKGLLMTTSSIDKGYWNYRNKNSVVGTAYENAIPFMPNLVAYP
RPNTPDSKIYARSKIVGNVYLAGLAYQPIVITVSFNQEKDASCAYSITFEFAWNKD
YVGQFDTTSFT

FIG. 7 (continued)

1.26: Serotype 47 fiber protein (SEQ ID NO:39)
SCPSAPTIFMLLQMKRARPSEDTFNPVYPYGYARNQNIPFLTPPFVSSDGFKNF
PPGVLSLKLADPITITNGDVSLKVGGGLTLQEGTGNLTVNAKAPLQVADDKKLE
LSYDNPFEVSANKLSLKVGHGLKVLDEKNSGGLQELIGKLVILTGKGIGVEELKN
ADNTNRGVGINVRLGKDGGLSFDKKGELVAWNKHNDTRTLWTTPDPSPNCKIE
QDKDSKLTLVLTKCGSQILATMAFQVVKGTYENISKNTAKKSFSIKLLFDDNGKL
LEGSSLDKDYWNFRNDDSIMPNQYDNAVPFMPNLKAYPNPKTSTVLPSTDKKSN
GKNTIVSNLYLEGKAYQPVAVTITFNKETGCTYSITFEFGWAKTYDVPIPFDSSSF
TFSYIAQE 1.27: Serotype 48 fiber protein (SEQ ID NO:40)
SDIPFLTPPFVSSDGFQNFPPGVLSLKLADPITITNGNVSLKVGGGLTLQEGTGDLK
VNAKSPLQVATNKQLEIALAKPFEEKDGKLALKIGHELAVVDENLTHLQSLIGTL
VILTGKGIGTGRAESGGTIDVRLGSGGGLSFDKDGNLVAWNKDDDRRTLWTTPD
PSPNCKIDQDKDSKLTFVLTKCGSQILANMSLLVVKGKFSMINNKVNGTDDYKK
FTIKLLFDEKGVLLKDSSLDKEYWNYRSNNNNVGSAYEEAVGFMPSTTAYPKPP
TPPTNPTTPLEKSQAKNKYVSNVYLGGQAGNPVATTVSFNKETGCTYSITFDFA
WNKTYKMAFIPRFNF 1.28: Serotype 49 fiber protein (SEQ ID NO:41)
SCSCPSAPTIFMLLQMKRARPSEDTFNPVYPYGYARNQNIPFLTPPFVSSDGFQ
NFPPGVLSLKLADPIAITNGNVSLKVGGGLTVEQDSGNLKVNPKAPLQVATDNQ
LEISLADPFEVKNKKLSLKVGHGLKVIDENISTLQGLLGNLVVLTGMGIGTEELK
KDDKIVGSAVNVRLGQDGGLTFDKKGDLVAWNKENDRRTLWTTPDPSPNCKVS
EEKDSKLTLVLTKCGSQILASVSLLVVKGKFANINNKTNPGEDYKXFSVKLLFDA
NGKLLTGSSLDGNYWNYKNKDSVIGSPYENAVPFMPNSTAYPKIINNGTANPED
KKSAAKKTIVTNVYLGGDAAKPVATTISFNKETESNCVYSITFDFAWNKTYKNV
PFDSSSLTFSYIAQE 1.29: Serotype 52 fiber protein (SEQ ID NO:42)
SCSCPSAPTIFMLLQMKRARPSEDTFNPVYPYEDESTSQHPFINPGFISPNGFTQ
SPDGVLTLNCLTPLTTTGGPLQLKVGGGLIVDDTDGTLQENIRVTAPITKNNHSV
ELSIGNGLETQNNKLCAKLGNGLKFNNGDICIKDSINTLWTGIKPPPNCQIVENTD
TNDGKLTLVLVKNGGLVNGYVSLGVSDTVNQMFTQKSATIQLRLYFDSSGNLL
TDESNLKIPLKNKSSTATSEAATSSKAFMPSTTAYPFNTTTRDSENYIHGICYYMT
SYDRSLVPLNISIMLNSRTISSNVAYAIQFEWNLNAKESPESNIATLTTSPFFFSYIIE
DTTKCISLCYVSTCLFFN

FIG. 7 (continued)

1: ΔHex1: 5'- CCT GGT GCT GCC AAC AGC- 3' (SEQ. ID. NO. 65)

2: ΔHex2: 5'- CC GGATCC CAATTG GGA AAG CGG GCG CGC G- 3' (SEQ. ID. NO. 86)

3: ΔHex3: 5'- CC GGATCC TGATCA AGA AGC AAG CAA CAT CAA CAA C- 3' (SEQ. ID. NO. 87)

4: ΔHex4: 5'- GAG AAG GGC ATG GAG GCT G- 3' (SEQ. ID. NO. 68)

1.1: Serotype 34 hexon protein (SEQ ID NO:43)
LSRRAPGFPLVKMATPSMLPQWAYMHIAGQDASEYLSPGLVQFARATDTYFNL
GNKFRNPTVAPTHDVTTDRSQRLMLRFVPVDREDNTYSYKVRYTLAVGDNRVL
DMASTFFDIRGVLDRGPSFKPYSGTAYNSLAPKGAPNASQWLDKGVTSTGLVDD
GNTDDGEEAKKATYTFGNAPVKAEAEITKDGLPVGLEVSTEGPKPIYADKLYQP
EPQVGDETWTDLDGKTEEYGGRVLKPETKMKPCYGSFAKPTNIKGGQAKVKPK
EDDGTNNIEYDIDMNFFDLRSQRSELKPKIVMYAENVDLECPDTHVVYKPGVSD
ASSETNLGQQSMPNRPNYIGFRDNFIGLMYYNSTGNMGVLAGQASQLNAVVDL
QDRNTELSYQLLDSLGDRTRYFSMWNQAVDSYDPDVRVIENHGVEDELPNYCF
PLDGVGPRTDSYKEIKPNGDQSTWTNVDPTGSSELAKGNPFAMEINLQANLWRS
FLYSNVALYLPDSYKYTPSNVTLPENKNTYDYMNGRVVPPSLVDTYVNIGARWS
LDAMDNVNPFNHHRNAGLRYRSMLLGNGRYVPFHIQVPQKFFAVKNLLLLPGS
YTYEWNFRKDVNMVLQSSLGNDLRVDGASISFTSINLYATFFPMAHNTASTLEA
MLRNDTNDQSFNDYLSAANMLYPIPANATNIPISIPSRNWAAFRGWSFTRLKTKE
TPSLGSGFDPYFVYSGSIPLDGTFYLNHTFKKVSIMFDSSVSWPGNDRLLSPNEFEI
KRTVDGEGYNVAQCNMTDWFLVQMLANYNIGYQGFYIPEGYKDRMYSFFRNF
QPMSRQVVDEVNYKDFKAVIPYQHNNSGFVGYMAPTMRQGQPYPANYPYPLIG
TTAVNSVTQKKFLCDRTMWRIPFSSNFMSMGALTDLGQNMLYANSAHALDMTF
EVDPMDEPTLLYLLFEVFDVVRVQPHRGIIEAVYLRTPFSAGNATT 1.2: Serotype 35 hexon protein (SEQ ID NO:44)
LSRRAPGFPLVKMATPSMLPQWAYMHIAGQDASEYLSPGLVQFARATDTYFNL
GNKFRNPTVAPTHDVTTDRSQRLMLRFVPVDREDNTYSYKVRYTLAVGDNRVL
DMASTFFDIRGVLDRGPSFKPYSGTAYNSLAPKGAPNASQWLDKGVTSTGLVDD
GNTDDGEEAKKATYTFGNAPVKAEAEITKDGLPVGLEVSTEGPKPIYADKLYQP
EPQVGDTWTDLDGKTEEYGGRVLKPETKMKPCYGSFAKPTNIKGGQAKVKPKE
DDGTNNIYDIDMNFFDLRSQRSELKPKIVMYAENVDLECPDTHVVYKPGVSDAS
SETNLGQQMPNRPNYIGFRDNFIGLMYYNSTGNMGVLAGQASQLNAVVDLQDR
NTELSYQLLLSLGDRTRYFSMWNQAVDSYDPDVRVIENHGVEDELPNYCFPLDG
VGPRTDSYKEIPNGDQSTWTNVDPTGSSELAKGNPFAMEINLQANLWRSFLYSN
VALYLPDSYKYTSNVTLPENKNTYDYMNGRVVPPSLVDTYVNIGARWSLDAMD
NVNPFNHHRNAGRYRSMLLGNGRYVPFHIQVPQKFFAVKNLLLLPGSYTYEWN
FRKDVNMVLQSSLDLRVDGASISFTSINLYATFFPMAHNTASTLEAMLRNDTND
QSFNDYLSAANMLYPIANATNIPISIPSRNWAAFRGWSFTRLKTKETPSLGSGFDP
YFVYSGSIPYLDGTFYLHTFKKVSIMFDSSVSWPGNDRLLSPNEFEIKRTVDGEGY
NVAQCNMTKDWFLVQLANYNIGYQGFYIPEGYKDRMYSFFRNFQPMSRQVVDE
VNYKDFKAVAIPYQHNNGFVGYMAPTMRQGQPYPANYPYPLIGTTAVNSVTQK
KFLCDRTMWRIPFSSNFMSALTDLGQNMLYANSAHALDMTFEVDPMDEPTLLY
LLFEVFDVVRVHQPHRGIIEAVLRTPFSAGNATT 1.3: Serotype 36 hexon protein (SEQ ID NO:45)
LSRRAPGFPLVKMATPSMLPQWAYMHIAGQDASEYLSPGLVQFARATDTYFNL
GNKFRNPTVAPTHDVTTDRSQRLMLRFVPVDREDNTYSYKVRYTLAVGDNRVL
DMASTFFDIRGVLDRGPSFKPYSGTAYNSLAPKGAPNASQWLDKGVTSTGLVDD
GNTDDGEEAKKATYTFGNAPVKAEAEITKDGLPVGLEVSTEGPKPIYADKLYQP
EPQVGDTWTDLDGKTEEYGGRVLKPETKMKPCYGSFAKPTNIKGGQAKVKPKE
DDGTNNIYDIDMNFFDLRSQRSELKPKIVMYAENVDLECPDTHVVYKPGVSDAS

FIG. 10

SETNLGQQSMPNRPNYIGFRDNFIGLMYYNSTGNMGVLAGQASQLNAVVDLQD
RNTELSYQLLDSLGDRTRYFSMWNQAVDSYDPDVRVIENHGVEDELPNYCFPLD
GVGPRTDSYKIKPNGDQSTWTNVDPTGSSELAKGNPFAMEINLQANLWRSFLYS
NVALYLPDSYKYTPSNVTLPENKNTYDYMNGRVVPPSLVDTYVNIGARWSLDA
MDNVNPFNHHRAGLRYRSMLLGNGRYVPFHIQVPQKFFAVKNLLLLPGSYTYE
WNFRKDVNMVLQSLGNDLRVDGASISFTSINLYATFFPMAHNTASTLEAMLRND
TNDQSFNDYLSAANMLYPIPANATNIPISIPSRNWAAFRGWSFTRLKTKETPSLGS
GFDPYFVYSGSIPYDGTFYLNHTFKKVSIMFDSSVSWPGNDRLLSPNEFEIKRTVD
GEGYNVAQCNMTKWFLVQMLANYNIGYQGFYIPEGYKDRMYSFFRNFQPMSR
QVVDEVNYKDFKAVIYQHNNSGFVGYMAPTMRQGQPYPANYPYPLIGTTAVNS
VTQKKFLCDRTMWRIPFSSNFMSMGALTDLGQNMLYANSAHALDMTFEVDPM
DEPTLLYLLFEVFDVVRVQPHRGIIEAVYLRTPFSAGNATT 1.4:  Serotype 41 hexon protein (SEQ ID NO:46)
VCVHVAARGAAEPPRARFPLVKMATPSMMPQWAYMHIAGQDASEYLSPGLVQ
FARATDTYFSLGNKFRNPTVAPTHDVTTDRSQRLTLRFVPVDREDTTYSYKARFT
LAGDNRVLDMASTYFDIRGVLDRGPSFKPYSGTAYNSLAPKGAPNSSQWADKE
RVNGGGNTKDVTKTFGVAAMGGEDITEKGLKIGTDTTANEPIFADKNFQPEPQV
GEENQETFVFYGGRALKKETKMKPCYGSFARPTNEKGGQAKFIIGDNGQPTENH
DITMAFDTPGGTITGGTGGPQDELKADIVMYTENINLETPDTHVVYKPGKEDDSS
EINLVQSMPNRPNYIGFRDNFVGLMYYNSTGNMGVLAGQASQLNAVVDLQDRN
TELSYQLLDSLGDRTRYFSMWNSAVDSYDPDVRIIENHGVEDELPNYCFPLDGSG
TNSAFQGKIKQNQDGDVNDDWEKDDKVSTQNQICKGNIYAMEINLQANLWKSF
LYSNVALYLDSYKYTPANVTLPTNTNTYEYMNGRVVAPSLVDAYINIGARWSLD
PMDNVNPFNHRNAGLRYRSNASGQRPLRALPHPSAPKVLCHQEPAPAPGLLHLR
VELPQGRQHDAEFPRKRPARRRLRALRQRQPLCHILPHGAQHRLHPGSHAAQR
HQRPVLQRLPLRQHALPHPGQGHQRAHLHPLAQLGRLSRLEFHPAQDQGNSFPR
LGFRPLLCLLGLHPLPRRDLLPQPHLQEGLHHVRLLGQLARQRPAVTPNEFEIKRS
VDGEGYNVAQCMTKDWFLVQMLSHYNIGYQGFHVPEGYKDRMYSFFRNFQPM
SRQVVDEINYKDYAVTLPFQHNNSGFTGYLAPTMRQGQPYPANFPYPLIGSTAVP
SVTQKKFLCDRVMWRIPFSSNFMSMGALTDLGQNMLYANSAHALDITFEVDPM
DEPTLLYLLFEVFDVVVHQPHRGVIEAVYLRTPFSAGNATT

FIG. 10 (continued)

```
                        SEQUENCE LISTING

<160> NUMBER OF SEQ ID NOS: 87

<210> SEQ ID NO 1
<211> LENGTH: 35
<212> TYPE: DNA
<213> ORGANISM: Human Adenovirus Oligonucleotide

<400> SEQUENCE: 1
cccgtgtatc catatgatgc agacaacgac cgacc                              35

<210> SEQ ID NO 2
<211> LENGTH: 27
<212> TYPE: DNA
<213> ORGANISM: Human Adenovirus Oligonucleotide

<400> SEQUENCE: 2
cccgtctacc catatggcta cgcgcgg                                       27

<210> SEQ ID NO 3
<211> LENGTH: 27
<212> TYPE: DNA
<213> ORGANISM: Human Adenovirus Oligonucleotide

<400> SEQUENCE: 3
cckgtstacc catatgaaga tgaaagc                                       27

<210> SEQ ID NO 4
<211> LENGTH: 31
<212> TYPE: DNA
<213> ORGANISM: Human Adenovirus Oligonucleotide

<400> SEQUENCE: 4
cccgtctacc catatgacac ctyctcaact c                                  31

<210> SEQ ID NO 5
<211> LENGTH: 36
<212> TYPE: DNA
<213> ORGANISM: Human Adenovirus Oligonucleotide

<400> SEQUENCE: 5
cccgtttacc catatgaccc atttgacaca tcagac                             36

<210> SEQ ID NO 6
<211> LENGTH: 30
<212> TYPE: DNA
<213> ORGANISM: Human Adenovirus Oligonucleotide
```

-continued

```
<400> SEQUENCE: 6
ccgatgcatt tattgttggg ctatatagga                                    30

<210> SEQ ID NO 7
<211> LENGTH: 30
<212> TYPE: DNA
<213> ORGANISM: Human Adenovirus Oligonucleotide

<400> SEQUENCE: 7
ccgatgcatt yattcttggg cratatagga                                    30

<210> SEQ ID NO 8
<211> LENGTH: 36
<212> TYPE: DNA
<213> ORGANISM: Human Adenovirus Oligonucleotide

<400> SEQUENCE: 8
ccgatgcatt tattcttggg raatgtawga aaagga                             36

<210> SEQ ID NO 9
<211> LENGTH: 30
<212> TYPE: DNA
<213> ORGANISM: Human Adenovirus Oligonucleotide

<400> SEQUENCE: 9
ccgatgcatt cagtcatctt ctctgatata                                    30

<210> SEQ ID NO 10
<211> LENGTH: 30
<212> TYPE: DNA
<213> ORGANISM: Human Adenovirus Oligonucleotide

<400> SEQUENCE: 10
ccgatgcatt tattgttcag ttatgtagca                                    30

<210> SEQ ID NO 11
<211> LENGTH: 30
<212> TYPE: DNA
<213> ORGANISM: Human Adenovirus Oligonucleotide

<400> SEQUENCE: 11
gccatgcatt tattgttctg ttacataaga                                    30

<210> SEQ ID NO 12
<211> LENGTH: 37
<212> TYPE: DNA
<213> ORGANISM: Human Adenovirus Oligonucleotide

<400> SEQUENCE: 12
ccgttaatta agcccttatt gttctgttac ataagaa                            37

<210> SEQ ID NO 13
<211> LENGTH: 30
<212> TYPE: DNA
<213> ORGANISM: Human Adenovirus Oligonucleotide

<400> SEQUENCE: 13
ccgatgcatt cagtcatcyt ctwtaatata                                    30

<210> SEQ ID NO 14
<211> LENGTH: 377
<212> TYPE: PRT
```

<213> ORGANISM: Human Adenovirus 8 Fiber Protein

<400> SEQUENCE: 14

```
Ser Cys Ser Cys Pro Ser Ala Pro Thr Ile Phe Met Leu Leu Gln Met
1               5                   10                  15
Lys Arg Ala Arg Pro Ser Glu Asp Thr Phe Asn Pro Val Tyr Pro Tyr
            20                  25                  30
Gly Tyr Ala Arg Asn Gln Asn Ile Pro Phe Leu Thr Pro Pro Phe Val
        35                  40                  45
Ser Ser Asn Gly Phe Gln Asn Phe Pro Pro Gly Val Leu Ser Leu Lys
    50                  55                  60
Leu Ala Asp Pro Ile Thr Ile Asn Asn Gln Asn Val Ser Leu Lys Val
65                  70                  75                  80
Gly Gly Gly Leu Thr Leu Gln Glu Glu Thr Gly Lys Leu Thr Val Asn
                85                  90                  95
Thr Glu Pro Pro Leu His Leu Thr Asn Asn Lys Leu Gly Ile Ala Leu
            100                 105                 110
Asp Ala Pro Phe Asp Val Ile Asp Asn Lys Leu Thr Leu Leu Ala Gly
        115                 120                 125
His Gly Leu Ser Ile Ile Thr Lys Glu Thr Ser Thr Leu Pro Gly Leu
    130                 135                 140
Val Asn Thr Leu Val Val Leu Thr Gly Lys Gly Ile Gly Thr Asp Leu
145                 150                 155                 160
Ser Asn Asn Gly Gly Asn Ile Cys Val Arg Val Gly Glu Gly Gly Gly
                165                 170                 175
Leu Ser Phe Asn Asp Asn Gly Asp Leu Val Ala Phe Asn Lys Lys Glu
            180                 185                 190
Asp Lys Arg Thr Leu Trp Thr Thr Pro Asp Thr Ser Pro Asn Cys Arg
        195                 200                 205
Ile Asp Gln Asp Lys Asp Ser Lys Leu Ser Leu Val Leu Thr Lys Cys
    210                 215                 220
Gly Ser Gln Ile Leu Ala Asn Val Ser Leu Ile Val Val Ala Gly Arg
225                 230                 235                 240
Tyr Lys Ile Ile Asn Asn Asn Thr Asn Pro Ala Leu Lys Gly Phe Thr
                245                 250                 255
Ile Lys Leu Leu Phe Asp Lys Asn Gly Val Leu Met Glu Ser Ser Asn
            260                 265                 270
Leu Gly Lys Ser Tyr Trp Asn Phe Arg Asn Gln Asn Ser Ile Met Ser
        275                 280                 285
Thr Ala Tyr Glu Lys Ala Ile Gly Phe Met Pro Asn Leu Val Ala Tyr
    290                 295                 300
Pro Lys Pro Thr Thr Gly Ser Lys Lys Tyr Ala Arg Asp Ile Val Tyr
305                 310                 315                 320
Gly Asn Ile Tyr Leu Gly Gly Lys Pro His Gln Pro Val Thr Ile Lys
                325                 330                 335
Thr Thr Phe Asn Gln Glu Thr Gly Cys Glu Tyr Ser Ile Thr Phe Asp
            340                 345                 350
Phe Ser Trp Ala Lys Thr Tyr Val Asn Val Glu Phe Glu Thr Thr Ser
        355                 360                 365
Phe Thr Phe Ser Tyr Ile Ala Gln Glu
    370                 375
```

<210> SEQ ID NO 15
<211> LENGTH: 376

<212> TYPE: PRT
<213> ORGANISM: Human Adenovirus 9 Fiber Protein

<400> SEQUENCE: 15

```
Ser Cys Ser Cys Pro Ser Ala Pro Thr Ile Phe Met Leu Leu Gln Met
1               5                   10                  15

Lys Arg Ala Arg Pro Ser Glu Asp Thr Phe Asn Pro Val Tyr Pro Tyr
            20                  25                  30

Gly Tyr Ala Arg Asn Gln Asn Ile Pro Phe Leu Thr Pro Pro Phe Val
        35                  40                  45

Ser Ser Asp Gly Phe Gln Asn Phe Pro Pro Gly Val Leu Ser Leu Lys
50                  55                  60

Leu Ala Asp Pro Ile Ala Ile Val Asn Gly Asn Val Ser Leu Lys Val
65                  70                  75                  80

Gly Gly Gly Leu Thr Leu Gln Asp Gly Thr Gly Lys Leu Thr Val Asn
                85                  90                  95

Ala Asp Pro Pro Leu Gln Leu Thr Asn Asn Lys Leu Gly Ile Ala Leu
            100                 105                 110

Asp Ala Pro Phe Asp Val Ile Asp Lys Leu Thr Leu Leu Ala Gly His
        115                 120                 125

Gly Leu Ser Ile Ile Thr Lys Glu Thr Ser Thr Leu Pro Gly Leu Ile
130                 135                 140

Asn Thr Leu Val Val Leu Thr Gly Lys Gly Ile Gly Thr Glu Ser Thr
145                 150                 155                 160

Asp Asn Gly Gly Ser Val Cys Val Arg Val Gly Glu Gly Gly Gly Leu
                165                 170                 175

Ser Phe Asn Asn Asp Gly Asp Leu Val Ala Phe Asn Lys Lys Glu Asp
            180                 185                 190

Lys Arg Thr Leu Trp Thr Thr Pro Asp Thr Ser Pro Asn Cys Lys Ile
        195                 200                 205

Asp Gln Asp Lys Asp Ser Lys Leu Thr Leu Val Leu Thr Lys Cys Gly
210                 215                 220

Ser Gln Ile Leu Ala Asn Val Ser Leu Ile Val Val Ala Gly Lys Tyr
225                 230                 235                 240

Lys Ile Ile Asn Asn Asn Thr Gln Pro Ala Leu Lys Gly Phe Thr Ile
                245                 250                 255

Lys Leu Leu Phe Asp Glu Asn Gly Val Leu Met Glu Ser Ser Asn Leu
            260                 265                 270

Gly Lys Ser Tyr Trp Asn Phe Arg Asn Glu Asn Ser Ile Met Ser Thr
        275                 280                 285

Ala Tyr Glu Lys Ala Ile Gly Phe Met Pro Asn Leu Val Ala Tyr Pro
290                 295                 300

Lys Pro Thr Ala Gly Ser Lys Lys Tyr Ala Arg Asp Ile Val Tyr Gly
305                 310                 315                 320

Asn Ile Tyr Leu Gly Gly Lys Pro Asp Gln Pro Val Thr Ile Lys Thr
                325                 330                 335

Thr Phe Asn Gln Glu Thr Gly Cys Glu Tyr Ser Ile Thr Phe Asp Phe
            340                 345                 350

Ser Trp Ala Lys Thr Tyr Val Asn Val Glu Phe Glu Thr Thr Ser Phe
        355                 360                 365

Thr Phe Ser Tyr Ile Ala Gln Glu
370                 375
```

<210> SEQ ID NO 16

```
<211> LENGTH: 391
<212> TYPE: PRT
<213> ORGANISM: Human Adenovirus 13 Fiber Protein
<220> FEATURE:
<221> NAME/KEY: misc_feature
<222> LOCATION: (1)..(385)
<223> OTHER INFORMATION: Xaa Can be any amino acid
<220> FEATURE:
<221> NAME/KEY: misc_feature
<222> LOCATION: (1)..(5)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (385)..(385)
<223> OTHER INFORMATION: Xaa can be any naturally occurring amino acid

<400> SEQUENCE: 16

Xaa Xaa Xaa Xaa Xaa Ser Ala Pro Thr Ile Phe Met Leu Leu Gln Met
1               5                   10                  15

Lys Arg Ala Arg Ser Ser Xaa Asp Thr Phe Asn Pro Val Tyr Pro Tyr
            20                  25                  30

Gly Tyr Ala Arg Asn Gln Asn Ile Xaa Phe Xaa Thr Pro Pro Phe Val
        35                  40                  45

Xaa Ser Asp Gly Phe Lys Asn Phe Pro Pro Gly Val Leu Ser Leu Lys
    50                  55                  60

Leu Ala Asp Pro Ile Thr Ile Ala Asn Gly Asp Val Ser Leu Lys Val
65                  70                  75                  80

Gly Gly Gly Leu Thr Leu Gln Glu Gly Ser Leu Thr Val Asp Pro Lys
                85                  90                  95

Ala Pro Leu Gln Leu Ala Asn Asp Lys Lys Leu Glu Leu Val Tyr Asp
            100                 105                 110

Asp Pro Phe Glu Val Ser Thr Asn Lys Leu Ser Leu Lys Val Gly His
        115                 120                 125

Gly Leu Lys Val Leu Asp Asp Lys Ser Ala Gly Gly Leu Lys Asp Leu
    130                 135                 140

Ile Gly Lys Leu Val Val Leu Thr Gly Lys Gly Ile Gly Ile Glu Asn
145                 150                 155                 160

Leu Gln Asn Asp Asp Gly Ser Ser Arg Gly Val Gly Ile Asn Val Arg
                165                 170                 175

Leu Gly Thr Asp Gly Gly Leu Ser Phe Asp Arg Lys Gly Glu Leu Val
            180                 185                 190

Ala Trp Asn Arg Lys Asp Asp Arg Arg Thr Leu Trp Thr Thr Pro Asp
        195                 200                 205

Pro Ser Pro Asn Cys Lys Ala Glu Thr Glu Lys Asp Ser Lys Leu Thr
    210                 215                 220

Leu Val Leu Thr Lys Cys Gly Ser Gln Ile Leu Ala Thr Val Ser Ile
225                 230                 235                 240
```

```
Ile Val Leu Lys Gly Lys Tyr Glu Phe Val Lys Lys Glu Thr Glu Pro
                245                 250                 255

Lys Ser Phe Asp Val Lys Leu Leu Phe Asp Ser Lys Gly Val Leu Leu
            260                 265                 270

Pro Thr Ser Asn Leu Ser Lys Glu Tyr Trp Asn Tyr Arg Ser Tyr Asp
        275                 280                 285

Asn Asn Ile Gly Thr Pro Tyr Glu Asn Ala Val Pro Phe Met Pro Asn
    290                 295                 300

Leu Lys Ala Tyr Pro Lys Pro Thr Lys Thr Ala Ser Asp Lys Ala Glu
305                 310                 315                 320

Asn Lys Ile Ser Ser Ala Lys Asn Lys Ile Val Ser Asn Phe Tyr Phe
                325                 330                 335

Gly Gly Gln Ala Tyr Gln Pro Gly Thr Ile Ile Lys Phe Asn Glu
            340                 345                 350

Glu Ile Asp Glu Thr Cys Ala Tyr Ser Ile Thr Phe Asn Phe Gly Trp
        355                 360                 365

Gly Lys Val Tyr Asp Asn Pro Glu Pro Phe Asp Thr Thr Ser Phe Thr
    370                 375                 380

Xaa Ser Tyr Ile Ala Gln Glu
385                 390

<210> SEQ ID NO 17
<211> LENGTH: 290
<212> TYPE: PRT
<213> ORGANISM: Human Adenovirus 14 Fiber Protein

<400> SEQUENCE: 17

His Pro Phe Ile Asn Pro Gly Phe Ile Ser Pro Asn Gly Phe Thr Gln
1               5                   10                  15

Ser Pro Asp Gly Val Leu Thr Leu Lys Cys Leu Thr Pro Leu Thr Thr
            20                  25                  30

Thr Gly Gly Ser Leu Gln Leu Lys Val Gly Gly Gly Leu Thr Val Asp
        35                  40                  45

Asp Thr Asp Gly Thr Leu Gln Glu Asn Ile Gly Ala Thr Thr Pro Leu
    50                  55                  60

Val Lys Thr Gly His Ser Ile Gly Leu Ser Leu Gly Ala Gly Leu Gly
65                  70                  75                  80

Thr Asp Glu Asn Lys Leu Cys Thr Lys Leu Gly Glu Gly Leu Thr Phe
                85                  90                  95

Asn Ser Asn Asn Ile Cys Ile Asp Asn Ile Asn Thr Leu Trp Thr
            100                 105                 110

Gly Val Asn Pro Thr Glu Ala Asn Cys Gln Met Met Asp Ser Ser Glu
        115                 120                 125

Ser Asn Asp Cys Lys Leu Ile Leu Thr Leu Val Lys Thr Gly Ala Leu
    130                 135                 140

Val Thr Ala Phe Val Tyr Val Ile Gly Val Ser Asn Asn Phe Asn Met
145                 150                 155                 160

Leu Thr Thr Tyr Arg Asn Ile Asn Phe Thr Ala Glu Leu Phe Phe Asp
                165                 170                 175

Ser Ala Gly Asn Leu Leu Thr Ser Leu Ser Ser Leu Lys Thr Pro Leu
            180                 185                 190

Asn His Lys Ser Gly Gln Thr Trp Leu Leu Val Pro Leu Leu Met Leu
        195                 200                 205

Lys Val Ser Cys Pro Ala Gln Leu Leu Ile Leu Ser Ile Ile Ile Leu
    210                 215                 220
```

-continued

Glu Lys Asn Lys Thr Thr Phe Thr Glu Leu Val Thr Thr Gln Leu Val
225                 230                 235                 240

Ile Thr Leu Leu Phe Pro Leu Thr Ile Ser Val Met Leu Asn Gln Arg
                245                 250                 255

Ala Ile Arg Ala Asp Thr Ser Tyr Cys Ile Arg Ile Thr Trp Ser Trp
            260                 265                 270

Asn Thr Gly Asp Ala Pro Glu Gly Gln Thr Ser Ala Thr Thr Leu Val
        275                 280                 285

Thr Ser
    290

<210> SEQ ID NO 18
<211> LENGTH: 344
<212> TYPE: PRT
<213> ORGANISM: Human Adenovirus 20 Fiber Protein

<400> SEQUENCE: 18

Ile Gln Asn Ile Pro Phe Leu Thr Pro Pro Phe Val Ser Ser Asp Gly
1               5                   10                  15

Leu Gln Asn Phe Pro Pro Gly Val Leu Ser Leu Lys Leu Ala Asp Pro
            20                  25                  30

Ile Ala Ile Val Asn Gly Asn Val Ser Leu Lys Val Gly Gly Gly Ile
        35                  40                  45

Thr Val Glu Gln Asp Ser Gly Gln Leu Ile Ala Asn Pro Lys Ala Pro
    50                  55                  60

Leu Gln Val Ala Asn Asp Lys Leu Glu Leu Ser Tyr Ala Tyr Pro Phe
65                  70                  75                  80

Glu Thr Ser Ala Asn Lys Leu Ser Leu Lys Val Gly Gln Gly Leu Lys
                85                  90                  95

Val Leu Asp Glu Lys Asp Ser Gly Gly Leu Gln Asn Leu Leu Gly Lys
            100                 105                 110

Leu Val Val Leu Thr Gly Lys Gly Ile Gly Val Glu Glu Leu Lys Asn
        115                 120                 125

Pro Asp Asn Thr Asn Arg Gly Val Gly Ile Asn Val Arg Leu Gly Lys
    130                 135                 140

Asp Gly Gly Leu Ser Phe Asn Lys Asn Gly Glu Leu Val Ala Trp Asn
145                 150                 155                 160

Lys His Asn Asp Thr Gly Thr Leu Trp Thr Thr Pro Asp Pro Ser Pro
                165                 170                 175

Asn Cys Lys Ile Glu Glu Val Lys Asp Ser Lys Leu Thr Leu Val Leu
            180                 185                 190

Thr Lys Cys Gly Ser Gln Ile Leu Ala Thr Met Ala Phe Gln Val Val
        195                 200                 205

Lys Gly Thr Tyr Glu Asn Ile Ser Lys Asn Thr Ala Lys Asn Ser Phe
    210                 215                 220

Ser Ile Lys Leu Leu Phe Asp Asp Asn Gly Lys Leu Leu Glu Gly Ser
225                 230                 235                 240

Ser Leu Asp Lys Asp Tyr Trp Asn Phe Arg Ser Asp Asp Ser Ile Ile
                245                 250                 255

Pro Asn Gln Tyr Asp Asn Ala Val Pro Phe Met Pro Asn Leu Lys Ala
            260                 265                 270

Tyr Pro Lys Pro Ser Thr Val Leu Pro Ser Thr Asp Lys Asn Ser Asn
        275                 280                 285

Gly Lys Asn Thr Ile Val Ser Asn Leu Tyr Leu Glu Gly Lys Ala Tyr

```
                290                 295                 300
Gln Pro Val Ala Val Thr Ile Thr Phe Asn Lys Glu Ile Gly Cys Thr
305                 310                 315                 320

Tyr Ser Ile Thr Phe Asp Phe Gly Trp Ala Lys Thr Tyr Asp Val Pro
                325                 330                 335

Ile Pro Asp Ser Ser Ser Phe Thr
            340

<210> SEQ ID NO 19
<211> LENGTH: 345
<212> TYPE: PRT
<213> ORGANISM: Human Adenovirus 23 Fiber Protein

<400> SEQUENCE: 19

Gln Asn Ile Pro Phe Leu Thr Pro Pro Phe Val Ser Asp Gly Phe
1               5                   10                  15

Gln Asn Phe Pro Pro Gly Val Leu Ser Leu Lys Leu Ala Asp Pro Ile
                20                  25                  30

Ala Ile Thr Asn Gly Asp Val Ser Leu Lys Val Gly Gly Gly Leu Thr
            35                  40                  45

Val Glu Gln Asp Ser Gly Asn Leu Lys Val Asn Thr Lys Ala Pro Leu
    50                  55                  60

Gln Val Ala Ala Asp Lys Gln Leu Glu Ile Ala Leu Ala Asp Pro Phe
65                  70                  75                  80

Glu Val Ser Lys Gly Arg Leu Gly Ile Lys Ala Gly His Gly Leu Lys
                85                  90                  95

Val Ile Asp Asn Ser Ile Ser Gly Leu Glu Gly Leu Val Gly Thr Leu
                100                 105                 110

Val Val Leu Thr Gly His Gly Ile Gly Thr Glu Asn Leu Leu Asn Asn
            115                 120                 125

Asp Gly Ser Ser Arg Gly Val Gly Ile Asn Val Arg Leu Gly Lys Asp
    130                 135                 140

Gly Gly Leu Ser Phe Asp Lys Lys Gly Asp Leu Val Ala Trp Asn Lys
145                 150                 155                 160

Lys Tyr Asp Thr Arg Thr Leu Trp Thr Thr Pro Asp Pro Ser Pro Asn
                165                 170                 175

Cys Lys Val Ile Glu Ala Lys Asp Ser Lys Leu Thr Leu Val Leu Thr
                180                 185                 190

Lys Cys Gly Ser Gln Ile Leu Ala Asn Met Ser Leu Leu Ile Leu Lys
            195                 200                 205

Gly Thr Tyr Glu Tyr Ile Ser Asn Ala Ile Ala Asn Lys Ser Phe Thr
    210                 215                 220

Ile Lys Leu Leu Phe Asn Asp Lys Gly Val Leu Met Asp Gly Ser Ser
225                 230                 235                 240

Leu Asp Lys Asp Tyr Trp Asn Tyr Lys Ser Asp Asp Ser Val Met Ser
                245                 250                 255

Lys Ala Tyr Glu Asn Ala Val Pro Phe Met Pro Asn Leu Lys Ala Tyr
                260                 265                 270

Pro Asn Pro Thr Thr Ser Thr Thr Asn Pro Ser Thr Asp Lys Lys Ser
            275                 280                 285

Asn Gly Lys Asn Ala Ile Val Ser Asn Val Tyr Leu Glu Gly Arg Ala
    290                 295                 300

Tyr Gln Pro Val Ala Ile Thr Ile Thr Phe Asn Lys Glu Thr Gly Cys
305                 310                 315                 320
```

```
Thr Tyr Ser Met Thr Phe Asp Phe Gly Trp Ser Lys Val Tyr Asn Pro
            325                 330                 335

Ile Pro Phe Asp Thr Ser Ser Leu Thr
            340                 345

<210> SEQ ID NO 20
<211> LENGTH: 389
<212> TYPE: PRT
<213> ORGANISM: Human Adenovirus 24 Fiber Protein

<400> SEQUENCE: 20

Ser Cys Ser Cys Pro Ser Ala Pro Thr Ile Phe Met Leu Leu Gln Met
1               5                   10                  15

Lys Arg Ala Arg Pro Ser Glu Asp Thr Phe Asn Pro Val Tyr Pro Tyr
            20                  25                  30

Gly Tyr Ala Arg Asn Gln Asn Ile Pro Phe Leu Thr Pro Pro Phe Val
            35                  40                  45

Ser Ser Asp Gly Phe Gln Asn Phe Pro Gly Val Leu Ser Leu Lys Leu
        50                  55                  60

Ala Asp Pro Ile Ala Ile Thr Asn Gly Asp Tyr Ser Leu Lys Val Gly
65              70                  75                  80

Gly Gly Leu Thr Val Glu Lys Asp Ser Gly Asn Leu Lys Val Asn Pro
                85                  90                  95

Lys Ala Pro Leu Gln Val Thr Thr Asp Lys Gln Leu Glu Ile Ala Leu
            100                 105                 110

Ala Tyr Pro Phe Glu Val Ser Asn Gly Lys Leu Gly Ile Lys Ala Gly
            115                 120                 125

His Gly Leu Lys Val Ile Asp Lys Ile Ala Gly Leu Glu Gly Leu Ala
        130                 135                 140

Gly Thr Leu Val Val Leu Thr Gly Lys Gly Ile Gly Thr Glu Asn Leu
145             150                 155                 160

Glu Asn Ser Asp Gly Ser Ser Arg Gly Val Gly Ile Asn Val Arg Leu
                165                 170                 175

Ala Lys Asp Gly Gly Leu Ser Phe Asp Lys Lys Gly Asp Leu Val Ala
            180                 185                 190

Trp Asn Lys His Asp Asp Arg Arg Thr Leu Trp Thr Thr Pro Asp Pro
            195                 200                 205

Ser Pro Asn Cys Thr Ile Asp Gln Glu Arg Asp Ser Lys Leu Thr Leu
        210                 215                 220

Val Leu Thr Lys Cys Gly Ser Gln Ile Leu Ala Asn Val Ser Leu Leu
225             230                 235                 240

Val Val Lys Gly Lys Phe Ser Asn Ile Asn Asn Asn Thr Asn Pro Thr
                245                 250                 255

Asp Lys Lys Ile Thr Val Lys Leu Leu Phe Asn Glu Lys Gly Val Leu
            260                 265                 270

Met Asp Ser Ser Thr Leu Lys Lys Glu Tyr Trp Asn Tyr Arg Asn Asp
        275                 280                 285

Asn Ser Thr Val Ser Gln Ala Tyr Asp Asn Ala Val Pro Phe Met Pro
    290                 295                 300

Asn Ile Lys Ala Tyr Pro Lys Pro Thr Thr Ser Ala Lys Pro
305                 310                 315                 320

Glu Asp Lys Lys Ser Ala Ala Lys Arg Tyr Ile Val Ser Asn Val Tyr
            325                 330                 335

Ile Gly Gly Leu Pro Asp Lys Thr Val Val Ile Thr Ile Lys Phe Asn
            340                 345                 350
```

```
Ala Glu Thr Glu Cys Ala Tyr Ser Ile Thr Phe Glu Phe Thr Trp Ala
            355                 360                 365

Lys Thr Phe Glu Asp Val Trp Phe Asp Ser Ser Phe Thr Phe Ser
        370                 375                 380

Tyr Ile Ala Gln Glu
385

<210> SEQ ID NO 21
<211> LENGTH: 374
<212> TYPE: PRT
<213> ORGANISM: Human Adenovirus 25 Fiber Protein
<220> FEATURE:
<221> NAME/KEY: misc_feature
<222> LOCATION: (141)..(141)
<223> OTHER INFORMATION: Xaa can be any amino acid
<220> FEATURE:
<221> NAME/KEY: misc_feature
<222> LOCATION: (141)..(141)
<223> OTHER INFORMATION: Xaa can be any naturally occurring amino acid

<400> SEQUENCE: 21

Ser Cys Ser Cys Pro Ser Ala Pro Thr Ile Phe Met Leu Leu Gln Met
1               5                   10                  15

Lys Arg Ala Arg Pro Ser Glu Asp Thr Phe Asn Pro Val Tyr Pro Gly
            20                  25                  30

Tyr Ala Arg Asn Gln Asn Ile Pro Phe Leu Thr Ile Pro Pro Phe Val
        35                  40                  45

Ser Ser Asp Gly Phe Gln Asn Phe Pro Pro Gly Val Leu Ser Leu Lys
    50                  55                  60

Leu Ala Asp Pro Ile Thr Ile Ser Asn Gly Asp Val Ser Leu Lys Val
65                  70                  75                  80

Gly Gly Gly Leu Thr Val Glu Gln Asp Ser Gly Asn Leu Ser Val Asn
                85                  90                  95

Pro Lys Ala Pro Leu Gln Val Gly Thr Asp Lys Lys Leu Glu Leu Ala
            100                 105                 110

Leu Ala Pro Pro Phe Asn Val Lys Asp Asn Lys Leu Asp Leu Leu Val
        115                 120                 125

Gly Asp Gly Leu Lys Val Ile Asp Lys Ser Ile Ser Xaa Leu Pro Gly
    130                 135                 140

Leu Leu Asn Tyr Leu Val Val Leu Thr Gly Lys Gly Ile Gly Asn Glu
145                 150                 155                 160

Glu Leu Lys Leu Asp Asp Gly Ser Asn Lys Val Gly Leu Cys Val Arg
                165                 170                 175

Ile Gly Glu Gly Gly Gly Leu Thr Phe Asp Asp Lys Gly Tyr Leu Val
            180                 185                 190

Ala Trp Asn Lys Lys His Asp Ile Arg Thr Leu Trp Thr Thr Leu Asp
        195                 200                 205

Pro Ser Pro Asn Cys Arg Ile Asp Val Asp Lys Asp Ser Lys Leu Thr
    210                 215                 220

Leu Val Leu Thr Lys Cys Gly Ser Gln Ile Leu Ala Asn Val Ser Leu
225                 230                 235                 240

Leu Val Val Lys Gly Arg Phe Gln Asn Leu Asn Tyr Lys Thr Asn Pro
                245                 250                 255

Asn Leu Pro Lys Thr Phe Thr Ile Lys Leu Leu Phe Asp Glu Asn Gly
            260                 265                 270

Ile Leu Lys Asp Ser Ser Asn Leu Asp Lys Asn Tyr Trp Asn Tyr Arg
        275                 280                 285
```

```
Asn Gly Asn Ser Ile Leu Ala Glu Gln Tyr Lys Asn Ala Val Gly Phe
        290                 295                 300

Met Pro Asn Leu Ala Ala Tyr Pro Lys Ser Thr Thr Gln Ser Lys
305                 310                 315                 320

Leu Tyr Ala Arg Asn Thr Ile Phe Gly Asn Thr Tyr Leu Asp Ser Gln
                325                 330                 335

Ala Tyr Asn Pro Val Val Ile Lys Ile Thr Phe Asn Gln Glu Ala Asp
                340                 345                 350

Ser Ala Tyr Ser Ile Thr Leu Asn Tyr Ser Trp Gly Lys Asp Tyr Glu
                355                 360                 365

Asn Ile Pro Phe Asp Ser
        370

<210> SEQ ID NO 22
<211> LENGTH: 334
<212> TYPE: PRT
<213> ORGANISM: Human Adenovirus 27 Fiber Protein

<400> SEQUENCE: 22

Ile Pro Phe Leu Thr Pro Pro Phe Val Ser Ser Asp Gly Phe Lys Asn
1               5                   10                  15

Phe Pro Pro Gly Val Leu Ser Leu Lys Leu Ala Asp Pro Ile Thr Ile
                20                  25                  30

Thr Asn Gly Asp Val Ser Leu Lys Val Gly Gly Gly Leu Val Val Glu
            35                  40                  45

Lys Glu Ser Gly Lys Leu Ser Val Asp Pro Lys Thr Pro Leu Gln Val
        50                  55                  60

Ala Ser Asp Asn Lys Leu Glu Leu Ser Tyr Asn Ala Pro Phe Lys Val
65                  70                  75                  80

Glu Asn Asp Lys Leu Ser Leu Asp Val Gly His Gly Leu Lys Val Ile
                85                  90                  95

Gly Asn Glu Val Ser Ser Leu Pro Gly Leu Ile Asn Lys Leu Val Val
            100                 105                 110

Leu Thr Gly Lys Gly Ile Gly Thr Glu Leu Leu Lys Glu Gln Asn Ser
        115                 120                 125

Asp Lys Ile Ile Gly Val Gly Ile Asn Val Arg Ala Arg Gly Gly Leu
    130                 135                 140

Ser Phe Asp Asn Asp Gly Tyr Leu Val Ala Trp Asn Pro Lys Tyr Asp
145                 150                 155                 160

Thr Arg Thr Leu Trp Thr Thr Pro Asp Thr Ser Pro Asn Cys Lys Met
                165                 170                 175

Leu Thr Lys Lys Asp Ser Lys Leu Thr Leu Thr Leu Thr Lys Cys Gly
                180                 185                 190

Ser Gln Ile Leu Gly Asn Val Ser Leu Leu Ala Val Ser Gly Lys Tyr
            195                 200                 205

Leu Asn Met Thr Lys Asp Glu Thr Gly Val Lys Ile Ile Leu Leu Phe
        210                 215                 220

Asp Arg Asn Gly Val Leu Met Gln Glu Ser Ser Leu Asp Lys Glu Tyr
225                 230                 235                 240

Trp Met Tyr Arg Asn Asp Asn Asn Val Ile Gly Thr Pro Tyr Glu Asn
                245                 250                 255

Ala Val Gly Phe Met Pro Asn Leu Val Ala Tyr Pro Lys Pro Thr Ser
            260                 265                 270

Ala Asp Ala Lys Asn Tyr Ser Arg Ser Lys Ile Ile Ser Asn Tyr Leu
```

```
            275                 280                 285
Lys Gly Leu Ile Tyr Gln Pro Val Ile Ile Ala Ser Phe Asn Gln
        290                 295                 300

Glu Thr Thr Asn Gly Cys Val Tyr Ser Ile Ser Phe Asp Phe Cys
305                 310                 315                 320

Ser Lys Asp Tyr Thr Gly Gln Gln Phe Asp Val Thr Ser Phe
                325                 330

<210> SEQ ID NO 23
<211> LENGTH: 374
<212> TYPE: PRT
<213> ORGANISM: Human Adenovirus 28 Fiber Protein

<400> SEQUENCE: 23

Ser Cys Ser Cys Pro Ser Ala Pro Thr Ile Phe Met Leu Leu Gln Met
1               5                   10                  15

Lys Arg Ala Arg Pro Ser Glu Asp Thr Phe Asn Pro Val Tyr Pro Tyr
                20                  25                  30

Gly Tyr Ala Arg Asn Gln Asn Ile Pro Phe Leu Thr Pro Pro Phe Val
            35                  40                  45

Ser Ser Asp Gly Phe Gln Asn Phe Pro Pro Gly Val Leu Ser Leu Lys
        50                  55                  60

Leu Ala Asp Pro Ile Thr Ile Ala Asn Gly Asp Val Ser Leu Lys Leu
65                  70                  75                  80

Gly Gly Gly Leu Thr Val Glu Lys Glu Ser Gly Asn Leu Thr Val Asn
                85                  90                  95

Pro Lys Ala Pro Leu Gln Val Ala Ser Gly Gln Leu Glu Leu Ala Tyr
            100                 105                 110

Tyr Ser Pro Phe Asp Val Lys Asn Asn Met Leu Thr Leu Lys Ala Gly
        115                 120                 125

His Gly Leu Ala Val Val Thr Lys Asp Asn Thr Asp Leu Gln Pro Leu
130                 135                 140

Met Gly Thr Leu Val Val Leu Thr Gly Lys Gly Ile Gly Thr Gly Thr
145                 150                 155                 160

Ser Ala His Gly Gly Thr Ile Asp Val Arg Ile Gly Lys Asn Gly Ser
                165                 170                 175

Leu Ala Phe Asp Lys Asn Gly Asp Leu Val Ala Trp Asp Lys Glu Asn
            180                 185                 190

Asp Arg Arg Thr Leu Trp Thr Thr Pro Asp Thr Ser Pro Asn Cys Lys
        195                 200                 205

Met Ser Glu Val Lys Asp Ser Lys Leu Thr Leu Ile Leu Thr Lys Cys
210                 215                 220

Gly Ser Gln Ile Leu Gly Ser Val Ser Leu Leu Ala Val Lys Gly Glu
225                 230                 235                 240

Tyr Gln Asn Met Thr Ala Ser Thr Asn Lys Asn Val Lys Ile Thr Leu
                245                 250                 255

Leu Phe Asp Ala Asn Gly Val Leu Leu Glu Gly Ser Ser Leu Asp Lys
            260                 265                 270

Glu Tyr Trp Asn Phe Arg Asn Asn Asp Ser Thr Val Ser Gly Lys Tyr
        275                 280                 285

Glu Asn Ala Val Pro Phe Met Pro Asn Ile Thr Ala Tyr Lys Pro Val
            290                 295                 300

Asn Ser Lys Ser Tyr Ala Arg Ser His Ile Phe Gly Asn Val Tyr Ile
305                 310                 315                 320
```

```
Asp Ala Lys Pro Tyr Asn Pro Val Val Ile Lys Ile Ser Phe Asn Gln
            325                 330                 335

Glu Thr Gln Asn Asn Cys Val Tyr Ser Ile Ser Phe Asp Tyr Thr Cys
            340                 345                 350

Ser Lys Glu Tyr Thr Gly Met Gln Phe Asp Val Thr Ser Phe Thr Phe
            355                 360                 365

Ser Tyr Ile Ala Gln Glu
            370

<210> SEQ ID NO 24
<211> LENGTH: 343
<212> TYPE: PRT
<213> ORGANISM: Human Adenovirus 29 Fiber Protein

<400> SEQUENCE: 24

Gln Asn Ile Pro Phe Leu Thr Pro Pro Phe Val Ser Ser Asp Gly Phe
1               5                   10                  15

Lys Asn Phe Pro Pro Gly Val Leu Ser Leu Lys Leu Ala Asp Pro Ile
            20                  25                  30

Ala Ile Thr Asn Gly Asp Val Ser Leu Lys Val Gly Gly Gly Leu Thr
        35                  40                  45

Val Glu Gln Asp Ser Gly Asn Leu Ser Val Asn Pro Lys Ala Pro Leu
50                  55                  60

Gln Val Gly Thr Asp Lys Lys Leu Glu Leu Ala Leu Ala Pro Pro Phe
65                  70                  75                  80

Asp Val Arg Asp Asn Lys Leu Ala Ile Leu Val Gly Asp Gly Leu Lys
                85                  90                  95

Val Ile Asp Arg Ser Ile Ser Asp Leu Pro Gly Leu Leu Asn Tyr Leu
            100                 105                 110

Val Val Leu Thr Gly Lys Gly Ile Gly Asn Glu Glu Leu Lys Asn Asp
        115                 120                 125

Asp Gly Ser Asn Lys Gly Val Gly Leu Cys Val Arg Ile Gly Glu Gly
    130                 135                 140

Gly Gly Leu Thr Phe Asp Asp Lys Gly Tyr Leu Val Ala Trp Asn Asn
145                 150                 155                 160

Lys His Asp Ile Arg Thr Leu Trp Thr Thr Leu Asp Pro Ser Pro Asn
                165                 170                 175

Cys Lys Ile Asp Ile Glu Lys Asp Ser Lys Leu Thr Leu Val Leu Thr
            180                 185                 190

Lys Cys Gly Ser Gln Ile Leu Ala Asn Val Ser Leu Ile Ile Val Asn
        195                 200                 205

Gly Lys Phe Lys Ile Leu Asn Asn Lys Thr Asp Pro Ser Leu Pro Lys
    210                 215                 220

Ser Phe Asn Ile Lys Leu Leu Phe Asp Gln Asn Gly Val Leu Leu Glu
225                 230                 235                 240

Asn Ser Asn Ile Glu Lys Gln Tyr Leu Asn Phe Arg Ser Gly Asp Ser
                245                 250                 255

Ile Leu Pro Glu Pro Tyr Lys Asn Ala Ile Gly Phe Met Pro Asn Leu
            260                 265                 270

Leu Ala Tyr Ala Lys Ala Thr Thr Asp Gln Ser Lys Ile Tyr Ala Arg
        275                 280                 285

Asn Thr Thr Tyr Gly Asn Ile Tyr Leu Asp Asn Gln Pro Tyr Asn Pro
    290                 295                 300

Val Val Ile Lys Ile Thr Phe Asn Asn Glu Ala Asp Ser Ala Tyr Ser
305                 310                 315                 320
```

```
Ile Thr Phe Asn Tyr Ser Trp Thr Lys Asp Tyr Asp Asn Ile Pro Phe
            325                 330                 335

Asp Ser Thr Ser Phe Thr Ser
            340

<210> SEQ ID NO 25
<211> LENGTH: 385
<212> TYPE: PRT
<213> ORGANISM: Human Adenovirus 30 Fiber Protein
<220> FEATURE:
<221> NAME/KEY: misc_feature
<222> LOCATION: (23)..(97)
<223> OTHER INFORMATION: Xaa Can be any amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (186)..(186)
<223> OTHER INFORMATION: Xaa can be any naturally occurring amino acid

<400> SEQUENCE: 25

Ser Cys Ser Cys Pro Ser Ala Pro Thr Ile Phe Met Leu Leu Gln Met
1               5                   10                  15

Lys Arg Ala Arg Pro Ser Xaa Asp Thr Phe Asn Pro Val Tyr Pro Tyr
            20                  25                  30

Gly Tyr Ala Arg Asn Gln Asn Ile Pro Phe Xaa Thr Pro Pro Phe Val
            35                  40                  45

Xaa Ser Asp Gly Phe Lys Asn Phe Pro Pro Gly Val Leu Ser Leu Lys
50                  55                  60

Leu Ala Asp Pro Ile Ala Ile Thr Asn Gly Asp Tyr Ser Leu Lys Val
65                  70                  75                  80

Gly Gly Gly Leu Thr Val Glu Gln Asp Ser Gly Asn Leu Ser Val Asn
            85                  90                  95

Xaa Lys Ala Pro Leu Gln Val Gly Thr Asp Lys Lys Leu Glu Leu Ala
            100                 105                 110

Leu Ala Pro Pro Phe Asp Val Arg Asp Asn Lys Leu Ala Ile Leu Val
            115                 120                 125

Gly Asp Gly Leu Lys Val Ile Asp Arg Ser Ile Ser Asp Leu Pro Gly
            130                 135                 140

Leu Leu Asn Tyr Leu Val Val Xaa Thr Gly Lys Gly Ile Gly Asn Glu
145                 150                 155                 160

Glu Leu Lys Asn Asp Asp Gly Ser Asn Lys Gly Val Gly Leu Cys Val
                165                 170                 175

Arg Ile Gly Glu Gly Gly Gly Leu Thr Xaa Asp Asp Lys Gly Tyr Leu
            180                 185                 190
```

-continued

```
Val Ala Trp Asn Asn Lys His Asp Ile Arg Thr Leu Trp Thr Thr Leu
        195                 200                 205

Asp Pro Ser Pro Asn Cys Lys Ile Asp Glu Lys Asp Ser Lys Leu Thr
    210                 215                 220

Leu Val Leu Thr Lys Cys Gly Ser Gln Ile Leu Ala Asn Val Ser Leu
225                 230                 235                 240

Ile Ile Val Asn Gly Lys Phe Lys Ile Leu Asn Asn Lys Thr Asp Pro
                245                 250                 255

Ser Leu Pro Lys Ser Phe Asn Ile Lys Leu Leu Phe Asp Gln Asn Gly
            260                 265                 270

Val Leu Leu Glu Asn Ser Asn Ile Glu Lys Gln Tyr Leu Asn Phe Arg
        275                 280                 285

Ser Gly Asp Ser Ile Leu Pro Glu Pro Tyr Lys Asn Ala Ile Gly Phe
    290                 295                 300

Met Pro Asn Leu Leu Ala Tyr Ala Lys Ala Thr Thr Asp Gln Ser Lys
305                 310                 315                 320

Thr Tyr Ala Arg Asn Thr Ile Tyr Gly Asn Ile Tyr Leu Asp Asn Gln
                325                 330                 335

Pro Tyr Asn Pro Val Val Ile Lys Ile Thr Phe Asn Asn Glu Ala Asp
            340                 345                 350

Ser Ala Tyr Ser Ile Thr Phe Asn Tyr Ser Trp Thr Lys Asp Tyr Asp
        355                 360                 365

Asn Ile Pro Phe Asp Ser Thr Ser Phe Thr Ser Tyr Ile Ala Gln
    370                 375                 380

Glu
385

<210> SEQ ID NO 26
<211> LENGTH: 389
<212> TYPE: PRT
<213> ORGANISM: Human Adenovirus 32 Fiber Protein

<400> SEQUENCE: 26

Ser Cys Ser Pro Ser Ala Pro Thr Ile Phe Met Leu Leu Gln Met Lys
1               5                   10                  15

Arg Ala Arg Pro Ser Glu Asp Thr Phe Asn Pro Val Tyr Pro Tyr Gly
            20                  25                  30

Tyr Ala Arg Asn Gln Asn Ile Pro Phe Leu Thr Pro Pro Phe Val Ser
        35                  40                  45

Ser Asp Gly Phe Gln Asn Phe Pro Pro Gly Val Leu Ser Leu Lys Leu
    50                  55                  60

Ala Asp Pro Ile Thr Ile Ala Asn Gly Asn Val Ser Leu Lys Val Gly
65                  70                  75                  80

Gly Gly Leu Thr Leu Glu Gln Asp Ser Gly Lys Leu Ile Val Asn Pro
                85                  90                  95

Lys Ala Pro Leu Gln Val Ala Asn Asp Lys Leu Glu Leu Ser Tyr Ala
            100                 105                 110

Asp Pro Phe Glu Thr Ser Ala Asn Lys Leu Ser Leu Lys Val Gly His
        115                 120                 125

Gly Leu Lys Val Leu Asp Glu Lys Asn Ala Gly Gly Leu Lys Asp Leu
    130                 135                 140

Ile Gly Thr Leu Val Val Leu Thr Asp Lys Gly Ile Gly Val Glu Glu
145                 150                 155                 160

Leu Lys Asn Ala Asp Asn Thr Asn Arg Gly Val Gly Ile Asn Val Arg
                165                 170                 175
```

-continued

Leu Gly Lys Asp Gly Gly Leu Ser Phe Asp Lys Lys Gly Asp Leu Val
            180                 185                 190

Ala Trp Asn Lys His Asp Asp Arg Arg Thr Leu Trp Thr Thr Pro Asp
        195                 200                 205

Pro Ser Pro Asn Cys Thr Thr Asp Glu Glu Arg Asp Ser Lys Leu Thr
    210                 215                 220

Leu Val Leu Thr Lys Cys Gly Ser Gln Ile Leu Ala Asn Val Ser Leu
225                 230                 235                 240

Leu Val Val Lys Gly Lys Phe Ser Asn Ile Asn Asn Thr Asn Pro
            245                 250                 255

Thr Asp Lys Lys Ile Thr Val Lys Leu Leu Phe Asn Glu Lys Gly Val
        260                 265                 270

Leu Met Asp Ser Ser Ser Leu Lys Glu Tyr Trp Asn Tyr Arg Asn
    275                 280                 285

Asp Asn Ser Thr Ser Gln Ala Tyr Asp Asn Ala Val Pro Phe Met Pro
    290                 295                 300

Asn Ile Lys Ala Tyr Pro Lys Pro Thr Thr Asp Thr Ser Ala Lys Pro
305                 310                 315                 320

Glu Asp Lys Lys Ser Ala Ala Lys Arg Tyr Ile Val Ser Asn Val Tyr
            325                 330                 335

Ile Gly Gly Leu Pro Asp Lys Thr Val Val Ile Thr Ile Lys Leu Asn
        340                 345                 350

Ala Glu Thr Glu Ser Ala Tyr Ser Met Thr Phe Glu Phe Thr Trp Ala
    355                 360                 365

Lys Thr Phe Glu Asn Leu Gln Phe Asp Ser Ser Ser Phe Thr Phe Ser
    370                 375                 380

Tyr Ile Ala Gln Glu
385

<210> SEQ ID NO 27
<211> LENGTH: 391
<212> TYPE: PRT
<213> ORGANISM: Human Adenovirus 33 Fiber Protein

<400> SEQUENCE: 27

Ser Cys Ser Cys Pro Ser Ala Pro Thr Ile Phe Met Leu Leu Gln Met
1               5                   10                  15

Lys Arg Ala Arg Pro Ser Glu Asp Thr Phe Asn Pro Val Tyr Pro Tyr
            20                  25                  30

Gly Tyr Ala Arg Asn Gln Asn Ile Pro Phe Leu Thr Pro Pro Phe Val
        35                  40                  45

Ser Ser Asp Gly Phe Lys Asn Phe Pro Pro Gly Val Leu Ser Leu Lys
    50                  55                  60

Leu Ala Asp Pro Ile Thr Ile Thr Asn Gly Asp Val Ser Leu Lys Val
65                  70                  75                  80

Gly Gly Gly Leu Thr Leu Gln Glu Gly Ser Leu Thr Val Asn Pro Lys
                85                  90                  95

Ala Pro Leu Gln Leu Ala Asn Asp Lys Lys Leu Glu Leu Val Tyr Asp
            100                 105                 110

Asp Pro Phe Glu Val Ser Thr Asn Lys Leu Ser Leu Lys Val Gly His
        115                 120                 125

Gly Leu Lys Val Leu Asp Asp Lys Ser Ala Gly Gly Leu Gln Asp Leu
    130                 135                 140

Ile Gly Lys Leu Val Val Leu Thr Gly Lys Gly Ile Gly Ile Glu Asn

```
                145                 150                 155                 160
Leu Gln Asn Asp Asp Gly Ser Ser Arg Gly Val Gly Ile Asn Val Arg
                165                 170                 175

Leu Gly Thr Asp Gly Gly Leu Ser Phe Asp Arg Lys Gly Glu Leu Val
                180                 185                 190

Ala Trp Asn Arg Lys Asp Asp Arg Arg Thr Leu Trp Thr Thr Pro Asp
                195                 200                 205

Pro Ser Pro Asn Cys Lys Ala Glu Thr Glu Lys Asp Ser Lys Leu Thr
                210                 215                 220

Leu Val Leu Thr Lys Cys Gly Ser Gln Ile Leu Ala Thr Val Ser Ile
225                 230                 235                 240

Ile Val Leu Lys Gly Lys Tyr Glu Phe Val Lys Lys Glu Thr Glu Pro
                245                 250                 255

Lys Ser Phe Asp Val Lys Leu Leu Phe Asp Ser Lys Gly Val Leu Leu
                260                 265                 270

Pro Thr Ser Asn Leu Ser Lys Glu Tyr Trp Asn Tyr Arg Ser Tyr Asp
                275                 280                 285

Asn Asn Ile Gly Thr Pro Tyr Glu Asn Ala Val Pro Phe Met Pro Asn
                290                 295                 300

Leu Lys Ala Tyr Pro Lys Pro Thr Lys Thr Ala Ser Asp Lys Ala Glu
305                 310                 315                 320

Asn Lys Ile Ser Ser Ala Lys Asn Lys Ile Val Ser Asn Phe Tyr Phe
                325                 330                 335

Gly Gly Gln Ala Tyr Gln Pro Gly Thr Ile Ile Lys Phe Asn Glu
                340                 345                 350

Glu Ile Asp Glu Thr Cys Ala Tyr Ser Ile Thr Phe Asn Phe Gly Trp
                355                 360                 365

Gly Lys Val Tyr Asp Asn Pro Phe Pro Phe Asp Thr Thr Ser Phe Thr
                370                 375                 380

Phe Ser Tyr Ile Ala Gln Glu
385                 390

<210> SEQ ID NO 28
<211> LENGTH: 338
<212> TYPE: PRT
<213> ORGANISM: Human Adenovirus 34 Fiber Protein

<400> SEQUENCE: 28

Ser Cys Ser Cys Pro Ser Ala Pro Thr Ile Phe Met Leu Leu Gln Met
1               5                   10                  15

Lys Arg Ala Arg Pro Ser Glu Asp Thr Phe Asn Pro Val Tyr Pro Tyr
                20                  25                  30

Glu Asp Glu Ser Thr Ser Gln His Pro Phe Ile Asn Pro Gly Phe Ile
                35                  40                  45

Ser Pro Asn Gly Phe Thr Gln Ser Pro Asp Gly Val Leu Thr Leu Lys
                50                  55                  60

Cys Leu Thr Pro Leu Thr Thr Thr Gly Gly Ser Leu Gln Leu Lys Val
65                  70                  75                  80

Gly Gly Gly Leu Thr Val Asp Asp Thr Asp Gly Thr Leu Gln Lys Asn
                85                  90                  95

Ile Arg Ala Thr Thr Pro Ile Thr Lys Asn Asn His Ser Val Glu Leu
                100                 105                 110

Thr Ile Gly Asn Gly Leu Glu Thr Gln His Asn Lys Leu Cys Ala Lys
                115                 120                 125
```

```
Leu Gly Asn Gly Asn Leu Lys Phe Asn Asn Gly Asp Ile Cys Ile Lys
            130                 135                 140

Asp Ser Ile Asn Thr Leu Trp Thr Gly Ile Asn Pro Pro Asn Cys Gln
145                 150                 155                 160

Ile Val Glu Asn Thr Asn Thr Asn Asp Gly Lys Leu Thr Leu Val Leu
                165                 170                 175

Val Lys Asn Gly Gly Leu Val Asn Gly Tyr Val Ser Leu Val Gly Val
            180                 185                 190

Ser Asp Thr Val Asn Gln Met Phe Thr Gln Lys Thr Ala Asn Ile Gln
            195                 200                 205

Leu Arg Leu Tyr Phe Asp Ser Ser Gly Asn Leu Leu Thr Asp Glu Ser
    210                 215                 220

Asp Leu Lys Ile Pro Leu Lys Asn Lys Ser Ser Thr Ala Thr Ser Glu
225                 230                 235                 240

Thr Val Ala Ser Ser Lys Ala Phe Met Pro Ser Thr Thr Ala Tyr Pro
                245                 250                 255

Phe Asn Thr Thr Thr Arg Asp Ser Glu Asn Tyr Ile His Gly Ile Cys
            260                 265                 270

Tyr Tyr Met Thr Ser Tyr Asp Arg Ser Leu Phe Pro Leu Asn Ile Ser
        275                 280                 285

Ile Met Leu Asn Ser Arg Met Ile Ser Ser Asn Val Ala Tyr Ala Ile
    290                 295                 300

Gln Phe Glu Trp Asn Leu Asn Ala Ser Glu Ser Pro Glu Lys Gln His
305                 310                 315                 320

Met Thr Leu Thr Thr Ser Pro Phe Phe Phe Ser Tyr Ile Ile Glu Asp
                325                 330                 335

Asp Asn

<210> SEQ ID NO 29
<211> LENGTH: 338
<212> TYPE: PRT
<213> ORGANISM: Human Adenovirus 35 Fiber Protein

<400> SEQUENCE: 29

Ser Cys Ser Cys Pro Ser Ala Pro Thr Ile Phe Met Leu Leu Gln Met
1               5                   10                  15

Lys Arg Ala Arg Pro Ser Glu Asp Thr Phe Asn Pro Val Tyr Pro Tyr
            20                  25                  30

Glu Asp Glu Ser Thr Ser Gln His Pro Phe Ile Asn Pro Gly Phe Ile
        35                  40                  45

Ser Pro Asn Gly Phe Thr Gln Ser Pro Asp Gly Val Leu Thr Leu Lys
    50                  55                  60

Cys Leu Thr Pro Leu Thr Thr Thr Gly Gly Ser Leu Gln Leu Lys Val
65                  70                  75                  80

Gly Gly Gly Leu Thr Val Asp Asp Thr Asp Gly Thr Leu Gln Glu Asn
            85                  90                  95

Ile Arg Ala Thr Ala Pro Ile Thr Lys Asn Asn His Ser Val Glu Leu
            100                 105                 110

Ser Ile Gly Asn Gly Leu Glu Thr Gln Asn Asn Lys Leu Cys Ala Lys
        115                 120                 125

Leu Gly Asn Gly Leu Lys Phe Asn Asn Gly Asp Ile Cys Ile Lys Asp
    130                 135                 140

Ser Ile Asn Thr Leu Trp Thr Gly Ile Asn Pro Pro Asn Cys Gln
145                 150                 155                 160
```

```
Ile Val Glu Asn Thr Asn Thr Asn Asp Gly Lys Leu Thr Leu Val Leu
                165                 170                 175

Val Lys Asn Gly Gly Leu Val Asn Gly Tyr Val Ser Leu Val Gly Val
            180                 185                 190

Ser Asp Thr Val Asn Gln Met Phe Thr Gln Lys Thr Ala Asn Ile Gln
        195                 200                 205

Leu Arg Leu Tyr Phe Asp Ser Ser Gly Asn Leu Leu Thr Glu Glu Ser
    210                 215                 220

Asp Leu Lys Ile Pro Leu Lys Asn Lys Ser Ser Thr Ala Thr Ser Glu
225                 230                 235                 240

Thr Val Ala Ser Ser Lys Ala Phe Met Pro Ser Thr Thr Ala Tyr Pro
                245                 250                 255

Phe Asn Thr Thr Thr Arg Asp Ser Glu Asn Tyr Ile His Gly Ile Cys
            260                 265                 270

Tyr Tyr Met Thr Ser Tyr Asp Arg Ser Leu Phe Pro Leu Asn Ile Ser
        275                 280                 285

Ile Met Leu Asn Ser Arg Met Ile Ser Ser Asn Val Ala Tyr Ala Ile
    290                 295                 300

Gln Phe Glu Trp Asn Leu Asn Ala Ser Glu Ser Pro Glu Ser Asn Ile
305                 310                 315                 320

Met Thr Leu Thr Thr Ser Pro Phe Phe Phe Ser Tyr Ile Thr Glu Asp
                325                 330                 335

Asp Asn

<210> SEQ ID NO 30
<211> LENGTH: 391
<212> TYPE: PRT
<213> ORGANISM: Human Adenovirus 36 Fiber Protein

<400> SEQUENCE: 30

Ser Cys Ser Cys Pro Ser Ala Pro Thr Ile Phe Met Leu Leu Gln Met
1               5                   10                  15

Lys Arg Ala Arg Pro Ser Glu Asp Thr Phe Asn Pro Val Tyr Pro Tyr
            20                  25                  30

Gly Tyr Ala Arg Asn Gln Asn Ile Pro Phe Leu Thr Pro Pro Phe Val
        35                  40                  45

Ser Ser Asp Gly Phe Lys Asn Phe Pro Pro Gly Val Leu Ser Leu Lys
    50                  55                  60

Leu Ala Asp Pro Ile Ala Ile Val Asn Gly Asp Val Ser Leu Lys Val
65                  70                  75                  80

Gly Gly Gly Leu Thr Val Glu Gln Asp Ser Gly Lys Leu Lys Val Asn
                85                  90                  95

Pro Lys Ile Pro Leu Gln Val Val Asn Lys Gln Leu Glu Leu Ala Thr
            100                 105                 110

Asp Lys Pro Phe Lys Ile Glu Asn Asn Lys Leu Ala Leu Asp Val Gly
        115                 120                 125

His Gly Leu Lys Val Ile Asp Lys Thr Ile Ser Asp Leu Gln Gly Leu
    130                 135                 140

Val Gly Lys Leu Val Val Leu Thr Gly Val Gly Ile Gly Thr Glu Thr
145                 150                 155                 160

Leu Lys Asp Lys Asn Asp Lys Val Ile Gly Ser Ala Val Asn Val Arg
                165                 170                 175

Leu Gly Lys Asp Gly Gly Leu Asp Phe Asn Lys Lys Gly Asp Leu Val
            180                 185                 190
```

-continued

```
Ala Trp Asn Arg Tyr Asp Asp Arg Arg Thr Leu Trp Thr Thr Pro Asp
        195                 200                 205

Pro Ser Pro Asn Cys Lys Val Tyr Glu Ala Lys Ser Lys Leu Thr Leu
210                 215                 220

Val Leu Thr Lys Cys Gly Ser Gln Ile Leu Ala Ser Val Ala Leu Leu
225                 230                 235                 240

Ile Val Lys Gly Lys Tyr Gln Thr Ile Ser Glu Ser Thr Ile Pro Lys
                245                 250                 255

Asp Gln Arg Asn Phe Ser Val Lys Leu Met Phe Asp Glu Lys Gly Lys
            260                 265                 270

Leu Leu Asp Lys Ser Ser Leu Asp Lys Glu Tyr Trp Asn Phe Arg Ser
        275                 280                 285

Asn Asp Ser Val Val Gly Thr Ala Tyr Asp Asn Ala Val Pro Phe Met
    290                 295                 300

Pro Asn Leu Lys Ala Tyr Pro Lys Asn Thr Thr Thr Ser Ser Thr Asn
305                 310                 315                 320

Pro Asp Asp Lys Ile Ser Ala Gly Lys Lys Asn Ile Val Ser Asn Val
                325                 330                 335

Tyr Leu Glu Gly Arg Val Tyr Gln Pro Val Ala Leu Thr Val Lys Phe
            340                 345                 350

Asn Ser Glu Asn Asp Cys Ala Tyr Ser Ile Thr Phe Asp Phe Val Trp
        355                 360                 365

Ser Lys Thr Tyr Glu Ser Pro Val Ala Phe Asp Ser Ser Phe Thr
    370                 375                 380

Phe Ser Tyr Ile Ala Gln Glu
385                 390

<210> SEQ ID NO 31
<211> LENGTH: 381
<212> TYPE: PRT
<213> ORGANISM: Human Adenovirus 37 Fiber Protein

<400> SEQUENCE: 31

Ser Cys Ser Cys Pro Ser Ala Pro Thr Ile Phe Met Leu Leu Gln Met
1               5                   10                  15

Lys Arg Ala Arg Pro Ser Glu Asp Thr Phe Asn Pro Val Tyr Pro Tyr
            20                  25                  30

Gly Tyr Ala Arg Asn Gln Asn Ile Pro Phe Leu Thr Pro Pro Phe Val
        35                  40                  45

Ser Ser Asp Gly Phe Lys Asn Phe Pro Pro Gly Val Leu Ser Leu Lys
    50                  55                  60

Leu Ala Asp Pro Ile Thr Ile Thr Asn Gly Asp Val Ser Leu Lys Val
65                  70                  75                  80

Gly Gly Gly Leu Thr Leu Gln Asp Gly Ser Leu Thr Val Asn Pro Lys
                85                  90                  95

Ala Pro Leu Gln Val Asn Thr Asp Lys Lys Leu Glu Leu Ala Tyr Asp
            100                 105                 110

Asn Pro Phe Glu Ser Ser Ala Asn Lys Leu Ser Leu Val Gly His Gly
        115                 120                 125

Leu Lys Val Leu Asp Glu Lys Ser Ala Ala Gly Leu Lys Asp Leu Ile
    130                 135                 140

Gly Lys Leu Val Val Leu Thr Gly Lys Gly Ile Gly Thr Glu Asn Leu
145                 150                 155                 160

Glu Asn Thr Asp Gly Ser Arg Gly Ile Gly Ile Asn Val Arg Ala
                165                 170                 175
```

```
Arg Glu Gly Leu Thr Phe Asp Asn Asp Gly Tyr Leu Val Ala Trp Asn
            180                 185                 190

Pro Lys Tyr Asp Leu Arg Thr Leu Trp Thr Thr Pro Asp Thr Ser Pro
        195                 200                 205

Asn Cys Thr Ile Ala Gln Asp Lys Asp Ser Lys Leu Thr Leu Val Leu
        210                 215                 220

Thr Lys Cys Gly Ser Gln Ile Leu Ala Asn Val Ser Leu Ile Val Val
225                 230                 235                 240

Ala Gly Lys Tyr His Ile Ile Asn Asn Lys Thr Asn Pro Lys Ile Lys
                245                 250                 255

Ser Phe Thr Ile Lys Leu Leu Phe Asn Lys Phe Asn Gly Val Leu Leu
                260                 265                 270

Asp Asn Ser Asn Leu Gly Lys Ala Tyr Trp Asn Phe Arg Ser Gly Asn
                275                 280                 285

Ser Asn Val Ser Thr Ala Tyr Glu Lys Ala Ile Gly Phe Met Pro Asn
        290                 295                 300

Leu Val Ala Val Ser Lys Pro Ser Asn Ser Lys Lys Tyr Ala Arg Asp
305                 310                 315                 320

Ile Val Tyr Gly Asn Ile Thr Tyr Leu Gly Gly Lys Pro Asp Gln Pro
                325                 330                 335

Gly Val Ile Lys Thr Thr Phe Asn Gln Glu Thr Gly Cys Glu Tyr Ser
                340                 345                 350

Ile Thr Phe Asn Phe Ser Trp Ser Lys Thr Tyr Glu Asn Val Glu Phe
                355                 360                 365

Glu Thr Thr Ser Phe Thr Phe Ser Tyr Ile Ala Gln Glu
        370                 375                 380

<210> SEQ ID NO 32
<211> LENGTH: 391
<212> TYPE: PRT
<213> ORGANISM: Human Adenovirus 38 Fiber Protein
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (49)..(192)
<223> OTHER INFORMATION: Xaa can be any amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (192)..(192)
<223> OTHER INFORMATION: Xaa can be any naturally occurring amino acid

<400> SEQUENCE: 32

Ser Cys Ser Cys Pro Ser Ala Pro Thr Ile Phe Met Leu Leu Gln Met
1               5                   10                  15

Lys Arg Ala Arg Pro Ser Glu Asp Thr Phe Asn Pro Val Tyr Pro Tyr
            20                  25                  30

Gly Tyr Ala Arg Asn Gln Asn Ile Pro Phe Xaa Thr Pro Pro Phe Val
        35                  40                  45

Xaa Ser Asp Gly Phe Gln Asn Phe Pro Pro Gly Val Leu Ser Leu Lys
50                  55                  60
```

```
Leu Ala Asp Pro Ile Thr Ile Ala Asn Gly Asn Val Ser Leu Lys Val
 65                  70                  75                  80

Gly Gly Gly Leu Thr Leu Glu Gln Asp Ser Gly Lys Leu Ile Val Asn
                 85                  90                  95

Xaa Lys Ala Pro Leu Gln Val Ala Asn Asp Lys Leu Glu Leu Ser Tyr
            100                 105                 110

Ala Asp Pro Phe Glu Thr Ser Ala Asn Lys Leu Ser Leu Lys Val Gly
        115                 120                 125

His Gly Leu Lys Val Leu Asp Glu Lys Asn Ala Gly Gly Leu Lys Asp
    130                 135                 140

Leu Ile Gly Thr Leu Val Val Leu Thr Gly Lys Gly Ile Gly Val Glu
145                 150                 155                 160

Glu Leu Lys Asn Ala Asp Asn Thr Asn Arg Gly Val Gly Ile Asn Val
                165                 170                 175

Arg Leu Gly Lys Asp Gly Gly Leu Ser Phe Asp Lys Lys Gly Asp Xaa
            180                 185                 190

Val Ala Trp Asn Lys His Asp Asp Arg Arg Thr Leu Trp Thr Thr Pro
        195                 200                 205

Asp Pro Ser Pro Asn Cys Thr Ile Asp Glu Glu Arg Asp Ser Lys Leu
    210                 215                 220

Thr Leu Val Leu Thr Lys Cys Gly Ser Gln Ile Leu Ala Asn Val Ser
225                 230                 235                 240

Leu Leu Val Val Lys Gly Lys Phe Ser Asn Ile Asn Asn Asn Thr Asn
                245                 250                 255

Pro Thr Asp Lys Lys Ile Thr Val Lys Leu Leu Phe Asn Glu Lys Gly
            260                 265                 270

Val Leu Met Asp Ser Ser Leu Lys Lys Glu Tyr Trp Asn Tyr Arg
        275                 280                 285

Asn Asp Asn Ser Thr Val Ser Gln Ala Tyr Asp Asn Ala Val Pro Phe
    290                 295                 300

Met Pro Asn Ile Lys Ala Tyr Pro Lys Pro Thr Thr Asp Thr Ser Ala
305                 310                 315                 320

Lys Pro Glu Asp Lys Lys Ser Ala Ala Lys Arg Tyr Thr Val Ser Asn
                325                 330                 335

Val Tyr Ile Gly Gly Leu Pro Asp Lys Thr Val Val Ile Thr Ile Lys
            340                 345                 350

Leu Asn Ala Glu Thr Glu Ser Ala Tyr Ser Met Thr Phe Glu Phe Thr
        355                 360                 365

Trp Ala Lys Thr Phe Glu Asn Leu Gln Phe Asp Ser Ser Phe Thr
    370                 375                 380

Phe Ser Tyr Ile Ala Gln Glu
385                 390

<210> SEQ ID NO 33
<211> LENGTH: 338
<212> TYPE: PRT
<213> ORGANISM: Human Adenovirus 39 Fiber Protein

<400> SEQUENCE: 33

Ile Arg Ile Ser Pro Ser Ser Leu Pro Pro Leu Ser Pro Met Asp
 1               5                  10                  15

Ser Lys Thr Ser Pro Leu Gly Cys Tyr His Ser Asn Trp Leu Thr Gln
                20                  25                  30

Ser Pro Ser Pro Met Gly Met Ser His Arg Trp Glu Gly Gly Ser Pro
```

```
                35                  40                  45
Trp Gln Glu Gly Thr Gly Asp Leu Lys Val Asn Ala Lys Ser Pro Leu
 50                  55                  60

Gln Val Ala Thr Asn Lys Gln Leu Glu Ile Ala Leu Ala Lys Pro Phe
 65                  70                  75                  80

Glu Glu Lys Asp Gly Lys Leu Ala Leu Lys Ile Gly His Gly Leu Ala
                 85                  90                  95

Val Val Asp Glu Asn His Thr His Leu Gln Ser Leu Ile Gly Thr Leu
                100                 105                 110

Val Ile Leu Thr Gly Lys Gly Ile Gly Thr Gly Arg Ala Glu Ser Gly
            115                 120                 125

Gly Thr Ile Asp Val Arg Leu Gly Ser Gly Gly Leu Ser Phe Asp
130                 135                 140

Lys Asp Gly Asn Leu Val Ala Trp Asn Lys Asp Asp Arg Arg Thr
145                 150                 155                 160

Leu Trp Thr Thr Pro Asp Pro Ser Pro Asn Cys Lys Ile Asp Gln Asp
                165                 170                 175

Lys Asp Ser Lys Leu Thr Phe Val Leu Thr Lys Cys Gly Ser Gln Ile
            180                 185                 190

Leu Ala Asn Met Ser Leu Leu Val Val Lys Gly Lys Phe Ser Met Ile
        195                 200                 205

Asn Asn Lys Val Asn Gly Thr Asp Asp Tyr Lys Lys Phe Thr Ile Lys
    210                 215                 220

Leu Leu Phe Asp Glu Lys Gly Val Leu Lys Asp Ser Ser Leu Asp
225                 230                 235                 240

Lys Glu Tyr Trp Asn Tyr Arg Ser Asn Asn Asn Val Gly Ser Ala
                245                 250                 255

Tyr Glu Glu Ala Val Gly Phe Met Pro Ser Thr Thr Ala Tyr Pro Lys
            260                 265                 270

Pro Pro Thr Pro Pro Thr Asn Pro Thr Pro Leu Glu Lys Ser Gln
                275                 280                 285

Ala Lys Asn Lys Tyr Val Ser Asn Val Tyr Leu Gly Gly Gln Ala Gly
290                 295                 300

Asn Pro Val Ala Thr Thr Val Ser Phe Asn Lys Glu Thr Gly Cys Thr
305                 310                 315                 320

Tyr Ser Ile Thr Phe Asp Phe Ala Trp Asn Lys Thr Tyr Glu Asn Val
                325                 330                 335

Gln Cys

<210> SEQ ID NO 34
<211> LENGTH: 378
<212> TYPE: PRT
<213> ORGANISM: Human Adenovirus 42 Fiber Protein
<220> FEATURE:
<221> NAME/KEY: misc_feature
<222> LOCATION: (237)..(237)
<223> OTHER INFORMATION: Xaa can be any amino acid
<220> FEATURE:
<221> NAME/KEY: misc_feature
<222> LOCATION: (237)..(237)
<223> OTHER INFORMATION: Xaa can be any naturally occurring amino acid

<400> SEQUENCE: 34

Ser Cys Ser Cys Pro Ser Ala Pro Thr Ile Phe Met Leu Leu Gln Met
1               5                  10                  15

Lys Arg Ala Arg Pro Ser Glu Asp Thr Phe Asn Pro Val Tyr Pro Tyr
                20                  25                  30
```

Gly Tyr Ala Arg Asn Gln Asn Ile Pro Phe Leu Thr Pro Pro Phe Val
                35                  40                  45

Ser Ser Asp Gly Phe Lys Asn Phe Pro Pro Gly Val Leu Ser Leu Lys
 50                  55                  60

Leu Ala Asn Pro Ile Ala Ile Thr Asn Gly Asp Val Ser Leu Lys Val
 65                  70                  75                  80

Gly Gly Gly Leu Thr Leu Gln Asp Gly Thr Gly Lys Leu Thr Ile Asp
                 85                  90                  95

Thr Lys Thr Pro Leu Gln Val Ala Asn Asn Lys Leu Glu Leu Ala Phe
                100                 105                 110

Asp Ala Pro Leu Tyr Glu Lys Asn Gly Lys Leu Ala Leu Lys Thr Gly
                115                 120                 125

His Gly Leu Ala Val Leu Thr Lys Asp Ile Gly Ile Pro Glu Leu Ile
            130                 135                 140

Gly Ser Leu Val Ile Leu Thr Gly Lys Gly Ile Gly Thr Gly Thr Val
145                 150                 155                 160

Ala Gly Gly Gly Thr Ile Asp Val Arg Leu Gly Asp Asp Gly Gly Leu
                165                 170                 175

Ser Phe Asp Lys Lys Gly Asp Leu Val Ala Trp Asn Lys Lys Asn Asp
                180                 185                 190

Arg Arg Thr Leu Trp Thr Thr Pro Asp Pro Ser Pro Asn Cys Arg Val
            195                 200                 205

Ser Glu Asp Lys Asp Ser Lys Leu Thr Leu Ile Leu Thr Lys Cys Gly
210                 215                 220

Ser Gln Ile Leu Ala Ser Phe Ser Leu Leu Val Val Xaa Gly Thr Tyr
225                 230                 235                 240

Thr Thr Val Asp Lys Asn Thr Asn Lys Gln Phe Ser Ile Lys Leu
                245                 250                 255

Leu Phe Asp Ala Asn Gly Lys Leu Lys Ser Glu Ser Asn Leu Ser Gln
                260                 265                 270

Tyr Trp Asn Tyr Arg Ser Asp Asn Ser Val Val Ser Thr Pro Tyr Asp
            275                 280                 285

Asn Ala Val Pro Phe Met Pro Asn Thr Ala Tyr Pro Lys Ile Ile Asn
290                 295                 300

Ser Thr Thr Asp Pro Glu Asn Lys Lys Ser Ala Lys Lys Thr Ile Val
305                 310                 315                 320

Gly Asn Val Tyr Leu Glu Gly Asn Ala Gly Gln Pro Val Ala Val Ala
                325                 330                 335

Ile Ser Phe Asn Lys Glu Thr Thr Ala Asp Tyr Ser Ile Thr Phe Asp
                340                 345                 350

Phe Ala Trp Ser Lys Ala Tyr Glu Thr Pro Val Pro Phe Asp Thr Ser
            355                 360                 365

Ser Met Thr Phe Ser Tyr Ile Ala Gln Glu
        370                 375

<210> SEQ ID NO 35
<211> LENGTH: 328
<212> TYPE: PRT
<213> ORGANISM: Human Adenovirus 43 Fiber Protein
<220> FEATURE:
<221> NAME/KEY: misc_feature
<222> LOCATION: (4)..(233)
<223> OTHER INFORMATION: Xaa Can be any amino acid
<220> FEATURE:
<221> NAME/KEY: misc_feature
<222> LOCATION: (4)..(4)

<223> OTHER INFORMATION: Xaa can be any naturally occurring amino acid
<220> FEATURE:
<221> NAME/KEY: misc_feature
<222> LOCATION: (232)..(233)
<223> OTHER INFORMATION: Xaa can be any naturally occurring amino acid

<400> SEQUENCE: 35

```
Asn Ile Pro Xaa Leu Thr Pro Pro Phe Val Ser Ser Asp Gly Phe Lys
1               5                   10                  15

Asn Phe Pro Pro Gly Val Leu Ser Leu Lys Leu Ala Asp Pro Ile Thr
            20                  25                  30

Ile Thr Asn Gly Asp Val Ser Leu Lys Val Gly Gly Leu Thr Val
        35                  40                  45

Glu Lys Glu Ser Gly Asn Leu Thr Val Asn Pro Lys Ala Pro Leu Gln
50                  55                  60

Val Ala Lys Gly Gln Leu Glu Leu Ala Tyr Asp Ser Pro Phe Asp Val
65                  70                  75                  80

Lys Asn Asn Met Leu Thr Leu Lys Ala Gly His Gly Leu Ala Val Val
                85                  90                  95

Thr Lys Asp Asn Thr Asp Leu Gln Pro Leu Met Gly Thr Leu Val Val
            100                 105                 110

Leu Thr Gly Lys Gly Ile Gly Thr Gly Thr Ser Ala His Gly Gly Thr
        115                 120                 125

Ile Asp Val Arg Ile Gly Lys Asn Gly Ser Leu Ala Phe Asp Lys Asp
130                 135                 140

Gly Asp Leu Val Ala Trp Asp Lys Glu Asn Asp Arg Arg Thr Leu Trp
145                 150                 155                 160

Thr Thr Pro Asp Thr Ser Pro Asn Cys Lys Met Ser Glu Ala Lys Asp
                165                 170                 175

Ser Lys Leu Thr Leu Ile Leu Thr Lys Cys Gly Ser Gln Ile Leu Gly
            180                 185                 190

Ser Val Ser Leu Leu Ala Val Lys Gly Glu Tyr Gln Asn Met Thr Ala
        195                 200                 205

Asn Thr Lys Lys Asn Val Lys Ile Thr Leu Leu Phe Asp Ala Asn Gly
210                 215                 220

Val Leu Leu Ala Gly Ser Ser Xaa Xaa Lys Glu Tyr Trp Asn Phe Arg
225                 230                 235                 240

Ser Asn Asp Ser Thr Val Ser Gly Asn Tyr Glu Asn Ala Val Gln Phe
                245                 250                 255

Met Pro Asn Ile Thr Ala Tyr Lys Pro Thr Asn Ser Lys Ser Tyr Ala
            260                 265                 270

Arg Ser Val Ile Phe Gly Asn Val Tyr Ile Asp Ala Lys Pro Tyr Asn
        275                 280                 285

Pro Val Val Ile Lys Ile Ser Phe Asn Gln Glu Thr Gln Asn Asn Cys
290                 295                 300

Val Tyr Ser Ile Ser Phe Asp Tyr Thr Leu Ser Lys Asp Tyr Pro Asn
305                 310                 315                 320

Met Gln Phe Asp Val Thr Leu Ser
                325
```

<210> SEQ ID NO 36
<211> LENGTH: 341
<212> TYPE: PRT
<213> ORGANISM: Human Adenovirus 44 Fiber Protein

<400> SEQUENCE: 36

```
Asn Ile Pro Phe Leu Thr Pro Pro Phe Val Ser Ser Asp Gly Phe Gln
1               5                   10                  15

Asn Phe Pro Pro Gly Val Leu Ser Leu Lys Leu Ala Asp Pro Ile Thr
            20                  25                  30

Ile Thr Asn Gly Asn Val Ser Leu Lys Val Gly Gly Gly Leu Thr Leu
        35                  40                  45

Gln Glu Gly Thr Gly Asp Leu Lys Val Asn Ala Lys Ser Pro Leu Gln
50                  55                  60

Val Ala Thr Asn Lys Gln Leu Glu Ile Ala Leu Ala Lys Pro Phe Glu
65                  70                  75                  80

Glu Lys Asp Gly Lys Leu Ala Leu Lys Ile Gly His Gly Leu Ala Val
                85                  90                  95

Val Asp Glu Asn His Thr His Leu Gln Ser Leu Ile Gly Thr Leu Val
                100                 105                 110

Ile Leu Thr Gly Lys Gly Ile Gly Thr Gly Ser Ala Glu Ser Gly Gly
            115                 120                 125

Thr Ile Asp Val Arg Leu Gly Ser Gly Gly Leu Ser Phe Asp Lys
130                 135                 140

Asp Gly Asn Leu Val Ala Trp Asn Lys Asp Asp Arg Arg Thr Leu
145                 150                 155                 160

Trp Thr Thr Pro Asp Pro Ser Pro Asn Cys Lys Ile Asp Gln Asp Lys
                165                 170                 175

Asp Ser Lys Leu Thr Phe Val Leu Thr Lys Cys Gly Ser Gln Ile Leu
            180                 185                 190

Ala Asn Met Ser Leu Leu Val Val Lys Gly Lys Phe Ser Met Ile Asn
        195                 200                 205

Asn Lys Val Asn Gly Thr Asp Asp Tyr Lys Lys Phe Thr Ile Lys Leu
210                 215                 220

Leu Phe Asp Glu Lys Gly Val Leu Leu Lys Asp Ser Ser Leu Asp Lys
225                 230                 235                 240

Glu Tyr Trp Asn Tyr Arg Ser Asn Asn Asn Val Gly Ser Ala Tyr
                245                 250                 255

Glu Glu Ala Val Gly Phe Met Pro Ser Thr Thr Ala Tyr Pro Lys Pro
                260                 265                 270

Pro Thr Pro Thr Asn Pro Thr Thr Pro Leu Glu Lys Ser Gln Ala
            275                 280                 285

Lys Asn Lys Tyr Val Ser Asn Val Tyr Leu Gly Gly Gln Ala Gly Asn
290                 295                 300

Pro Val Ala Thr Thr Val Ser Phe Asn Lys Glu Thr Gly Cys Thr Tyr
305                 310                 315                 320

Ser Ile Thr Phe Asp Phe Ala Trp Asn Lys Thr Tyr Glu Asn Val Gln
                325                 330                 335

Phe Asp Ser Ser Phe
            340

<210> SEQ ID NO 37
<211> LENGTH: 345
<212> TYPE: PRT
<213> ORGANISM: Human Adenovirus 45 Fiber Protein

<400> SEQUENCE: 37

Asn Ile Pro Phe Leu Thr Pro Pro Phe Val Ser Ser Asp Gly Phe Gln
1               5                   10                  15

Asn Phe Pro Pro Gly Val Leu Ser Leu Lys Leu Ala Asp Pro Ile Ala
            20                  25                  30
```

```
Ile Thr Asn Gly Asp Val Ser Leu Lys Val Gly Gly Leu Thr Val
            35                  40                  45

Glu Lys Asp Ser Gly Asn Leu Lys Val Asn Pro Lys Ala Pro Leu Gln
 50                  55                  60

Val Thr Thr Asp Lys Gln Leu Glu Ile Ala Leu Ala Tyr Pro Phe Glu
 65                  70                  75                  80

Val Ser Asn Gly Lys Leu Gly Ile Lys Ala Gly His Gly Leu Lys Val
                 85                  90                  95

Ile Asp Lys Ile Ala Gly Leu Glu Gly Leu Ala Gly Thr Leu Val Val
            100                 105                 110

Leu Thr Gly Lys Gly Ile Gly Thr Glu Asn Leu Glu Asn Ser Asp Gly
            115                 120                 125

Ser Ser Arg Gly Val Gly Ile Asn Val Arg Leu Ala Lys Asp Gly Val
            130                 135                 140

Leu Ala Phe Asp Lys Lys Gly Asp Leu Val Ala Trp Asn Lys His Asp
145                 150                 155                 160

Asp Arg Arg Thr Leu Trp Thr Thr Pro Asp Pro Ser Pro Asn Cys Thr
                165                 170                 175

Ile Asp Gln Glu Arg Asp Ser Lys Leu Thr Leu Val Leu Thr Lys Cys
            180                 185                 190

Gly Ser Gln Ile Leu Ala Asn Val Ser Leu Leu Val Val Lys Gly Lys
            195                 200                 205

Phe Ser Asn Ile Asn Asn Asn Ala Asn Pro Thr Asp Lys Lys Ile Thr
210                 215                 220

Val Lys Leu Leu Phe Asn Glu Lys Gly Val Leu Met Asp Ser Ser Thr
225                 230                 235                 240

Leu Lys Lys Glu Tyr Trp Asn Tyr Arg Asn Asp Asn Ser Thr Val Ser
                245                 250                 255

Gln Ala Tyr Asp Asn Ala Val Pro Phe Met Pro Asn Ile Lys Ala Tyr
            260                 265                 270

Pro Lys Pro Ser Thr Asp Thr Ser Ala Lys Pro Glu Asp Lys Lys Ser
            275                 280                 285

Ala Ala Lys Arg Tyr Ile Val Ser Asn Val Tyr Ile Gly Gly Leu Pro
            290                 295                 300

Asp Lys Thr Val Val Ile Thr Ile Lys Phe Asn Ala Glu Thr Glu Cys
305                 310                 315                 320

Ala Tyr Ser Ile Thr Phe Glu Phe Thr Trp Ala Lys Thr Phe Glu Asp
                325                 330                 335

Val Gln Cys Asp Ser Ser Ser Phe Thr
            340                 345

<210> SEQ ID NO 38
<211> LENGTH: 339
<212> TYPE: PRT
<213> ORGANISM: Human Adenovirus 46 Fiber Protein

<400> SEQUENCE: 38

Asn Ile Pro Phe Leu Thr Pro Pro Phe Val Ser Ser Asp Gly Phe Lys
 1               5                  10                  15

Asn Phe Pro Pro Gly Val Leu Ser Leu Lys Leu Ala Asp Pro Ile Ala
                 20                  25                  30

Ile Val Asn Gly Asp Val Ser Leu Lys Val Gly Gly Leu Thr Leu
            35                  40                  45

Gln Glu Gly Asn Leu Thr Val Asp Ala Lys Ala Pro Leu Gln Val Ala
```

-continued

```
                50                  55                  60
Asn Asp Lys Leu Glu Leu Ser Tyr Ala Asp Phe Glu Val Lys Asp
 65                  70                  75                  80

Thr Lys Leu Gln Leu Lys Val Gly His Gly Leu Lys Val Ile Asp Glu
                 85                  90                  95

Lys Thr Ser Ser Gly Leu Gln Ser Leu Ile Gly Asn Leu Val Val Leu
                100                 105                 110

Thr Gly Lys Gly Ile Gly Thr Gln Glu Leu Lys Asp Lys Asp Asp Glu
                115                 120                 125

Thr Lys Asn Ile Gly Val Gly Ile Asn Val Arg Ile Gly Lys Asn Glu
                130                 135                 140

Ser Leu Ala Phe Asp Lys Asp Gly Asn Leu Val Ala Trp Asp Asn Glu
145                 150                 155                 160

Asn Asp Arg Arg Thr Leu Trp Thr Thr Pro Asp Thr Ser Ser Lys Phe
                165                 170                 175

Val Lys Ile Ser Thr Glu Lys Asp Ser Lys Leu Thr Leu Val Leu Thr
                180                 185                 190

Lys Cys Gly Ser Gln Ile Leu Ala Ser Val Ser Leu Leu Ala Val Ala
                195                 200                 205

Gly Ser Tyr Leu Asn Met Thr Ala Ser Thr Gln Lys Ser Ile Lys Val
                210                 215                 220

Ser Leu Met Phe Asp Ser Lys Gly Leu Leu Met Thr Thr Ser Ser Ile
225                 230                 235                 240

Asp Lys Gly Tyr Trp Asn Tyr Arg Asn Lys Asn Ser Val Val Gly Thr
                245                 250                 255

Ala Tyr Glu Asn Ala Ile Pro Phe Met Pro Asn Leu Val Ala Tyr Pro
                260                 265                 270

Arg Pro Asn Thr Pro Asp Ser Lys Ile Tyr Ala Arg Ser Lys Ile Val
                275                 280                 285

Gly Asn Val Tyr Leu Ala Gly Leu Ala Tyr Gln Pro Ile Val Ile Thr
                290                 295                 300

Val Ser Phe Asn Gln Glu Lys Asp Ala Ser Cys Ala Tyr Ser Ile Thr
305                 310                 315                 320

Phe Glu Phe Ala Trp Asn Lys Asp Tyr Val Gly Gln Phe Asp Thr Thr
                325                 330                 335

Ser Phe Thr

<210> SEQ ID NO 39
<211> LENGTH: 389
<212> TYPE: PRT
<213> ORGANISM: Human Adenovirus 47 Fiber Protein

<400> SEQUENCE: 39

Ser Cys Pro Ser Ala Pro Thr Ile Phe Met Leu Leu Gln Met Lys Arg
 1               5                  10                  15

Ala Arg Pro Ser Glu Asp Thr Phe Asn Pro Val Tyr Pro Tyr Gly Tyr
                20                  25                  30

Ala Arg Asn Gln Asn Ile Pro Phe Leu Thr Pro Pro Phe Val Ser Ser
                35                  40                  45

Asp Gly Phe Lys Asn Phe Pro Pro Gly Val Leu Ser Leu Lys Leu Ala
                50                  55                  60

Asp Pro Ile Thr Ile Thr Asn Gly Asp Val Ser Leu Lys Val Gly Gly
 65                  70                  75                  80

Gly Leu Thr Leu Gln Glu Gly Thr Gly Asn Leu Thr Val Asn Ala Lys
```

85                  90                  95
Ala Pro Leu Gln Val Ala Asp Asp Lys Lys Leu Glu Leu Ser Tyr Asp
                100                 105                 110

Asn Pro Phe Glu Val Ser Ala Asn Lys Leu Ser Leu Lys Val Gly His
            115                 120                 125

Gly Leu Lys Val Leu Asp Glu Lys Asn Ser Gly Gly Leu Gln Glu Leu
        130                 135                 140

Ile Gly Lys Leu Val Ile Leu Thr Gly Lys Gly Ile Gly Val Glu Glu
145                 150                 155                 160

Leu Lys Asn Ala Asp Asn Thr Asn Arg Gly Val Gly Ile Asn Val Arg
                165                 170                 175

Leu Gly Lys Asp Gly Gly Leu Ser Phe Asp Lys Lys Gly Glu Leu Val
            180                 185                 190

Ala Trp Asn Lys His Asn Asp Thr Arg Thr Leu Trp Thr Thr Pro Asp
        195                 200                 205

Pro Ser Pro Asn Cys Lys Ile Glu Gln Asp Lys Asp Ser Lys Leu Thr
210                 215                 220

Leu Val Leu Thr Lys Cys Gly Ser Gln Ile Leu Ala Thr Met Ala Phe
225                 230                 235                 240

Gln Val Val Lys Asp Thr Tyr Glu Asn Ile Ser Lys Asn Thr Ala Lys
                245                 250                 255

Lys Ser Phe Ser Ile Lys Leu Leu Phe Asp Asp Asn Gly Lys Leu Leu
            260                 265                 270

Glu Gly Ser Ser Leu Asp Lys Asp Tyr Trp Asn Phe Arg Asn Asp Asp
        275                 280                 285

Ser Ile Met Pro Ser Gln Tyr Asp Asn Ala Val Pro Phe Met Pro Asn
290                 295                 300

Leu Lys Ala Tyr Pro Asn Pro Lys Thr Ser Thr Val Leu Pro Ser Thr
305                 310                 315                 320

Asp Lys Lys Ser Asn Gly Lys Asn Thr Ile Val Ser Asn Leu Tyr Leu
                325                 330                 335

Glu Gly Lys Ala Tyr Gln Pro Val Ala Val Thr Ile Thr Phe Asn Lys
            340                 345                 350

Glu Tyr Gly Cys Thr Tyr Ser Ile Thr Phe Glu Phe Gly Trp Ala Lys
        355                 360                 365

Thr Tyr Asp Val Pro Ile Pro Phe Asp Ser Ser Ser Phe Thr Phe Ser
370                 375                 380

Tyr Ile Ala Gln Glu
385

<210> SEQ ID NO 40
<211> LENGTH: 343
<212> TYPE: PRT
<213> ORGANISM: Human Adenovirus 48 Fiber Protein

<400> SEQUENCE: 40

Ser Asp Ile Pro Phe Leu Thr Pro Pro Phe Val Ser Ser Asp Gly Phe
1               5                   10                  15

Gln Asn Phe Pro Pro Gly Val Leu Ser Leu Lys Leu Ala Asp Pro Ile
            20                  25                  30

Thr Ile Thr Asn Gly Asn Val Ser Leu Lys Val Gly Gly Gly Leu Thr
        35                  40                  45

Leu Gln Glu Gly Thr Gly Asp Leu Lys Val Asn Ala Lys Ser Pro Leu
    50                  55                  60

```
Gln Val Ala Thr Asn Lys Gln Leu Glu Ile Ala Leu Ala Lys Pro Phe
 65                  70                  75                  80

Glu Glu Lys Asp Gly Lys Leu Ala Leu Lys Ile Gly His Glu Leu Ala
                 85                  90                  95

Val Val Asp Glu Asn Leu Thr His Leu Gln Ser Leu Ile Gly Thr Leu
            100                 105                 110

Val Ile Leu Thr Gly Lys Gly Ile Gly Thr Gly Arg Ala Glu Ser Gly
        115                 120                 125

Gly Thr Ile Asp Val Arg Leu Gly Ser Gly Gly Leu Ser Phe Asp
    130                 135                 140

Lys Asp Gly Asn Leu Val Ala Trp Asn Lys Asp Asp Arg Arg Thr
145                 150                 155                 160

Leu Trp Thr Thr Pro Asp Pro Ser Pro Asn Cys Lys Ile Asp Gln Asp
                165                 170                 175

Lys Asp Ser Lys Leu Thr Phe Val Leu Thr Lys Cys Gly Ser Gln Ile
            180                 185                 190

Leu Ala Asn Met Ser Leu Leu Val Lys Gly Lys Phe Ser Met Ile
        195                 200                 205

Asn Asn Lys Val Asn Gly Thr Asp Asp Tyr Lys Lys Phe Thr Ile Lys
    210                 215                 220

Leu Leu Phe Asp Glu Lys Gly Val Leu Leu Lys Asp Ser Ser Leu Asp
225                 230                 235                 240

Lys Glu Tyr Trp Asn Tyr Arg Ser Asn Asn Asn Val Gly Ser Ala
                245                 250                 255

Tyr Glu Glu Ala Val Gly Phe Met Pro Ser Thr Thr Ala Tyr Pro Lys
            260                 265                 270

Pro Pro Thr Pro Pro Thr Asn Pro Thr Pro Leu Glu Lys Ser Gln
        275                 280                 285

Ala Lys Asn Lys Tyr Val Ser Asn Val Tyr Leu Gly Gly Gln Ala Gly
    290                 295                 300

Asn Pro Val Ala Thr Thr Val Ser Phe Asn Lys Glu Thr Gly Cys Thr
305                 310                 315                 320

Tyr Ser Ile Thr Phe Asp Phe Ala Trp Asn Lys Thr Tyr Lys Met Ala
                325                 330                 335

Phe Ile Pro Arg Phe Asn Phe
            340

<210> SEQ ID NO 41
<211> LENGTH: 393
<212> TYPE: PRT
<213> ORGANISM: Human Adenovirus 49 Fiber Protein
<220> FEATURE:
<221> NAME/KEY: misc_feature
<222> LOCATION: (262)..(262)
<223> OTHER INFORMATION: Xaa can be any nucleic acid
<220> FEATURE:
<221> NAME/KEY: misc_feature
<222> LOCATION: (262)..(262)
<223> OTHER INFORMATION: Xaa can be any naturally occurring amino acid

<400> SEQUENCE: 41

Ser Cys Ser Cys Pro Ser Ala Pro Thr Ile Phe Met Leu Leu Gln Met
 1               5                  10                  15

Lys Arg Ala Arg Pro Ser Glu Asp Thr Phe Asn Pro Val Tyr Pro Tyr
                 20                  25                  30

Gly Tyr Ala Arg Asn Gln Asn Ile Pro Phe Leu Thr Pro Pro Phe Val
         35                  40                  45
```

```
Ser Ser Asp Gly Phe Gln Asn Phe Pro Pro Gly Val Leu Ser Leu Lys
 50                  55                  60

Leu Ala Asp Pro Ile Ala Ile Thr Asn Gly Asn Val Ser Leu Lys Val
 65                  70                  75                  80

Gly Gly Gly Leu Thr Val Glu Gln Asp Ser Gly Asn Leu Lys Val Asn
                 85                  90                  95

Pro Lys Ala Pro Leu Gln Val Ala Thr Asp Asn Gln Leu Glu Ile Ser
                100                 105                 110

Leu Ala Asp Pro Phe Glu Val Lys Asn Lys Leu Ser Leu Lys Val
                115                 120                 125

Gly His Gly Leu Lys Val Ile Asp Glu Asn Ile Ser Thr Leu Gln Gly
        130                 135                 140

Leu Leu Gly Asn Leu Val Val Leu Thr Gly Met Gly Ile Gly Thr Glu
145                 150                 155                 160

Glu Leu Lys Lys Asp Asp Lys Ile Val Gly Ser Ala Val Asn Val Arg
                165                 170                 175

Leu Gly Gln Asp Gly Gly Leu Thr Phe Asp Lys Lys Gly Asp Leu Val
                180                 185                 190

Ala Trp Asn Lys Glu Asn Asp Arg Arg Thr Leu Trp Thr Thr Pro Asp
        195                 200                 205

Pro Ser Pro Asn Cys Lys Val Ser Glu Glu Lys Asp Ser Lys Leu Thr
210                 215                 220

Leu Val Leu Thr Lys Cys Gly Ser Gln Ile Leu Ala Ser Val Ser Leu
225                 230                 235                 240

Leu Val Val Lys Gly Lys Phe Ala Asn Ile Asn Asn Lys Thr Asn Pro
                245                 250                 255

Gly Glu Asp Tyr Lys Xaa Phe Ser Val Lys Leu Leu Phe Asp Ala Asn
                260                 265                 270

Gly Lys Leu Leu Thr Gly Ser Ser Leu Asp Gly Asn Tyr Trp Asn Tyr
        275                 280                 285

Lys Asn Lys Asp Ser Val Ile Gly Ser Pro Tyr Glu Asn Ala Val Pro
290                 295                 300

Phe Met Pro Asn Ser Thr Ala Tyr Pro Lys Ile Ile Asn Gly Thr Ala
305                 310                 315                 320

Asn Pro Glu Asp Lys Lys Ser Ala Ala Lys Lys Thr Ile Val Thr Asn
                325                 330                 335

Val Tyr Leu Gly Gly Asp Ala Ala Lys Pro Val Ala Thr Thr Ile Ser
                340                 345                 350

Phe Asn Lys Glu Thr Glu Ser Asn Cys Val Tyr Ser Ile Thr Phe Asp
        355                 360                 365

Phe Ala Trp Asn Lys Thr Trp Lys Asn Val Pro Phe Asp Ser Ser Ser
370                 375                 380

Leu Thr Phe Ser Tyr Ile Ala Gln Glu
385                 390

<210> SEQ ID NO 42
<211> LENGTH: 353
<212> TYPE: PRT
<213> ORGANISM: Human Adenovirus 52 Fiber Protein

<400> SEQUENCE: 42

Ser Cys Ser Cys Pro Ser Ala Pro Thr Ile Phe Met Leu Leu Gln Met
1               5                  10                  15

Lys Arg Ala Arg Pro Ser Glu Asp Thr Phe Asn Pro Val Tyr Pro Tyr
                20                  25                  30
```

```
Glu Asp Glu Ser Thr Ser Gln His Pro Phe Ile Asn Pro Gly Phe Ile
             35                  40                  45

Ser Pro Asn Gly Phe Thr Gln Ser Pro Asp Gly Val Leu Thr Leu Asn
         50                  55                  60

Cys Leu Thr Pro Leu Thr Thr Thr Gly Gly Pro Leu Gln Leu Lys Val
 65                  70                  75                  80

Gly Gly Gly Leu Ile Val Asp Asp Thr Asp Gly Thr Leu Gln Glu Asn
                     85                  90                  95

Ile Arg Val Thr Ala Pro Ile Thr Lys Asn Asn His Ser Val Glu Leu
                100                 105                 110

Ser Ile Gly Asn Gly Leu Glu Thr Gln Asn Asn Lys Leu Cys Ala Lys
            115                 120                 125

Leu Gly Asn Gly Leu Lys Phe Asn Asn Gly Asp Ile Cys Ile Lys Asp
        130                 135                 140

Ser Ile Asn Thr Leu Trp Thr Gly Ile Lys Pro Pro Pro Asn Cys Gln
145                 150                 155                 160

Ile Val Glu Asn Thr Asp Thr Asn Asp Gly Lys Leu Thr Leu Val Leu
                165                 170                 175

Val Lys Asn Gly Gly Leu Val Asn Gly Tyr Val Ser Leu Val Gly Val
                180                 185                 190

Ser Asp Thr Val Asn Gln Met Phe Thr Gln Lys Ser Ala Thr Ile Gln
            195                 200                 205

Leu Arg Leu Tyr Phe Asp Ser Ser Gly Asn Leu Leu Thr Asp Glu Ser
        210                 215                 220

Asn Leu Lys Ile Pro Leu Lys Asn Lys Ser Ser Thr Ala Thr Ser Glu
225                 230                 235                 240

Ala Ala Thr Ser Ser Lys Ala Phe Met Pro Ser Thr Thr Ala Tyr Pro
                245                 250                 255

Phe Asn Thr Thr Thr Arg Asp Ser Glu Asn Tyr Ile His Gly Ile Cys
                260                 265                 270

Tyr Tyr Met Thr Ser Tyr Asp Arg Ser Leu Val Pro Leu Asn Ile Ser
            275                 280                 285

Ile Met Leu Asn Ser Arg Thr Ile Ser Ser Asn Val Ala Tyr Ala Ile
        290                 295                 300

Gln Phe Glu Trp Asn Leu Asn Ala Lys Glu Ser Pro Glu Ser Asn Ile
305                 310                 315                 320

Ala Thr Leu Thr Thr Ser Pro Phe Phe Phe Ser Tyr Ile Ile Glu Asp
                325                 330                 335

Thr Thr Lys Cys Ile Ser Leu Cys Tyr Val Ser Thr Cys Leu Phe Phe
                340                 345                 350

Asn

<210> SEQ ID NO 43
<211> LENGTH: 958
<212> TYPE: PRT
<213> ORGANISM: Human Adenovirus 34 Hexon Protein

<400> SEQUENCE: 43

Leu Ser Arg Arg Ala Pro Gly Phe Pro Leu Val Lys Met Ala Thr Pro
1               5                   10                  15

Ser Met Leu Pro Gln Trp Ala Tyr Met His Ile Ala Gly Gln Asp Ala
            20                  25                  30

Ser Glu Tyr Leu Ser Pro Gly Leu Val Gln Phe Ala Arg Ala Thr Asp
        35                  40                  45
```

-continued

```
Thr Tyr Val Asn Leu Gly Asn Lys Phe Arg Asn Pro Thr Val Ala Pro
    50                  55                  60

Thr His Asp Val Thr Thr Asp Arg Ser Gln Arg Leu Met Leu Arg Phe
65                  70                  75                  80

Val Pro Val Asp Arg Glu Asp Asn Thr Tyr Ser Tyr Lys Val Arg Tyr
                85                  90                  95

Thr Leu Ala Val Gly Asp Asn Arg Val Leu Asp Met Ala Ser Thr Phe
                100                 105                 110

Phe Asp Ile Arg Gly Val Leu Asp Arg Gly Pro Ser Phe Lys Pro Tyr
            115                 120                 125

Ser Gly Thr Ala Tyr Asn Ser Leu Ala Pro Lys Gly Ala Pro Asn Ala
    130                 135                 140

Ser Gln Trp Leu Asp Lys Gly Val Thr Ser Thr Gly Leu Val Asp Asp
145                 150                 155                 160

Gly Asn Thr Thr Asp Asp Gly Glu Glu Ala Lys Lys Ala Thr Tyr Thr
                165                 170                 175

Phe Gly Asn Ala Pro Val Lys Ala Glu Ala Glu Ile Thr Lys Asp Gly
                180                 185                 190

Leu Pro Val Gly Leu Glu Val Ser Thr Glu Gly Pro Lys Pro Ile Tyr
        195                 200                 205

Ala Asp Lys Leu Tyr Gln Pro Glu Pro Gln Val Gly Asp Glu Thr Trp
    210                 215                 220

Thr Asp Leu Asp Gly Lys Thr Glu Glu Tyr Gly Gly Arg Val Leu Lys
225                 230                 235                 240

Pro Glu Thr Lys Met Lys Pro Cys Tyr Gly Ser Phe Ala Lys Pro Thr
                245                 250                 255

Asn Ile Lys Gly Gly Gln Ala Lys Val Lys Pro Lys Glu Asp Asp Gly
                260                 265                 270

Thr Asn Asn Ile Glu Tyr Asp Ile Asp Met Asn Phe Phe Asp Leu Arg
        275                 280                 285

Ser Gln Arg Ser Glu Leu Lys Pro Lys Ile Val Met Tyr Ala Glu Asn
    290                 295                 300

Val Asp Leu Glu Cys Pro Asp Thr His Val Val Tyr Lys Pro Gly Val
305                 310                 315                 320

Ser Asp Ala Ser Ser Glu Thr Asn Leu Gly Gln Gln Ser Met Pro Asn
                325                 330                 335

Arg Pro Asn Tyr Ile Gly Phe Arg Asp Asn Phe Ile Gly Leu Met Tyr
                340                 345                 350

Tyr Asn Ser Thr Gly Asn Met Gly Val Leu Ala Gly Gln Ala Ser Gln
        355                 360                 365

Leu Asn Ala Val Val Asp Leu Gln Asp Arg Asn Thr Glu Leu Ser Tyr
    370                 375                 380

Gln Leu Leu Asp Ser Leu Gly Asp Arg Thr Arg Tyr Phe Ser Met Trp
385                 390                 395                 400

Asn Gln Ala Val Asp Ser Tyr Asp Pro Asp Val Arg Val Ile Glu Asn
                405                 410                 415

His Gly Val Glu Asp Glu Leu Pro Asn Tyr Cys Phe Pro Leu Asp Gly
                420                 425                 430

Val Gly Pro Arg Thr Asp Ser Tyr Lys Glu Ile Lys Pro Asn Gly Asp
        435                 440                 445

Gln Ser Thr Trp Thr Asn Val Asp Pro Thr Gly Ser Ser Glu Leu Ala
    450                 455                 460
```

-continued

```
Lys Gly Asn Pro Phe Ala Met Glu Ile Asn Leu Gln Ala Asn Leu Trp
465                 470                 475                 480

Arg Ser Phe Leu Tyr Ser Asn Val Ala Leu Tyr Leu Pro Asp Ser Tyr
                485                 490                 495

Lys Tyr Thr Pro Ser Asn Val Thr Leu Pro Glu Asn Lys Asn Thr Tyr
            500                 505                 510

Asp Tyr Met Asn Gly Arg Val Val Pro Pro Ser Leu Val Asp Thr Tyr
        515                 520                 525

Val Asn Ile Gly Ala Arg Trp Ser Leu Asp Ala Met Asp Asn Val Asn
    530                 535                 540

Pro Phe Asn His His Arg Asn Ala Gly Leu Arg Tyr Arg Ser Met Leu
545                 550                 555                 560

Leu Gly Asn Gly Arg Tyr Val Pro Phe His Ile Gln Val Pro Gln Lys
                565                 570                 575

Phe Phe Ala Val Lys Asn Leu Leu Leu Pro Gly Ser Tyr Thr Tyr
            580                 585                 590

Glu Trp Asn Phe Arg Lys Asp Val Asn Met Val Leu Gln Ser Ser Leu
        595                 600                 605

Gly Asn Asp Leu Arg Val Asp Gly Ala Ser Ile Ser Phe Thr Ser Ile
    610                 615                 620

Asn Leu Tyr Ala Thr Phe Phe Pro Met Ala His Asn Thr Ala Ser Thr
625                 630                 635                 640

Leu Glu Ala Met Leu Arg Asn Asp Thr Asn Asp Gln Ser Phe Asn Asp
                645                 650                 655

Tyr Leu Ser Ala Ala Asn Met Leu Tyr Pro Ile Pro Ala Asn Ala Thr
            660                 665                 670

Asn Ile Pro Ile Ser Ile Pro Ser Arg Asn Trp Ala Ala Phe Arg Gly
        675                 680                 685

Trp Ser Phe Thr Arg Leu Lys Thr Lys Glu Thr Pro Ser Leu Gly Ser
    690                 695                 700

Gly Phe Asp Pro Tyr Phe Val Tyr Ser Gly Ser Ile Pro Leu Asp Gly
705                 710                 715                 720

Thr Phe Tyr Leu Asn His Thr Phe Lys Lys Val Ser Ile Met Phe Asp
                725                 730                 735

Ser Ser Val Ser Trp Pro Gly Asn Asp Arg Leu Leu Ser Pro Asn Glu
            740                 745                 750

Phe Glu Ile Lys Arg Thr Val Asp Gly Glu Gly Tyr Asn Val Ala Gln
        755                 760                 765

Cys Asn Met Thr Asp Trp Phe Leu Val Gln Met Leu Ala Asn Tyr Asn
    770                 775                 780

Ile Gly Tyr Gln Gly Phe Tyr Ile Pro Glu Gly Tyr Lys Asp Arg Met
785                 790                 795                 800

Tyr Ser Phe Phe Arg Asn Phe Gln Pro Met Ser Arg Gln Val Val Asp
                805                 810                 815

Glu Val Asn Lys Tyr Asp Phe Lys Ala Val Ile Pro Tyr Gln His Asn
            820                 825                 830

Asn Ser Gly Phe Val Gly Tyr Met Ala Pro Thr Met Arg Gln Gly Gln
        835                 840                 845

Tyr Pro Ala Asn Tyr Pro Tyr Pro Leu Ile Gly Thr Thr Ala Val Asn
    850                 855                 860

Ser Val Thr Gln Lys Lys Phe Leu Cys Asp Arg Thr Met Trp Arg Ile
865                 870                 875                 880

Pro Phe Ser Ser Asn Phe Met Ser Met Gly Ala Leu Thr Asp Leu Gly
```

```
                    885                 890                 895
Gln Asn Met Leu Tyr Ala Asn Ser Ala His Ala Leu Asp Met Thr Phe
                900                 905                 910

Glu Val Asp Pro Met Asp Glu Pro Thr Leu Leu Tyr Leu Leu Phe Glu
                915                 920                 925

Val Phe Asp Val Val Arg Val Gln Pro His Arg Gly Ile Ile Glu Ala
                930                 935                 940

Val Tyr Leu Arg Thr Pro Phe Ser Ala Gly Asn Ala Thr Thr
945                 950                 955
```

<210> SEQ ID NO 44
<211> LENGTH: 946
<212> TYPE: PRT
<213> ORGANISM: Human Adenovirus 35 Hexon Protein

<400> SEQUENCE: 44

```
Leu Ser Arg Arg Ala Pro Gly Phe Pro Leu Val Lys Met Ala Thr Pro
1               5                   10                  15

Ser Met Leu Pro Gln Trp Ala Tyr Met His Ile Ala Gly Gln Asp Ala
                20                  25                  30

Ser Glu Tyr Leu Ser Pro Gly Leu Val Gln Phe Ala Arg Ala Thr Asp
            35                  40                  45

Thr Tyr Phe Asn Leu Gly Asn Lys Phe Arg Asn Pro Thr Val Ala Pro
50                  55                  60

Thr His Asp Val Thr Thr Asp Arg Ser Gln Arg Leu Met Leu Arg Phe
65                  70                  75                  80

Val Pro Val Asp Arg Glu Asp Asn Thr Tyr Ser Tyr Lys Val Arg Tyr
                85                  90                  95

Thr Leu Ala Val Gly Asp Asn Arg Val Leu Asp Met Ala Ser Thr Phe
            100                 105                 110

Phe Asp Ile Arg Gly Val Leu Asp Arg Gly Pro Ser Phe Lys Pro Tyr
        115                 120                 125

Ser Gly Thr Ala Tyr Asn Ser Leu Ala Pro Lys Gly Ala Pro Asn Ala
    130                 135                 140

Ser Gln Trp Leu Asp Lys Gly Val Thr Ser Thr Gly Leu Val Asp Asp
145                 150                 155                 160

Gly Asn Thr Asp Asp Gly Glu Glu Ala Lys Lys Ala Thr Tyr Thr Phe
                165                 170                 175

Gly Asn Ala Pro Val Lys Ala Glu Ala Glu Ile Thr Lys Asp Gly Leu
            180                 185                 190

Pro Val Gly Leu Glu Val Ser Thr Glu Gly Pro Lys Pro Ile Tyr Ala
        195                 200                 205

Asp Lys Leu Tyr Gln Pro Glu Pro Gln Val Gly Asp Thr Trp Thr Asp
    210                 215                 220

Leu Asp Gly Lys Thr Glu Glu Tyr Gly Gly Arg Val Leu Lys Pro Glu
225                 230                 235                 240

Thr Lys Met Lys Pro Cys Tyr Gly Ser Phe Ala Lys Pro Thr Asn Ile
                245                 250                 255

Lys Gly Gly Gln Ala Lys Val Lys Pro Lys Glu Asp Asp Gly Thr Asn
            260                 265                 270

Asn Ile Tyr Asp Ile Asp Met Asn Phe Phe Asp Leu Arg Ser Gln Arg
        275                 280                 285

Ser Glu Leu Lys Pro Lys Ile Val Met Tyr Ala Glu Asn Val Asp Leu
    290                 295                 300
```

-continued

```
Glu Cys Pro Asp Thr His Val Tyr Lys Pro Gly Val Ser Asp Ala
305                 310                 315                 320

Ser Ser Glu Thr Asn Leu Gly Gln Gln Met Pro Asn Arg Pro Asn Tyr
            325                 330                 335

Ile Gly Phe Arg Asp Asn Phe Ile Gly Leu Met Tyr Tyr Asn Ser Thr
            340                 345                 350

Gly Asn Met Gly Val Leu Ala Gly Gln Ala Ser Gln Leu Asn Ala Val
            355                 360                 365

Val Asp Leu Gln Asp Arg Asn Thr Glu Leu Ser Tyr Gln Leu Leu Leu
        370                 375                 380

Ser Leu Gly Asp Arg Thr Arg Tyr Phe Ser Met Trp Asn Gln Ala Val
385                 390                 395                 400

Asp Ser Tyr Asp Pro Asp Val Arg Val Ile Glu Asn His Gly Val Glu
                405                 410                 415

Asp Glu Leu Pro Asn Tyr Cys Phe Pro Leu Asp Gly Val Gly Pro Arg
                420                 425                 430

Thr Asp Ser Tyr Lys Glu Ile Pro Asn Gly Asp Gln Ser Thr Trp Thr
            435                 440                 445

Asn Val Asp Pro Thr Gly Ser Ser Glu Leu Ala Lys Gly Asn Pro Phe
        450                 455                 460

Ala Met Glu Ile Asn Leu Gln Ala Asn Leu Trp Arg Ser Phe Leu Tyr
465                 470                 475                 480

Ser Asn Val Ala Leu Tyr Leu Pro Asp Ser Tyr Lys Tyr Thr Ser Asn
                485                 490                 495

Val Thr Leu Pro Glu Asn Lys Asn Thr Tyr Asp Tyr Met Asn Gly Arg
            500                 505                 510

Val Val Pro Pro Ser Leu Val Asp Thr Tyr Val Asn Ile Gly Ala Arg
        515                 520                 525

Trp Ser Leu Asp Ala Met Asp Asn Val Asn Pro Phe Asn His His Arg
530                 535                 540

Asn Ala Gly Arg Tyr Arg Ser Met Leu Leu Gly Asn Gly Arg Tyr Val
545                 550                 555                 560

Pro Phe His Ile Gln Val Pro Gln Lys Phe Phe Ala Val Lys Asn Leu
                565                 570                 575

Leu Leu Leu Pro Gly Ser Tyr Thr Tyr Glu Trp Asn Phe Arg Lys Asp
            580                 585                 590

Val Asn Met Val Leu Gln Ser Ser Leu Asp Leu Arg Val Asp Gly Ala
        595                 600                 605

Ser Ile Ser Phe Thr Ser Ile Asn Leu Tyr Ala Thr Phe Phe Pro Met
610                 615                 620

Ala His Asn Thr Ala Ser Thr Leu Glu Ala Met Leu Arg Asn Asp Thr
625                 630                 635                 640

Asn Asp Gln Ser Phe Asn Asp Tyr Leu Ser Ala Asn Met Leu Tyr
                645                 650                 655

Pro Ile Ala Asn Ala Thr Asn Ile Pro Ile Ser Ile Pro Ser Arg Asn
            660                 665                 670

Trp Ala Ala Phe Arg Gly Trp Phe Thr Arg Leu Lys Thr Lys Glu Thr
                675                 680                 685

Pro Ser Leu Gly Ser Gly Phe Asp Pro Tyr Phe Val Tyr Ser Gly Ser
        690                 695                 700

Ile Pro Tyr Leu Asp Gly Thr Phe Tyr Leu His Thr His Lys Lys Val
705                 710                 715                 720

Ser Ile Met Phe Asp Ser Ser Val Ser Trp Pro Gly Asn Asp Arg Leu
```

-continued

```
                725                 730                 735
Leu Ser Pro Asn Glu Phe Glu Ile Lys Arg Thr Val Asp Gly Glu Gly
                740                 745                 750

Tyr Asn Val Ala Gln Cys Asn Met Thr Lys Asp Trp Phe Leu Val Trp
            755                 760                 765

Leu Ala Asn Tyr Asn Ile Gly Tyr Gln Gly Phe Tyr Ile Pro Glu Gly
        770                 775                 780

Tyr Lys Asp Arg Met Tyr Ser Phe Phe Arg Asn Phe Gln Pro Met Ser
785                 790                 795                 800

Arg Gln Val Val Asp Glu Val Asn Tyr Lys Asp Phe Lys Ala Val Ala
                805                 810                 815

Ile Pro Tyr Gln His Asn Asn Gly Phe Val Gly Tyr Met Ala Pro Thr
            820                 825                 830

Met Arg Gln Gly Gln Pro Tyr Pro Ala Asn Tyr Pro Tyr Pro Leu Ile
        835                 840                 845

Gly Thr Thr Ala Val Asn Ser Val Thr Gln Lys Lys Phe Leu Cys Asp
    850                 855                 860

Arg Thr Met Trp Arg Ile Pro Phe Ser Ser Asn Phe Met Ser Ala Leu
865                 870                 875                 880

Thr Asp Leu Gly Gln Asn Met Leu Tyr Ala Asn Ser Ala His Ala Leu
                885                 890                 895

Asp Met Thr Phe Glu Val Asp Pro Met Asp Glu Pro Thr Leu Leu Tyr
            900                 905                 910

Leu Leu Phe Glu Val Phe Asp Val Val Arg Val His Gln Pro His Arg
        915                 920                 925

Gly Ile Ile Glu Ala Val Leu Arg Thr Pro Phe Ser Ala Gly Asn Ala
    930                 935                 940

Thr Thr
945

<210> SEQ ID NO 45
<211> LENGTH: 952
<212> TYPE: PRT
<213> ORGANISM: Human Adenovirus 36 Hexon Protein

<400> SEQUENCE: 45

Leu Ser Arg Arg Ala Pro Gly Phe Pro Leu Val Lys Met Ala Thr Pro
1               5                   10                  15

Ser Met Leu Pro Gln Trp Ala Tyr Met His Ile Ala Gly Gln Asp Ala
            20                  25                  30

Ser Glu Tyr Leu Ser Pro Gly Leu Val Gln Phe Ala Arg Ala Thr Asp
        35                  40                  45

Thr Tyr Phe Asn Leu Gly Asn Lys Phe Arg Asn Pro Thr Val Ala Pro
    50                  55                  60

Thr His Asp Val Thr Thr Asp Arg Ser Gln Arg Leu Met Leu Arg Phe
65                  70                  75                  80

Val Pro Val Asp Arg Glu Asp Asn Thr Tyr Ser Tyr Lys Val Arg Tyr
                85                  90                  95

Thr Leu Ala Val Gly Asp Asn Arg Val Leu Asp Met Ala Ser Thr Phe
            100                 105                 110

Phe Asp Ile Arg Gly Val Leu Asp Arg Gly Pro Ser Phe Lys Pro Tyr
        115                 120                 125

Ser Gly Thr Ala Tyr Asn Ser Leu Ala Pro Lys Gly Ala Pro Asn Ala
    130                 135                 140
```

```
Ser Gln Trp Leu Asp Lys Gly Val Thr Ser Thr Gly Leu Val Asp Asp
145                 150                 155                 160

Gly Asn Thr Asp Asp Gly Glu Glu Ala Lys Ala Thr Tyr Thr Phe
            165                 170                 175

Gly Asn Ala Pro Val Lys Ala Glu Ala Glu Ile Thr Lys Asp Gly Leu
            180                 185                 190

Pro Val Gly Leu Glu Val Ser Thr Glu Gly Pro Lys Pro Ile Tyr Ala
            195                 200                 205

Asp Lys Leu Tyr Gln Pro Glu Pro Gln Val Gly Asp Thr Trp Thr Asp
210                 215                 220

Leu Asp Gly Lys Thr Glu Glu Tyr Gly Gly Arg Val Leu Lys Pro Glu
225                 230                 235                 240

Thr Lys Met Lys Pro Cys Tyr Gly Ser Phe Ala Lys Pro Thr Asn Ile
            245                 250                 255

Lys Gly Gly Gln Ala Lys Val Lys Pro Lys Glu Asp Asp Gly Thr Asn
            260                 265                 270

Asn Ile Tyr Asp Ile Asp Met Asn Phe Phe Asp Leu Arg Ser Gln Arg
            275                 280                 285

Ser Glu Leu Lys Pro Lys Ile Val Met Tyr Ala Glu Asn Val Asp Leu
290                 295                 300

Glu Cys Pro Asp Thr His Val Val Tyr Lys Pro Gly Val Ser Asp Ala
305                 310                 315                 320

Ser Ser Glu Thr Asn Leu Gly Gln Gln Ser Met Pro Asn Arg Pro Asn
            325                 330                 335

Tyr Ile Gly Phe Arg Asp Asn Phe Ile Gly Leu Met Tyr Tyr Asn Ser
            340                 345                 350

Thr Gly Asn Met Gly Val Leu Ala Gly Gln Ala Ser Gln Leu Asn Ala
            355                 360                 365

Val Val Asp Leu Gln Asp Arg Asn Thr Glu Leu Ser Tyr Gln Leu Leu
            370                 375                 380

Asp Ser Leu Gly Asp Arg Thr Arg Tyr Phe Ser Met Trp Asn Gln Ala
385                 390                 395                 400

Val Asp Ser Tyr Asp Pro Asp Val Arg Val Ile Glu Asn His Gly Val
            405                 410                 415

Glu Asp Glu Leu Pro Asn Tyr Cys Phe Pro Leu Asp Gly Val Gly Pro
            420                 425                 430

Arg Thr Asp Ser Tyr Lys Ile Lys Pro Asn Gly Asp Gln Ser Thr Trp
            435                 440                 445

Thr Asn Val Asp Pro Thr Gly Ser Ser Glu Leu Ala Lys Gly Asn Pro
            450                 455                 460

Phe Ala Met Glu Ile Asn Leu Gln Ala Asn Leu Trp Arg Ser Phe Leu
465                 470                 475                 480

Tyr Ser Asn Val Ala Leu Tyr Leu Pro Asp Ser Tyr Lys Tyr Thr Pro
            485                 490                 495

Ser Asn Val Thr Leu Pro Glu Asn Lys Asn Thr Tyr Asp Tyr Met Asn
            500                 505                 510

Gly Arg Val Val Pro Pro Ser Leu Val Asp Thr Tyr Val Asn Ile Gly
            515                 520                 525

Ala Arg Trp Ser Leu Asp Ala Met Asp Asn Val Asn Pro Phe Asn His
            530                 535                 540

His Arg Ala Gly Leu Arg Tyr Arg Ser Met Leu Leu Gly Asn Gly Arg
545                 550                 555                 560

Tyr Val Pro Phe His Ile Gln Val Pro Gln Lys Phe Phe Ala Val Lys
```

-continued

```
                565                 570                 575
Asn Leu Leu Leu Leu Pro Gly Ser Tyr Thr Tyr Glu Trp Asn Phe Arg
            580                 585                 590
Lys Asp Val Asn Met Val Leu Gln Ser Leu Gly Asn Asp Leu Arg Val
            595                 600                 605
Asp Gly Ala Ser Ile Ser Phe Thr Ser Ile Asn Leu Tyr Ala Thr Phe
            610                 615                 620
Phe Pro Met Ala His Asn Thr Ala Ser Thr Leu Glu Ala Met Leu Arg
625                 630                 635                 640
Asn Asp Thr Asn Asp Gln Ser Phe Asn Asp Tyr Leu Ser Ala Ala Asn
            645                 650                 655
Met Leu Tyr Pro Ile Pro Ala Asn Ala Thr Asn Ile Pro Ile Ser Ile
            660                 665                 670
Pro Ser Arg Asn Trp Ala Ala Phe Arg Gly Trp Ser Phe Thr Arg Leu
            675                 680                 685
Lys Thr Lys Glu Thr Pro Ser Leu Gly Ser Gly Phe Asp Pro Tyr Phe
            690                 695                 700
Val Tyr Ser Gly Ser Ile Pro Tyr Asp Gly Thr Phe Tyr Leu Asn His
705                 710                 715                 720
Thr Phe Lys Lys Val Ser Ile Met Phe Asp Ser Ser Val Ser Trp Pro
            725                 730                 735
Gly Asn Asp Arg Leu Leu Ser Pro Asn Glu Phe Glu Ile Lys Arg Thr
            740                 745                 750
Val Asp Gly Asp Gly Tyr Asn Val Ala Gln Cys Asn Met Thr Lys Trp
            755                 760                 765
Phe Leu Val Gln Met Leu Ala Asn Tyr Asn Ile Gly Tyr Gln Gly Phe
            770                 775                 780
Tyr Ile Pro Glu Gly Tyr Lys Asp Arg Met Tyr Ser Phe Phe Arg Asn
785                 790                 795                 800
Phe Gln Pro Met Ser Arg Gln Val Val Asp Glu Val Asn Tyr Lys Asp
            805                 810                 815
Phe Lys Ala Val Ile Tyr Gln His Asn Asn Ser Gly Phe Val Gly Tyr
            820                 825                 830
Met Ala Pro Thr Met Arg Gln Gly Gln Pro Tyr Pro Ala Asn Tyr Pro
            835                 840                 845
Tyr Pro Leu Ile Gly Thr Thr Ala Val Asn Ser Val Thr Gln Lys Lys
            850                 855                 860
Phe Leu Cys Asp Arg Thr Met Trp Arg Ile Pro Phe Ser Ser Asn Phe
865                 870                 875                 880
Met Ser Met Gly Ala Leu Thr Asp Leu Gly Gln Asn Met Leu Tyr Ala
            885                 890                 895
Asn Ser Ala His Ala Leu Asp Met Thr Phe Glu Val Asp Pro Met Asp
            900                 905                 910
Glu Pro Thr Leu Leu Tyr Leu Leu Phe Glu Val Phe Asp Val Val Arg
            915                 920                 925
Val Gln Pro His Arg Gly Ile Ile Glu Ala Val Tyr Leu Arg Thr Pro
            930                 935                 940
Phe Ser Ala Gly Asn Ala Thr Thr
945                 950

<210> SEQ ID NO 46
<211> LENGTH: 953
<212> TYPE: PRT
<213> ORGANISM: Human Adenovirus 41 Hexon Protein
```

```
<400> SEQUENCE: 46

Val Cys Val His Val Ala Ala Arg Gly Ala Glu Pro Pro Arg Ala
1               5                   10                  15

Arg Phe Pro Leu Val Lys Met Ala Thr Pro Ser Met Met Pro Gln Trp
            20                  25                  30

Ala Tyr Met His Ile Ala Gly Gln Asp Ala Ser Glu Tyr Leu Ser Pro
                35                  40                  45

Gly Leu Val Gln Phe Ala Arg Ala Thr Asp Thr Tyr Phe Ser Leu Gly
            50                  55                  60

Asn Lys Phe Arg Asn Pro Thr Val Ala Pro Thr His Asp Val Thr Thr
65                  70                  75                  80

Asp Arg Ser Gln Arg Leu Thr Leu Arg Phe Ser Pro Ser Asp Arg Glu
                85                  90                  95

Asp Thr Thr Tyr Ser Tyr Lys Ala Arg Phe Thr Leu Ala Gly Asp Asn
            100                 105                 110

Arg Val Leu Asp Met Ala Ser Thr Tyr Phe Asp Ile Arg Gly Val Leu
            115                 120                 125

Asp Arg Gly Pro Ser Phe Lys Pro Tyr Ser Gly Thr Ala Tyr Asn Ser
130                 135                 140

Leu Ala Pro Lys Gly Ala Pro Asn Ser Ser Gln Trp Ala Asp Lys Glu
145                 150                 155                 160

Arg Val Asn Gly Gly Gly Asn Thr Lys Asp Val Thr Lys Thr Phe Gly
                165                 170                 175

Val Ala Ala Met Gly Gly Glu Asp Ile Thr Glu Lys Gly Leu Lys Ile
            180                 185                 190

Gly Thr Asp Thr Thr Ala Asn Glu Pro Ile Phe Ala Asp Lys Asn Phe
        195                 200                 205

Gln Pro Glu Pro Gln Val Gly Glu Glu Asn Gln Glu Thr Phe Val Phe
    210                 215                 220

Tyr Gly Gly Arg Ala Leu Lys Lys Glu Thr Lys Met Lys Pro Cys Tyr
225                 230                 235                 240

Gly Ser Phe Ala Arg Pro Thr Asn Glu Lys Gly Gly Gln Ala Lys Phe
                245                 250                 255

Ile Ile Gly Asp Asn Gly Gln Pro Thr Glu Asn His Asp Ile Thr Met
            260                 265                 270

Ala Phe Asp Thr Pro Gly Gly Thr Ile Thr Gly Gly Thr Gly Gly Pro
        275                 280                 285

Gln Asp Glu Leu Lys Ala Asp Ile Val Met Tyr Thr Glu Asn Ile Asn
    290                 295                 300

Leu Glu Thr Pro Asp Thr His Val Val Tyr Lys Pro Gly Lys Glu Asp
305                 310                 315                 320

Asp Ser Ser Glu Ile Asn Leu Val Gln Ser Met Pro Asn Arg Pro Asn
                325                 330                 335

Tyr Ile Gly Phe Arg Asp Asn Phe Val Gly Leu Met Tyr Tyr Asn Ser
            340                 345                 350

Thr Gly Asn Met Gly Val Leu Ala Gly Gln Ala Ser Gln Leu Asn Ala
        355                 360                 365

Val Val Asp Leu Gln Asp Arg Asn Thr Glu Leu Ser Tyr Gln Leu Leu
    370                 375                 380

Asp Ser Leu Gly Asp Arg Thr Arg Tyr Phe Ser Met Trp Asn Ser Ala
385                 390                 395                 400

Val Asp Ser Tyr Asp Pro Asp Val Arg Ile Ile Glu Asn His Gly Val
```

-continued

```
            405                 410                 415
Glu Asp Glu Leu Pro Asn Tyr Cys Phe Pro Leu Asp Gly Ser Gly Thr
            420                 425                 430
Asn Ser Ala Phe Gln Gly Lys Ile Lys Gln Asn Gln Asp Gly Asp Val
            435                 440                 445
Asn Asp Asp Trp Glu Lys Asp Asp Lys Val Ser Thr Gln Asn Gln Ile
            450                 455                 460
Cys Lys Gly Asn Glu Tyr Ala Met Glu Ile Asn Leu Gln Ala Asn Leu
465                 470                 475                 480
Trp Lys Ser Phe Leu Tyr Ser Asn Val Ala Leu Tyr Leu Asp Ser Tyr
            485                 490                 495
Lys Tyr Thr Pro Ala Asn Val Thr Leu Pro Thr Asn Thr Asn Thr Glu
            500                 505                 510
Tyr Met Asn Gly Arg Val Val Ala Pro Ser Leu Val Asp Ala Tyr Ile
            515                 520                 525
Asn Ile Gly Ala Arg Trp Ser Leu Asp Pro Met Asp Asn Val Asn Pro
            530                 535                 540
Phe Asn His Arg Asn Ala Gly Leu Arg Tyr Arg Ser Asn Ala Ser Gly
545                 550                 555                 560
Gln Arg Pro Leu Arg Ala Leu Pro His Pro Ser Ala Pro Lys Val Leu
            565                 570                 575
Cys His Gln Glu Pro Ala Pro Ala Pro Gly Leu Leu His Leu Arg Val
            580                 585                 590
Glu Leu Pro Gln Gly Arg Gln His Asp Ala Glu Phe Pro Arg Lys Arg
            595                 600                 605
Pro Ala Arg Arg Arg Leu Arg Ala Leu Arg Gln Arg Gln Pro Leu
            610                 615                 620
Cys His Ile Leu Pro His Gly Ala Gln His Arg Leu His Pro Gly Ser
625                 630                 635                 640
His Ala Ala Gln Arg His Gln Arg Pro Val Leu Gln Arg Leu Pro Leu
            645                 650                 655
Arg Gln His Ala Leu Pro His Pro Gly Gln Gly His Gln Arg Ala His
            660                 665                 670
Leu His Pro Ala Gln Leu Gly Arg Leu Ser Arg Leu Glu Phe His Pro
            675                 680                 685
Ala Gln Asp Gln Gly Asn Ser Phe Pro Arg Leu Gly Phe Arg Pro Leu
            690                 695                 700
Leu Cys Leu Leu Gly Leu His Pro Leu Pro Arg Arg Asp Leu Leu Pro
705                 710                 715                 720
Gln Pro His Leu Gln Glu Gly Leu His His Val Arg Leu Leu Gly Gln
            725                 730                 735
Leu Ala Arg Gln Arg Thr Ala Val Thr Pro Asn Glu Phe Glu Ile Lys
            740                 745                 750
Arg Ser Val Asp Gly Glu Gly Tyr Asn Val Ala Gln Cys Met Thr Lys
            755                 760                 765
Asp Trp Phe Leu Val Gln Met Leu Ser His Tyr Asn Ile Gly Tyr Gln
            770                 775                 780
Gly Phe His Val Pro Glu Gly Tyr Lys Asp Arg Met Tyr Ser Phe Phe
785                 790                 795                 800
Arg Asn Phe Gln Pro Met Ser Arg Gln Val Val Asp Glu Ile Asn Tyr
            805                 810                 815
Lys Asp Tyr Ala Val Thr Leu Pro Phe Gln His Asn Asn Ser Gly Phe
            820                 825                 830
```

```
Thr Gly Tyr Leu Ala Pro Thr Met Arg Gln Gly Gln Pro Tyr Pro Ala
            835                 840                 845

Asn Phe Pro Leu Ile Gly Ser Thr Ala Val Pro Ser Val Thr Gln Lys
            850                 855                 860

Lys Phe Leu Cys Asp Arg Val Met Trp Arg Ile Pro Phe Ser Ser Asn
865                 870                 875                 880

Phe Met Ser Met Gly Ala Leu Thr Asp Leu Gly Gln Asn Met Leu Tyr
            885                 890                 895

Ala Asn Ser Ala His Ala Leu Asp Ile Thr Phe Glu Val Asp Pro Met
            900                 905                 910

Asp Glu Pro Thr Leu Leu Tyr Leu Leu Phe Glu Val Phe Asp Val Val
            915                 920                 925

Val His Gln Pro His Arg Gly Val Ile Glu Ala Val Tyr Leu Arg Thr
            930                 935                 940

Pro Phe Ser Ala Gly Asn Ala Thr Thr
945                 950

<210> SEQ ID NO 47
<211> LENGTH: 23
<212> TYPE: DNA
<213> ORGANISM: Primer/Oligonucleotide

<400> SEQUENCE: 47
aattgtctta attaaccgct taa                                            23

<210> SEQ ID NO 48
<211> LENGTH: 47
<212> TYPE: DNA
<213> ORGANISM: Primer/Oligonucleotide

<400> SEQUENCE: 48
ctgtacgtac cagtgcactg gcctaggcat ggaaaaatac ataactg                  47

<210> SEQ ID NO 49
<211> LENGTH: 64
<212> TYPE: DNA
<213> ORGANISM: Primer/Oligonucleotide

<400> SEQUENCE: 49
gcggatcctt cgaaccatgg taagcttggt accgctagcg ttaaccgggc gactcagtca    60
atcg                                                                 64

<210> SEQ ID NO 50
<211> LENGTH: 28
<212> TYPE: DNA
<213> ORGANISM: Primer/Oligonucleotide

<400> SEQUENCE: 50
gcgccaccat gggcagagcg atggtggc                                       28

<210> SEQ ID NO 51
<211> LENGTH: 50
<212> TYPE: DNA
<213> ORGANISM: Primer/Oligonucleotide

<400> SEQUENCE: 51
gttagatcta agcttgtcga catcgatcta ctaacagtag agatgtagaa               50

<210> SEQ ID NO 52
```

```
<211> LENGTH: 21
<212> TYPE: DNA
<213> ORGANISM: Primer/Oligonucleotide

<400> SEQUENCE: 52
gggtattagg ccaaaggcgc a                                          21

<210> SEQ ID NO 53
<211> LENGTH: 33
<212> TYPE: DNA
<213> ORGANISM: Primer/Oligonucleotide

<400> SEQUENCE: 53
gatcccatgg aagcttgggt ggcgacccca gcg                             33

<210> SEQ ID NO 54
<211> LENGTH: 36
<212> TYPE: DNA
<213> ORGANISM: Primer/Oligonucleotide

<400> SEQUENCE: 54
gatcccatgg ggatccttta ctaagttaca aagcta                          36

<210> SEQ ID NO 55
<211> LENGTH: 19
<212> TYPE: DNA
<213> ORGANISM: Primer/Oligonucleotide

<400> SEQUENCE: 55
gtcgctgtag ttggactgg                                             19

<210> SEQ ID NO 56
<211> LENGTH: 42
<212> TYPE: DNA
<213> ORGANISM: Primer/Oligonucleotide

<400> SEQUENCE: 56
cgacatatgt agatgcatta gtttgtgtta tgtttcaacg tg                   42

<210> SEQ ID NO 57
<211> LENGTH: 18
<212> TYPE: DNA
<213> ORGANISM: Primer/Oligonucleotide

<400> SEQUENCE: 57
ggagaccact gccatgtt                                              18

<210> SEQ ID NO 58
<211> LENGTH: 47
<212> TYPE: DNA
<213> ORGANISM: Primer/Oligonucleotide

<400> SEQUENCE: 58
ctgtacgtac cagtgcactg gcctaggcat ggaaaaatac ataactg               47

<210> SEQ ID NO 59
<211> LENGTH: 64
<212> TYPE: DNA
<213> ORGANISM: Primer/Oligonucleotide

<400> SEQUENCE: 59
gcggatcctt cgaaccatgg taagcttggt accgctagcg ttaaccgggc gactcagtca    60
atcg                                                              64
```

<210> SEQ ID NO 60
<211> LENGTH: 28
<212> TYPE: DNA
<213> ORGANISM: Primer/Oligonucleotide

<400> SEQUENCE: 60
gcgccaccat gggcagagcg atggtggc                                28

<210> SEQ ID NO 61
<211> LENGTH: 50
<212> TYPE: DNA
<213> ORGANISM: Primer/Oligonucleotide

<400> SEQUENCE: 61
gttagatcta agcttgtcga catcgatcta ctaacagtag agatgtagaa        50

<210> SEQ ID NO 62
<211> LENGTH: 10
<212> TYPE: DNA
<213> ORGANISM: Primer/Oligonucleotide

<400> SEQUENCE: 62
ttaagtcgac                                                    10

<210> SEQ ID NO 63
<211> LENGTH: 32
<212> TYPE: DNA
<213> ORGANISM: Primer/Oligonucleotide

<400> SEQUENCE: 63
ggggtggcca gggtacctct aggcttttgc aa                           32

<210> SEQ ID NO 64
<211> LENGTH: 29
<212> TYPE: DNA
<213> ORGANISM: Primer/Oligonucleotide

<400> SEQUENCE: 64 gggggatcc ataaacaagt tcagaatcc                                29

<210> SEQ ID NO 65
<211> LENGTH: 18
<212> TYPE: DNA
<213> ORGANISM: Primer/Oligonucleotide

<400> SEQUENCE: 65
cctggtgctg ccaacagc                                           18

<210> SEQ ID NO 66
<211> LENGTH: 30
<212> TYPE: DNA
<213> ORGANISM: Primer/Oligonucleotide

<400> SEQUENCE: 66
ccggatccac tagtggaaag cgggcgcgcg                              30

<210> SEQ ID NO 67
<211> LENGTH: 35
<212> TYPE: DNA
<213> ORGANISM: Primer/Oligonucleotide

<400> SEQUENCE: 67

```
ccggatccaa ttgagaagca agcaacatca acaac                              35

<210> SEQ ID NO 68
<211> LENGTH: 19
<212> TYPE: DNA
<213> ORGANISM: Primer/Oligonucleotide

<400> SEQUENCE: 68
gagaagggca tggaggctg                                                19

<210> SEQ ID NO 69
<211> LENGTH: 32
<212> TYPE: DNA
<213> ORGANISM: Primer/Oligonucleotide

<400> SEQUENCE: 69
ggacgtgtaa gatggcyacc cchtcgatgm tg                                 32

<210> SEQ ID NO 70
<211> LENGTH: 31
<212> TYPE: DNA
<213> ORGANISM: Primer/Oligonucleotide

<400> SEQUENCE: 70
ccatcgatgg ttatgtkgtk gcgttrccgg c                                  31

<210> SEQ ID NO 71
<211> LENGTH: 20
<212> TYPE: DNA
<213> ORGANISM: Primer/Oligonucleotide

<400> SEQUENCE: 71
ctgttgctgc tgctaatagc                                               20

<210> SEQ ID NO 72
<211> LENGTH: 32
<212> TYPE: DNA
<213> ORGANISM: Primer/Oligonucleotide

<400> SEQUENCE: 72
cgcggatcct gtacaactaa ggggaataca ag                                 32

<210> SEQ ID NO 73
<211> LENGTH: 33
<212> TYPE: DNA
<213> ORGANISM: Primer/Oligonucleotide

<400> SEQUENCE: 73
cgcggatccc ttaaggcaag catgtccatc ctt                                33

<210> SEQ ID NO 74
<211> LENGTH: 27
<212> TYPE: DNA
<213> ORGANISM: Primer/Oligonucleotide

<400> SEQUENCE: 74
aaaacacgtt ttacgcgtcg acctttc                                       27

<210> SEQ ID NO 75
<211> LENGTH: 33
<212> TYPE: DNA
<213> ORGANISM: Primer/Oligonucleotide

<400> SEQUENCE: 75
```
gctcgatgta caatgcggcg cgcggcgatg tat        33

<210> SEQ ID NO 76
<211> LENGTH: 33
<212> TYPE: DNA
<213> ORGANISM: Primer/Oligonucleotide

<400> SEQUENCE: 76
gctcgactta agtcaaaaag tgcggctcga tag        33

<210> SEQ ID NO 77
<211> LENGTH: 28
<212> TYPE: DNA
<213> ORGANISM: Primer/Oligonucleotide

<400> SEQUENCE: 77
gctcgatgta caatgaggag acgagccg              28

<210> SEQ ID NO 78
<211> LENGTH: 33
<212> TYPE: DNA
<213> ORGANISM: Primer/Oligonucleotide

<400> SEQUENCE: 78
gctcgactta agttagaaag tgcggcttga aag        33

<210> SEQ ID NO 79
<211> LENGTH: 35
<212> TYPE: DNA
<213> ORGANISM: Primer/Oligonucleotide

<400> SEQUENCE: 79
gctcgatgta caatgaggcg tgcggtggtg tcttc      35

<210> SEQ ID NO 80
<211> LENGTH: 34
<212> TYPE: DNA
<213> ORGANISM: Primer/Oligonucleotide

<400> SEQUENCE: 80
gctcgactta agttagaagg tgcgactgga aagc       34

<210> SEQ ID NO 81
<211> LENGTH: 33
<212> TYPE: DNA
<213> ORGANISM: Primer/Oligonucleotide

<400> SEQUENCE: 81
gctcgatgta caatgagacg tgcggtggga gtg        33

<210> SEQ ID NO 82
<211> LENGTH: 33
<212> TYPE: DNA
<213> ORGANISM: Primer/Oligonucleotide

<400> SEQUENCE: 82
gctcgactta agttaaaacg tgcggctaga cag        33

<210> SEQ ID NO 83
<211> LENGTH: 19
<212> TYPE: DNA
<213> ORGANISM: Primer/Oligonucleotide

```
<400> SEQUENCE: 83
aattgtctta attaaccgc                                           19

<210> SEQ ID NO 84
<211> LENGTH: 19
<212> TYPE: DNA
<213> ORGANISM: Primer/Oligonucleotide

<400> SEQUENCE: 84
aattgcggtt aattaagac                                           19

<210> SEQ ID NO 85
<211> LENGTH: 6
<212> TYPE: PRT
<213> ORGANISM: Human Adenovirus

<400> SEQUENCE: 85

Phe Asn Pro Val Tyr Pro
1               5

<210> SEQ ID NO 86
<211> LENGTH: 30
<212> TYPE: DNA
<213> ORGANISM: Primer/Oligonucleotide

<400> SEQUENCE: 86
ccggatccca attgggaaag cgggcgcgcg                               30

<210> SEQ ID NO 87
<211> LENGTH: 36
<212> TYPE: DNA
<213> ORGANISM: Primer/Oligonucleotide

<400> SEQUENCE: 87
ccggatcctg atcaagaagc aagcaacatc aacaac                        36
```

CHIMERIC ADENOVIRUSES

CROSS-REFERENCE TO RELATED APPLICATIONS

This application is a continuation of application Ser. No. 09/348,354, filed Jul. 7, 1999, now abandoned, the contents of the entirety of which is incorporated by this reference.

STATEMENT ACCORDING TO 37 C.F.R. §1.52(e)(5)—SEQUENCE LISTING SUBMITTED ON COMPACT DISC

Pursuant to 37 C.F.R. §1.52(e)(1)(iii), a compact disc containing an electronic version of the Sequence Listing has been submitted concomitant with this application, the contents of which are hereby incorporated by reference. A second compact disc is submitted and is an identical copy of the first compact disc. The discs are labeled "copy 1" and "copy 2," respectively, and each disc contains one file entitled "Sequence Listing.txt" which is 134 KB and created on Aug. 18, 2005.

TECHNICAL FIELD

The invention relates to the field of molecular genetics and medicine. In particular the present invention relates to the field of gene therapy, more in particular to gene therapy using viruses, especially adenoviruses.

BACKGROUND

In gene therapy, genetic information is delivered to a host cell in order to either correct (supplement) a genetic deficiency in the cell, or to inhibit an unwanted function in the cell, or to eliminate the host cell. Of course, the genetic information can also be intended to provide the host cell with a wanted function, for instance to supply a secreted protein to treat other cells of the host, etc.

Thus, there are basically three different approaches in gene therapy, one directed towards compensating a deficiency present in a (mammalian) host; the second directed towards the removal or elimination of unwanted substances (organisms or cells) and the third towards providing a cell with a wanted function.

For the purpose of gene therapy, adenoviruses have been proposed as suitable vehicles to deliver genes to the host. Gene-transfer vectors derived from adenoviruses (so-called adenoviral vectors) have a number of features that make them particularly useful for gene transfer. 1) the biology of the adenoviruses is characterized in detail, 2) the adenovirus is not associated with severe human pathology, 3) the virus is extremely efficient in introducing its DNA into the host cell, 4) the virus can infect a wide variety of cells and has a broad host-range, 5) the virus can be produced at high virus titers in large quantities, and 6) the virus can be rendered replication defective by deletion of the early-region 1 (E1) of the viral genome (Brody et al., 1994). However, there are still drawbacks associated with the use of adenoviral vectors. Typically, adenoviruses, especially the well investigated serotypes usually elicit an immune response by a host into which they are introduced. Also, although the virus generally spoken has a wide infection range, there is a problem in targeting certain cells and tissues. Also, the replication and other functions of the adenovirus are not always very well suited for the cells which are to be provided with the additional genetic material.

The adenovirus genome is a linear double-stranded DNA molecule of approximately 36000 base pairs. The adenovirus DNA contains identical Inverted Terminal Repeats (ITR) of approximately 90-140 base pairs with the exact length depending on the serotype. The viral origins of replication are within the ITRs exactly at the genome ends.

Most adenoviral vectors currently used in gene therapy have a deletion in the E1 region, where novel genetic information can be introduced. The E1 deletion renders the recombinant virus replication defective (Levrero et al., 1991). It has been demonstrated extensively that recombinant adenovirus, in particular serotype 5 is suitable for efficient transfer of genes in vivo to the liver, the airway epithelium and solid tumors in animal models and human xenografts in immuno-deficient mice (Bout, 1996; Blaese et al., 1995). Thus, preferred methods for in vivo gene transfer into target cells make use of adenoviral vectors as gene delivery vehicles.

At present, six different subgroups of human adenoviruses have been proposed which in total encompasses 51 distinct adenovirus serotypes (see table 1). Besides these human adenoviruses an extensive number of animal adenoviruses have been identified (see Ishibashi et al., 1983).

A serotype is defined on the basis of its immunological distinctiveness as determined by quantitative neutralization with animal antisera (horse, rabbit). If neutralization shows a certain degree of cross-reaction between two viruses, distinctiveness of serotype is assumed if A) the hemagglutinins are unrelated, as shown by lack of cross-reaction on hemagglutination-inhibition, or B) substantial biophysical/biochemical differences in DNA exist (Francki et al., 1991). The nine serotypes identified last (42-51) were isolated for the first time from HIV-infected patients (Hierholzer et al. 1988; Schnurr et al. 1993; De Jong et al. 1998). For reasons not well understood, most of such immuno-compromised patients shed adenoviruses that were rarely or never isolated from immuno-competent individuals (Hierholzer et al. 1988, 1992; Khoo et al., 1995, De Jong et al., 1998).

Besides differences towards the sensitivity against neutralizing antibodies of different adenovirus serotypes, it has also been shown that adenoviruses in subgroup C such as Ad2, and Ad5 bind to different receptors as compared to adenoviruses from subgroup B such as Ad3 (Defer et al., 1990). Likewise, it was demonstrated that receptor specificity could be altered by exchanging the Ad3 with the Ad 5 knob protein, and vice versa (Krasnykh et al., 1996; Stevenson et al., 1995, 1997). The adenovirus serotype 5 ("Ad5") is most widely used for gene therapy purposes. Similar to serotypes 2, 4 and 7, serotype 5 has a natural affiliation towards lung epithelia and other respiratory tissues. In contrast, it is known that, for instance, serotypes 40 and 41 have a natural affiliation towards the gastrointestinal tract. For a detailed overview of the disease association of the different adenovirus serotypes see table 2. The serotypes described above, differ in at least capsid proteins (penton-base, hexon), proteins responsible for cell binding (fiber protein), and proteins involved in adenovirus replication.

One of the major problems of adenovirus gene therapy is thus that none of the above described serotypes are ideally suitable for delivering additional genetic material to host cells. Some have a somewhat limited host range, but have the benefit of being less immunogenic, some are the other way round. Some have a problem of being of a limited virulence, but have a broad host range and/or a reduced immunogenicity. To make things even more complicated this variation in the adenovirus serotypes is also very dependent on the host to be treated. Some hosts may already have encountered certain serotypes and thus mount a strong immune response to the

SUMMARY OF THE INVENTION

The present invention now makes use of the fact that some adenoviruses have lower immunogenicity than others, which others typically excel in one of the other requirements for an efficient gene therapy regime, such as having a high specificity for a certain group of host cells, a good replication machinery in such host cells, a high rate of infection in certain host cells, etc.

The invention thus provides chimeric adenoviruses having the useful properties of at least two adenoviruses of different serotypes. Typically, more than two requirements from the previously given non-exhaustive list are required to obtain an adenovirus capable of efficiently transferring additional material to a host cell and therefore the invention provides adenovirus derived vectors which can be used as cassettes to insert different adenoviral genes from different adenoviral serotypes at the required sites for obtaining a vector capable of expressing a chimeric adenovirus, whereby of course, also a gene of interest can be inserted at for instance the site of E1 of the original adenovirus from which the vector is derived. In this manner the chimeric adenovirus to be produced can be adapted to the requirements and needs of certain hosts in need of gene therapy for certain disorders. Of course, to enable this production a packaging cell will generally be needed in order to produce sufficient amount of safe chimeric adenoviruses.

Thus, in one embodiment, the invention provides a chimeric adenovirus including at least a part of a fiber protein and/or a protein involved in replication of an adenovirus serotype providing the chimeric virus with a desired host range and/or improved replication properties and at least a part of a penton or hexon protein from another less antigenic adenovirus serotype resulting in a less antigenic chimeric adenovirus. Typically, such a virus will be produced using a vector (typically a plasmid, a cosmid or baculovirus system which vector is of course, also part of the present invention. A preferred vector is a vector which can be used to make a chimeric recombinant virus specifically adapted to the host to be treated and the disorder to be treated. Such a vector is another embodiment of the present invention. Thus, the invention also provides a recombinant vector derived from an adenovirus including at least one ITR and a packaging signal, having an insertion site for a nucleic acid sequence of interest, and further having an insertion site for functionally inserting a gene encoding a penton and/or a hexon protein of a first serotype of adenovirus and having an insertion site for a gene encoding a fiber protein of a second adenovirus of a different serotype, and/or an insertion site for a gene derived from a serotype having improved characteristics in the function carried out by that gene or its product. Typically, the invention provides cassettes which allow for the production of any desired chimeric adenovirus, be it only derived from two serotypes or as many as needed to obtain the desired characteristics, whereby it is not always necessary that all characteristics are the best when seen as single properties. It may not even be necessary, for instance, to always alter penton and/or hexon together with another part of adenovirus genes. Sometimes the immunogenicity needs not be altered together with other properties. However, it is preferred to use penton and/or hexon genes from less immunogenic adenovirus serotypes. An important feature of the present invention is the means to produce the chimeric virus. Typically, one does not want an adenovirus batch to be administered to the host cell which contains replication competent adenovirus, although this is not always true. In general therefor it is desired to omit a number of genes (but at least one) from the adenoviral genome on the vector encoding the chimeric virus and to supply these genes in the genome of the cell in which the vector is brought to produce chimeric adenovirus. Such a cell is usually called a packaging cell. The invention thus also provides a packaging cell for producing a chimaeric adenovirus according to the invention, including in trans all elements necessary for adenovirus production not present on the adenoviral vector according to the invention. Typically, vector and packaging cell have to be adapted to one another in that they have all the necessary elements, but that they do not have overlapping elements which lead to replication competent virus by recombination.

Thus, the invention also provides a kit of parts including a packaging cell according to the invention and a recombinant vector according the invention whereby there is essentially no sequence overlap leading to recombination resulting in the production of replication competent adenovirus between the cell and the vector.

In order to be able to precisely adapt the viral vector and provide the chimaeric virus with the desired properties at will, it is preferred that a library of adenoviral genes is provided whereby the genes are located within restriction sites. Typically, it is preferred to have same kinds of genes of different serotypes within the same restriction sites and to have that same restriction site in the adenoviral vector used to produce the chimaeric virus. If all sites for different genes are unique, then a system to pick and choose from has been made. One can cut a penton gene from the desired serotype from the library and insert it at the same site in the vector. One can then use a different restriction enzyme to cut a replication gene from the bank of a different serotype using another restriction enzyme and insert that gene at the corresponding restriction site in the chimaeric vector. Thus, it is to be preferred to have a vector according to the invention where the insertion sites are different and preferably unique restriction sites. Preferably, this vector is combined with a library having the corresponding genes within the same restriction sites. Methods to use this library and the vector are within the skill in the art and are part of the present invention. Typically, such a method includes a number of restriction and ligation steps and expression of the result in a packaging cell. Also, one can use a library from which the different desired adenoviral genes are obtained through homologous recombination or a combination of restriction and recombination. Thus, the invention provides a method for producing a chimaeric adenovirus having a desired host range and diminished antigenicity, including providing a vector according to the invention having the desired insertion sites, inserting into the vector at least a functional part of a penton or hexon protein derived from an adenovirus serotype having relatively low antigenicity, inserting at least a functional part of a fiber protein derived from an adenovirus serotype having the desired host range and transfecting the vector in a packaging cell according to the invention and allowing for production of chimaeric viral particles. Of course, other combinations of other viral genes originating from different serotypes can also be inserted as disclosed herein before.

An immunogenic response to adenovirus that typically occurs is the production of neutralizing antibodies by the host. This is typically a reason for selecting a penton, hexon and/or fiber of a less immunogenic serotype.

Of course, it may not be necessary to make chimaeric adenoviruses which have complete proteins from different serotypes. It is well within the skill of the art to produce chimaeric proteins, for instance in the case of fiber proteins it is very well possible to have the base of one serotype and the shaft and the knob from another serotype. In this manner it becomes possible to have the parts of the protein responsible for assembly of viral particles originate from one serotype, thereby enhancing the production of intact viral particles. Thus, the invention also provides a chimaeric adenovirus according to the invention, wherein the hexon, penton and/or fiber proteins are chimaeric proteins originating from different adenovirus serotypes. Besides generating chimaeric adenoviruses by swapping entire wild type hexon, penton, fiber (protein) genes etc. or parts thereof, it is also within the scope of the present invention to insert hexon, penton, fiber (protein) genes etc. carrying mutations such as point mutations, deletions, insertions etc. which can be easily screened for preferred characteristics such as temperature stability, assembly, anchoring, redirected infection, altered immune response etc. Again other chimaeric combinations can also be produced and are within the scope of the present invention.

The availability of a library of nucleic acids derived from different serotypes allows, among others, the generation of a library of chimaeric adenoviruses. The invention therefore further provides a library of chimaeric adenoviruses. In one embodiment the invention provides a library of chimaeric adenoviruses wherein the adenoviruses include chimeric capsids, i.e., including capsid proteins derived at least in part from at least two different adenovirus serotypes. Preferably, nucleic acid and/or protein or parts thereof, from at least one representative adenovirus of each adenovirus subgroup is represented in the (chimaeric) adenovirus library. Preferably, nucleic acid and/or protein or parts thereof is derived from more than one representative of each adenovirus subgroup. Most preferably, the library includes nucleic acid and/or protein or a part thereof, from essentially every known representative of each adenovirus subgroup. Nucleic acid and/or protein or parts thereof derived from more than one representative adenovirus from each adenovirus subgroup in the (chimaeric) library is desired because a desirable property may not be a general property of a subgroup. Also, a desirable property of a subgroup of adenovirus may be expressed in different amounts on the various members of the subgroup. Ensuring that more than one representative of a subgroup is represented in the library thus warrants the selection of the best expressor of the desired property.

Typically, a library of chimaeric adenoviruses (or a part thereof) is used in screening assays to determine properties of the chimaeric adenoviruses. Any particular chimaeric adenovirus including particularly desirable properties can thereby be identified and subsequently be used in, for instance, the development of an improved nucleic acid delivery vehicle. Desirable properties the chimaeric adenovirus library may be screened for include, but are not limited to, target cell specificity, reduced immunogenicity, increased immunogenicity, re-directed neutralization, re-directed hemagglutination, improved infection efficiency, reduced toxicity, improved replication and/or improved pharmacokinetics such as altered tissue distribution upon in vivo administration. Comparison of properties of different chimaeric adenoviruses can lead to the delineation of adenovirus elements involved in providing an adenovirus with the property. Such knowledge can then be used to further optimize nucleic acid delivery vehicles. In one aspect the invention provides a selection of (chimaeric) adenoviruses with an improved capacity to transduce macrophage- or fibroblast-like cells compared to adenovirus 5, preferably the (chimaeric) adenoviruses include at least part of a tissue tropism determining part of a fiber protein of an adenovirus of subgroup B, or a derivative and/or analogue of the fiber protein.

The invention further provides a selection of (chimaeric) adenoviruses with an improved capacity to transduce smooth muscle cells compared to adenovirus 5, preferably the (chimaeric) adenoviruses include at least part of a tissue tropism determining part of a fiber protein of an adenovirus of subgroup B, or a derivative and/or analogue of the fiber protein. A chimaeric adenovirus library of the invention may further be used to study adenovirus biology. Such a library is for instance very well suited to study differences in the biology of the various adenovirus serotypes. In one aspect the invention provides a selection of (chimaeric) adenoviruses, capable of transducing a CAR negative cell. Preferably, the CAR negative cell is an amnion fluid cell or a derivative thereof. Preferably, the amnion fluid cell is a chorion villi cell or a derivative thereof. Preferably, the CAR negative cell is a CAR negative hemopoietic cell, such as but not limited to an erythroid precursor cell and/or a monocyte precursor cell and/or derivatives thereof. Preferably, the (chimeric) adenoviruses capable of transducing a CAR negative cell include at least an adenovirus receptor binding part of a fiber protein from an adenovirus of subgroup D or F.

In one aspect, the invention provides a chimaeric adenovirus including a re-directed neutralization pattern compared to Ad5. Re-directed neutralization is useful in a number of circumstances. For instance, but not limited to, getting round pre-existing neutralizing antibodies in a patient administered with the chimaeric adenovirus. Pre-existing neutralizing antibodies would neutralize the adenovirus and thereby diminish the effective amount of virus administered. This effect is usually not desired in for instance gene therapy settings wherein a nucleic acid is to be delivered to target cells. However, pre-existing neutralizing antibodies can for instance in other gene therapy applications be an advantage when the nucleic acid of interest delivered through the chimaeric adenovirus should not be delivered to cells throughout the body. Local delivery for instance by using a needle in a solid tissue combined with the presence of neutralizing antibodies in the blood that can neutralize leaking chimaeric adenovirus can in that case help to contain the transduction to a certain area.

In another aspect, the invention provides a chimaeric adenovirus including a re-directed hemagglutination pattern compared to adenovirus 5. Re-directed hemagglutination is useful in a number of circumstances. Hemagglutinated material is preferentially taken up by macrophages and derivatives and/or precursors. Thus, enhanced hemagglutination of a chimaeric adenovirus is preferred in case where enhanced delivery of nucleic acid to the macrophages is desired. However, in general the target cell will not be the macrophages thus in those cases a reduced hemagglutination is desired. A chimaeric adenovirus re-directed in its hemagglutination is useful for many applications which the person skilled art can now think of and thus form an integral part of the present invention.

BRIEF DESCRIPTION OF THE SEVERAL VIEWS OF THE DRAWINGS

FIG. 7 depicts the fiber protein sequences of adenovirus serotypes 8 (SEQ ID NO:14), 9 (SEQ ID NO:15), 13 (SEQ ID NO:16), 14 (SEQ ID NO:17), 20 (SEQ ID NO:18), 23 (SEQ ID NO:19), 24 (SEQ ID NO:20), 25 (SEQ ID NO:21), 27 (SEQ ID NO:22), 28 (SEQ ID NO:23), 29 (SEQ ID NO:24), 30 (SEQ ID NO:25), 32 (SEQ ID NO:26), 33 (SEQ ID NO:27), 34 (SEQ ID NO:28), 35 (SEQ ID NO:29), 36 (SEQ ID NO:30), 37 (SEQ ID NO:31), 38 (SEQ ID NO:32), 39 (SEQ ID NO:33), 42 (SEQ ID NO:34), 43 (SEQ ID NO:35), 44 (SEQ ID NO:36), 45 (SEQ ID NO:37), 46 (SEQ ID NO:38), 47 (SEQ ID NO:39), 48 (SEQ ID NO:40), 49 (SEQ ID NO:41), and 51 (SEQ ID NO:42). Bold letters represent part of the tail of Ad5. If bold letters not present, it means that a PCR fragment was sequenced which did not contain the Ad5 tail. An X, present in the sequence means unidentified amino acid due to unidentified nucleotide. At the end of the sequence the stop codon of the fiber is presented by a dot.

FIG. 10 depicts the hexon protein sequences of adenovirus serotypes 34 (SEQ ID NO:43) 35 (SEQ ID NO:44) 36 (SEQ ID NO:45) and 41 (SEQ ID NO:46) An X, present in the sequence means unidentified amino acid due to unidentified nucleotide. At the end of the sequence the stop codon of the hexon is presented by a dot.

DETAILED DESCRIPTION OF THE INVENTION

Figure 1:
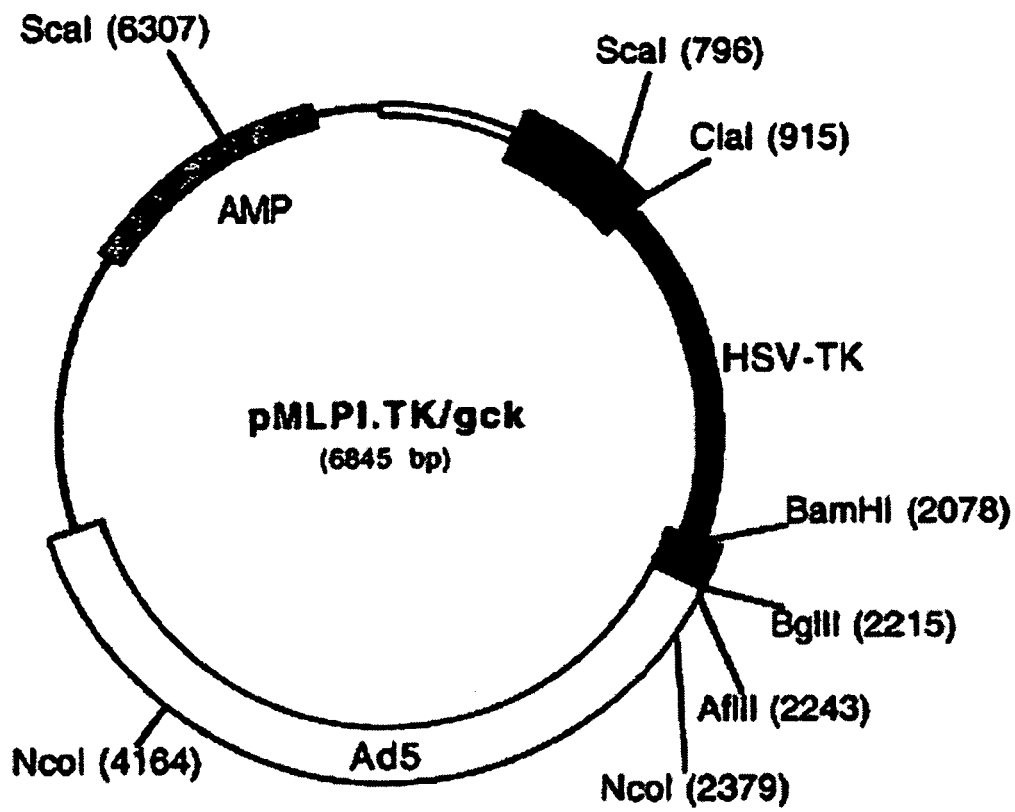
FIG. 1 schematically presents adapter plasmid pMLPI.TK.

It has been demonstrated in mice that upon in vivo systemic delivery of recombinant Ad5 for gene therapy purposes approximately 99% of the virus is trapped in the liver (Herz et al., 1993). Therefore, alteration of the Ad5 host cell range to be able to target other organs in vivo is a major interest of the invention, particularly in combination with other alterations, in particular the immunogenicity.

The initial step for successful infection is binding of adenovirus to its target cell, a process mediated through fiber protein. The fiber protein has a trimeric structure (Stouten et al., 1992) with different lengths depending on the virus serotype (Signas et al. 1985; Kidd et all 1993). Different serotypes have polypeptides with structurally similar N and C termini, but different middle stem regions. N-terminally, the first 30 amino acids are involved in anchoring of the fiber to the penton base (Chroboczek et al., 1995), especially the conserved FNPVYP region in the tail (Arnberg et al. 1997). The C-terminus, or knob, is responsible for initial interaction with the cellular adenovirus receptor. After this initial binding secondary binding between the capsid penton base and cell-surface integrins leads to internalization of viral particles in coated pits and endocytosis (Morgan et al., 1969; Svensson et al., 1984; Varga et al., 1992; Greber et al., 1993; Wickham et al., 1994). Integrins are αβ-heterodimers of which at least 14 α-subunits and 8 β-subunits have been identified (Hynes et al., 1992). The array of integrins expressed in cells is complex and will vary between cell types and cellular environment. Although the knob contains some conserved regions, between serotypes, knob proteins show a high degree of variability, indicating that different adenovirus receptors exist. For instance, it has been demonstrated that adenoviruses of subgroup C (Ad2, Ad5) and adenoviruses of subgroup B (Ad3) bind to different receptors (Defner et al., 1990). The fiber protein also contains the type specific γ-antigen, which together with the ε-antigen of the hexon determines the serotype specificity. The γ-antigen is localized on the fiber and it is known that it consists of 17 amino acids (Eiz et al., 1997). The anti-fiber antibodies of the host are therefore directed to the trimeric structure of the knob. The anti-fiber antibodies together with antibodies directed against the penton base and hexon proteins are responsible for the neutralization of adenovirus particles. First, the anti-fiber antibodies uncoat the adenovirus particles after which the penton base is accessible to the anti-penton base antibodies (Gahery-Segard et al., 1998). Although this seems to be a very effective way to neutralize adenovirus particles others have described that the anti-hexon antibodies are the most effective ones in neutralization of the particles (Gall et al., 1996).

To obtain re-directed infection of recombinant Ad5, several approaches have been or still are under investigation. Wickham et al. has altered the RGD (Arg, Gly, Asp) motif in the penton base which is believed to be responsible for the $\alpha\alpha_v\beta\beta_3$ and $\alpha_v\beta_5$ integrin binding to the penton base. They have replaced this RGD motif by another peptide motif which is specific for the $\alpha_4\beta_1$ receptor. In this way, targeting the adenovirus to a specific target cell could be accomplished (Wickham et al., 1995, 1996). Krasnykh et al. has made use of the HI loop available in the knob. This loop is, based on X-ray crystallographics, located on the outside of the knob trimeric structure and therefore is thought not to contribute to the intramolecular interactions in the knob (Krasnykh et al., 1998). However, complete CAR independent infection was not observed.

The present invention provides a method and means by which adenoviruses can be constructed with an altered immune response, or with the absence or decreased infection in antigen presenting cells such as dendritic cells or macrophages. The present invention further provides methods for the generation of chimaeric adenoviruses as described herein which can be targeted to specific cell types in vitro as well as in vivo have an altered tropism for certain cell types. The present invention further provides a method and means by which such an adenovirus can be used as a protein or nucleic acid delivery vehicle to a specific cell type or tissue.

The generation of chimaeric adenoviruses based on Ad5 with modified late genes is described. For this purpose, three plasmids, which together contain the complete Ad5 genome, were constructed. From these plasmids, the DNA encoding the Ad5 penton-base protein, hexon protein, and fiber protein were removed and replaced by linker DNA sequences which facilitate easy cloning. These plasmids subsequently served as a template for the insertion of DNA encoding for penton-base protein, hexon protein, and fiber protein derived from different adenovirus, serotypes (human or animal). The DNAs derived from the different serotypes were obtained using the polymerase chain reaction technique in combination with (degenerate) oligonucleotides. At the former E1 location in the genome of Ad5, any gene of interest can be cloned. A single transfection procedure of the three plasmids together resulted in the formation of a recombinant chimaeric adenovirus. This new technology of libraries consisting of chimaeric adenoviruses thus allows for a rapid screening for improved recombinant adenoviral vectors for in vitro and in vivo gene therapy purposes.

Although successful introduction of changes in the Ad5 fiber and penton-base have been reported, the complex structure of knob and the limited knowledge of the precise amino acids interacting with CAR render such targeting approaches laborious and difficult.

To overcome the limitations described previously, we used pre-existing adenovirus fibers, penton base proteins, and hexon proteins derived from other adenovirus serotypes. By generating chimaeric Ad5 libraries containing structural proteins of alternative adenovirus serotypes, we have developed a technology which enables rapid screening for a recombinant adenoviral vector with preferred characteristics.

In one aspect, this invention describes the use of chimaeric adenoviruses to overcome, natural existing or induced, neutralizing host activity towards recombinant adenoviruses administered in vivo for therapeutic applications. The host immune response is predominantly directed against penton base—and hexon proteins present in the adenoviral capsid and to a lesser extent directed to fiber.

The adenovirus serotypes are defined by the inability to cross-react with neutralizing antibodies in animal sera. Therefore chimaeric viruses based on for example Ad5 but chimaeric for penton base protein, and/or hexon protein provoke an altered, less severe immune response. The need for such chimaeric adenoviruses is stressed by observations that 1) repeated systemic delivery of recombinant Ad5 is unsuccessful due to formation of high titers of neutralizing antibodies against the recombinant Ad5 (Schulick et al., 1997), and 2) pre-existing or natural immunity.

This aspect of the invention therefore circumvents the inability to repeat the administration of an adenovirus for gene therapy purposes. Preferably, the penton base-, hexon-, and fiber proteins are derived from adenoviruses in subgroup B and D and are more specifically of the adenovirus serotype 16, 24, 33, 36, 38, 39, 42, and 50. This latter is because these serotypes are rarely isolated from humans indicating that low titers of circulating neutralizing antibodies are present against these serotypes.

In another aspect, this invention describes chimaeric adenoviruses and methods to generate these viruses that have an altered tropism different from that of Ad5. For example, viruses based on Ad5 but displaying any adenovirus fiber existing in nature. This chimaeric Ad5 is able to infect certain cell types more efficiently, or less efficiently in vitro and in vivo than the Ad5. Such cells include but are not limited to endothelial cells, smooth muscle cells, dendritic cells, neuronal cells, glial cells, synovical cells, lung epithelial cells, hemopoietic stem cells, monocytic/macrophage cells etc.

In another aspect, this invention describes methods which identify chimaeric adenoviruses that display improved in vitro amplification in static or suspension cell cultures. Adenoviruses derived from different subgroups, but also within one subgroup, display a high variability in productive infection in cell types that are used for production of recombinant adenovirus. Table 2 lists an overview of different adenovirus serotypes and their association with human disease, demonstrating that replication of a given adenovirus serotype is enhanced in certain cell types. For the production of recombinant adenoviruses for gene therapy purposes, several cell lines are available. These include but do not limit PER.C6, 911, 293, and E1 A549. These adenovirus producer cells may not be the most suited cell types to amplify Ad5 based viruses. Therefore, in this aspect of the invention we select adenoviruses from different serotypes based on their ability to propagate for example on PER.C6 and use their early genes (without E1) and ITRs to construct chimaeric viruses which are superior in terms of propagation and thus yield higher titers as compared to commonly used adenovirus serotype 2 or 5.

In another aspect, the invention describes the construction and use of libraries consisting of distinct parts of Ad5 in which one or more genes or sequences have been replaced with DNA derived from alternative human or animal serotypes. This set of constructs, in total encompassing the complete adenovirus genome, allows for the construction of unique chimaeric adenoviruses customized for a certain group of patients or even a single individual.

The chimeric adenoviruses may, but need not, contain deletions in the E1 region and insertions of heterologous genes linked either or not to a promoter. Furthermore, chimaeric adenoviruses may, or may not, contain deletions in the E3 region and insertions of heterologous genes linked to a promoter. Furthermore, chimaeric adenoviruses may, or may not, contain deletions in the E2 and/or E4 region and insertions of heterologous genes linked to a promoter. In the latter case E2 and/or E4 complementing cell lines are required to generate recombinant adenoviruses.

The invention is further explained with the help of the following illustrative Examples.

EXAMPLES

Example 1

Generation of Ad5 Genomic Plasmid Clones

The complete genome of Ad5 has been cloned into various plasmids or cosmids to allow easy modification of parts of the Ad5 genome, while still retaining the capability to produce recombinant virus. For this purpose the following plasmids were generated:

1. pBr/Ad.Bam-rITR (ECACC Deposit P97082122)

In order to facilitate blunt end cloning of the ITR sequences, wild-type human adenovirus type 5 (Ad5) DNA was treated with Klenow enzyme in the presence of excess dNTPs. After inactivation of the Klenow enzyme and purification by phenol/chloroform extraction followed by ethanol precipitation, the DNA was digested with BamHI. This DNA preparation was used without further purification in a ligation reaction with pBr322 derived vector DNA prepared as follows: pBr322 DNA was digested with EcoRV and BamHI, dephosphorylated by treatment with TSAP enzyme (Life Technologies) and purified on LMP agarose gel (SeaPlaque GTG). After transformation into competent *E.coli* DH5a (Life Techn.) and analysis of ampicillin resistant colonies, one clone was selected that showed a digestion pattern as expected for an insert extending from the BamHI site in Ad5 to the right ITR.

Sequence analysis of the cloning border at the right ITR revealed that the most 3' G residue of the ITR was missing, the remainder of the ITR was found to be correct. The missing G residue is complemented by the other ITR during replication.

2. pBr/Ad.Sal-rITR (ECACC Deposit P97082119)

pBr/Ad.Bam-rITR was digested with BamHI and SalI. The vector fragment including the adenovirus insert was isolated in LMP agarose (SeaPlaque GTG) and ligated to a 4.8 kb SalI-BamHI fragment obtained from wt Ad5 DNA and purified with the Geneclean II kit (Bio 101, Inc.). One clone was chosen and the integrity of the Ad5 sequences was determined by restriction enzyme analysis. Clone pBr/Ad.Sal-rITR contains adeno type 5 sequences from the SalI site at bp 16746 up to and including the rITR (missing the most 3' G residue).

3. pBr/Ad.Cla-Bam (ECACC Deposit P97082117)

wt Adeno type 5 DNA was digested with ClaI and BamHI, and the 20.6 kb fragment was isolated from gel by electro-elution. pBr322 was digested with the same enzymes and purified from agarose gel by Geneclean. Both fragments were ligated and transformed into competent DH5a. The resulting clone pBr/Ad.Cla-Bam was analyzed by restriction enzyme digestion and shown to contain an insert with adenovirus sequences from bp 919 to 21566.

4. pBr/Ad.AflII-Bam (ECACC Deposit P97082114)

Clone pBr/Ad.Cla-Bam was linearized with EcoRI (in pBr322) and partially digested with AflII. After heat inactivation of AflII for 20 minutes at 65° C. the fragment ends were filled in with Klenow enzyme. The DNA was then ligated to a blunt double stranded oligo linker containing a PacI site (5'-AATTGTCTTAATTAACCGCTTAA-3') (SEQ ID NO:47). This linker was made by annealing the following two oligonucleotides: 5'-AATTGTCTTAATTAACCGC-3' (SEQ ID NO:84) and 5'-AATTGCGGTTAATTAAGAC-3' (SEQ ID NO:85), followed by blunting with Klenow enzyme. After precipitation of the ligated DNA to change buffer, the ligations were digested with an excess PacI enzyme to remove concatamers of the oligo. The 22016 bp partial fragment containing Ad5 sequences from bp 3534 up to 21566 and the vector sequences, was isolated in LMP agarose (SeaPlaque GTG), religated and transformed into competent DH5a. One clone that was found to contain the PacI site and that had retained the large adeno fragment was selected and sequenced at the 5' end to verify correct insertion of the PacI linker in the (lost) AflII site.

5. pBr/Ad.Bam-rITRpac#2 (ECACC Deposit P97082120) and pBr/Ad.Bam-rITR#8 (ECACC Deposit P97082121)

To allow insertion of a PacI site near the ITR of Ad5 in clone pBr/Ad.Bam-rITR, about 190 nucleotides were removed between the ClaI site in the pBr322 backbone and the start of the ITR sequences. This was done as follows: pBr/Ad.Bam-rITR was digested with ClaI and treated with nuclease Bal31 for varying lengths of time (2 minutes, 5 minutes, 10 minutes and 15 minutes). The extent of nucleotide removal was followed by separate reactions on pBr322 DNA (also digested at the ClaI site), using identical buffers and conditions. Bal31 enzyme was inactivated by incubation at 75° C. for 10 minutes, the DNA was precipitated and resuspended in a smaller volume of TE buffer. To ensure blunt ends, DNAs were further treated with T4 DNA polymerase in the presence of excess dNTPs. After digestion of the (control) pBr322 DNA with SalI, satisfactory degradation (~150 bp) was observed in the samples treated for 10 minutes or 15 minutes. The 10 minutes or 15 minutes treated pBr/Ad.Bam-rITR samples were then ligated to the above described blunted PacI linkers (See pBr/Ad.AflII-Bam). Ligations were purified by precipitation, digested with excess PacI and separated from the linkers on an LMP agarose gel. After religation, DNAs were transformed into competent DH5a and colonies analyzed. Ten clones were selected that showed a deletion of approximately the desired length and these were further analyzed by T-track sequencing (T7 sequencing kit, Pharmacia Biotech). Two clones were found with the PacI linker inserted just downstream of the rITR. After digestion with PacI, clone #2 has 28 bp and clone #8 has 27 bp attached to the ITR.

6. pWE/Ad.AflII-rITR (ECACC Deposit P97082116)

Cosmid vector pWE15 (Clontech) was used to clone larger Ad5 inserts. First, a linker containing a unique PacI site was inserted in the EcoRI sites of pWE15 creating pWE.pac. To this end, the double stranded PacI oligo as described for pBr/Ad.AflII-BamHI was used but now with its EcoRI protruding ends. The following fragments were then isolated by electro-elution from agarose gel: pWE.pac digested with PacI, pBr/AflII-Bam digested with PacI and BamHI and pBr/Ad.Bam-rITR#2 digested with BamHI and PacI. These fragments were ligated together and packaged using 1 phage packaging extracts (Stratagene) according to the manufacturer's protocol. After infection into host bacteria, colonies were grown on plates and analyzed for presence of the complete insert. pWE/Ad.AflII-rITR contains all adenovirus type 5 sequences from bp 3534 (AflII site) up to and including the right ITR (missing the most 3' G residue).

7. pBr/Ad.lITR-Sal(9.4) (ECACC Deposit P97082115)

Adeno 5 wt DNA was treated with Klenow enzyme in the presence of excess dNTPs and subsequently digested with SalI. Two of the resulting fragments, designated left ITR-Sal (9.4) and Sal(16.7)-right ITR, respectively, were isolated in LMP agarose (Seaplaque GTG). pBr322 DNA was digested with EcoRV and SalI and treated with phosphatase (Life Technologies). The vector fragment was isolated using the Geneclean method (BIO 101, Inc.) and ligated to the Ad5 SalI fragments. Only the ligation with the 9.4 kb fragment gave colonies with an insert. After analysis and sequencing of the cloning border a clone was chosen that contained the full ITR sequence and extended to the SalI site at bp 9462.

8. pBr/Ad.lITR-Sal(16.7) (ECACC Deposit P97082118)

pBr/Ad.lITR-Sal(9.4) is digested with SalI and dephosphorylated (TSAP, Life Technologies). To extend this clone up to the third SalI site in Ad5, pBr/Ad.Cla-Bam was linearized with BamHI and partially digested with SalI. A 7.3 kb SalI fragment containing adenovirus sequences from 9462-16746 was isolated in LMP agarose gel and ligated to the SalI-digested pBr/Ad.lITR-Sal(9.4) vector fragment.

9. pWE/Ad.AflII-EcoRI pWE.pac was digested with ClaI and 5' protruding ends were filled using Klenow enzyme. The DNA was then digested with PacI and isolated from agarose gel. pWE/AflII-rITR was digested with EcoRI and after treatment with Klenow enzyme digested with PacI. The large 24 kb fragment containing the adenoviral sequences was isolated from agarose gel and ligated to the ClaI-digested and blunted pWE.pac vector using the Ligation Express™ kit from Clontech. After transformation of Ultracompetent XL10 -Gold cells from Stratagene, clones were identified that contained the expected insert. pWE/AflII-EcoRI contains Ad5 sequences from bp 3534-27336.

10. Construction of New Adapter Plasmids

The absence of sequence overlap between the recombinant adenovirus and E1 sequences in the packaging cell line is essential for safe, RCA-free generation and propagation of new recombinant viruses. The adapter plasmid pMLPI.TK (FIG. 1) is an example of an adapter plasmid designed for use according to the invention in combination with the improved packaging cell lines of the invention. This plasmid was used as the starting material to make a new vector in which nucleic acid molecules including specific promoter and gene sequences can be easily exchanged.

First, a PCR fragment was generated from pZipΔΔMo+PyF101(N⁻) template DNA (described in PCT/NL96/00195) with the following primers: LTR-1: 5'-CTG TAC GTA CCA GTG CAC TGG CCT AGG CAT GGA AAA ATA CAT AAC TG-3' (SEQ ID NO:48)and LTR-2: 5'-GCG GAT CCT TCG AAC CAT GGT AAG CTT GGT ACC GCT AGC GTT AAC CGG GCG ACT CAG TCA ATC G-3' (SEQ ID NO:49). Pwo DNA polymerase (Boehringer Mannheim) was used according to manufacturers protocol with the following temperature cycles: once 5 minutes at 95° C.; 3 minutes at 55° C.; and 1 minute at 72° C., and 30 cycles of 1 minute at 95° C. 1 minute at 60° C., 1 minute at 72° C., followed by once 10 minutes at 72° C. The PCR product was then digested with BamHI and ligated into pMLP10 (Levrero et al., 1991) vector digested with PvuII and BamHI, thereby generating vector pLTR10. This vector contains adenoviral sequences from bp 1 up to bp 454 followed by a promoter consisting of a part of the Mo-MuLV LTR having its wild-type enhancer sequences replaced by the enhancer from a mutant polyoma virus (PyF101). The promoter fragment was designated L420. Next, the coding region of the murine HSA gene was inserted. pLTR10 was digested with BstBI followed by Klenow treatment and digestion with NcoI. The HSA gene was obtained by PCR amplification on pUC18-HSA (Kay et al., 1990) using the following primers: HSA1, 5'-GCG CCA CCA TGG GCA GAG CGA TGG TGG C-3' (SEQ ID NO:50)and HSA2, 5'-GTT AGA TCT AAG CTT GTC GAC ATC GAT CTA CTA ACA GTA GAG ATG TAG AA-3' (SEQ ID NO:51). The 269 bp amplified fragment was subcloned in a shuttle vector using the NcoI and BglII sites. Sequencing confirmed incorporation of the correct coding sequence of the HSA gene, but with an extra TAG insertion directly following the TAG stop codon. The coding region of the HSA gene, including the TAG duplication was then excised as a NcoI (sticky)-SalI (blunt) fragment and cloned into the 3.5 kb NcoI(sticky)/BstBI(blunt) fragment from pLTR10, resulting in pLTR-HSA10.

Figure 2:
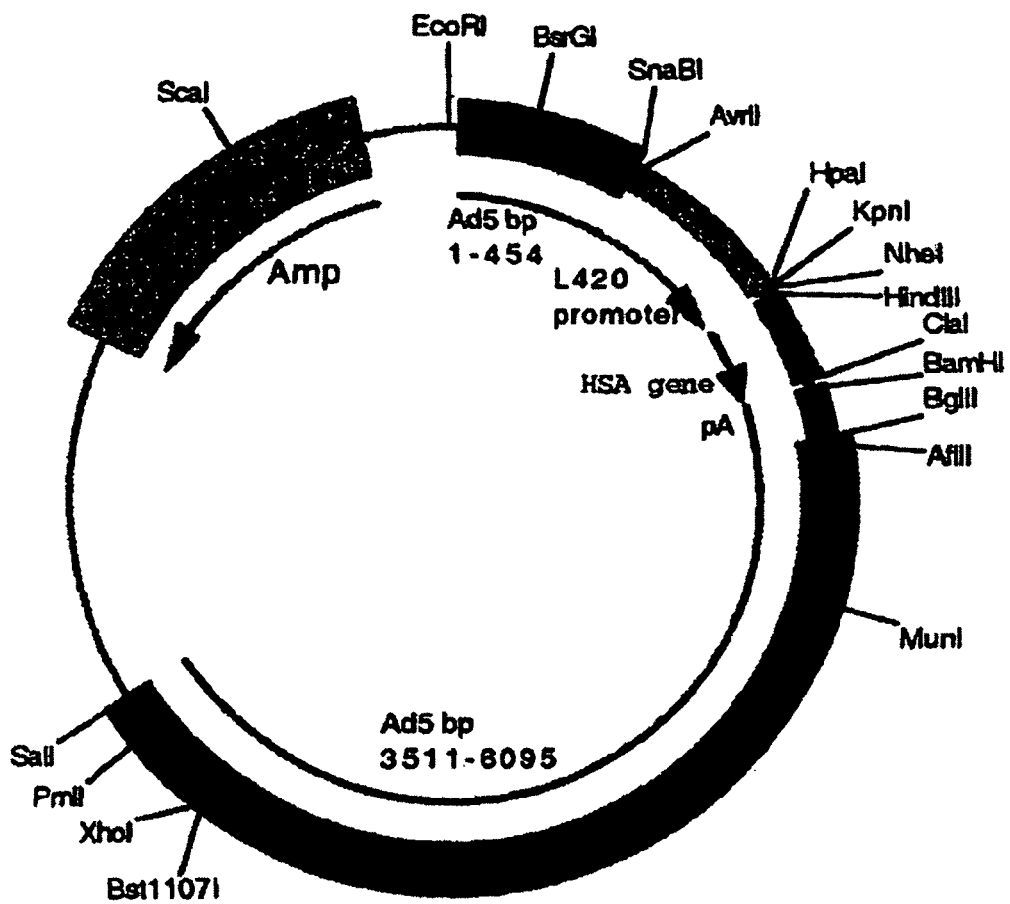
FIG. 2 schematically presents adapter plasmid pAd/L420-HSA.

Finally, pLTR-HSA10 was digested with EcoRI and BamHI after which the fragment containing the left ITR, packaging signal, L420 promoter and HSA gene was inserted into vector pMLPI.TK digested with the same enzymes and thereby replacing the promoter and gene sequences. This resulted in the new adapter plasmid pAd/L420-HSA (FIG. 2) that contains convenient recognition sites for various restriction enzymes around the promoter and gene sequences. SnaBI and AvrII can be combined with HpaI, NheI, KpnI, HindIII to exchange promoter sequences, while the latter sites can be combined with the ClaI or BamHI sites 3' from HSA coding region to replace genes in this construct.

Figure 3:
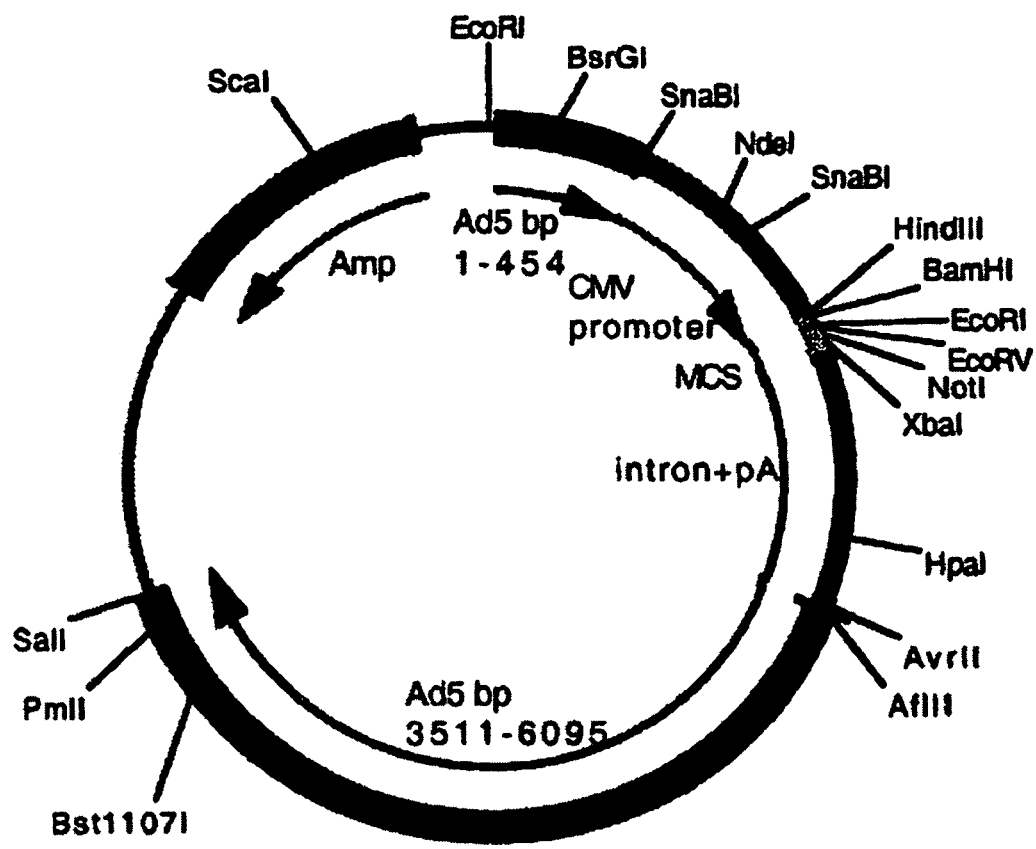
FIG. 3 schematically presents adapter plasmid pAd5/CLIP.

Another adapter plasmid that was designed to allow easy exchange of nucleic acid molecules was made by replacing the promoter, gene and poly A sequences in pAd/L420-HSA with the CMV promoter, a multiple cloning site, an intron and a poly-A signal. For this purpose, pAd/L420-HSA was digested with AvrII and BglII followed by treatment with Klenow to obtain blunt ends. The 5.1 kb fragment with pBr322 vector and adenoviral sequences was isolated and ligated to a blunt 1570 bp fragment from pcDNA1/amp (Invitrogen) obtained by digestion with HhaI and AvrII followed by treatment with T4 DNA polymerase. This adapter plasmid was named pCLIP.Luc (FIG. 3).

11. Generation of Recombinant Adenoviruses

To generate E1-deleted recombinant adenoviruses with the new plasmid-based system, the following constructs are prepared:

a) An adapter construct containing the expression cassette with the gene of interest linearized with a restriction enzyme that cuts at the 3' side of the overlapping adenoviral genome fragment, preferably not containing any pBr322 vector sequences, and b) A complementing adenoviral genome construct pWE/Ad.AflII-rITR digested with PacI.

Figure 4:
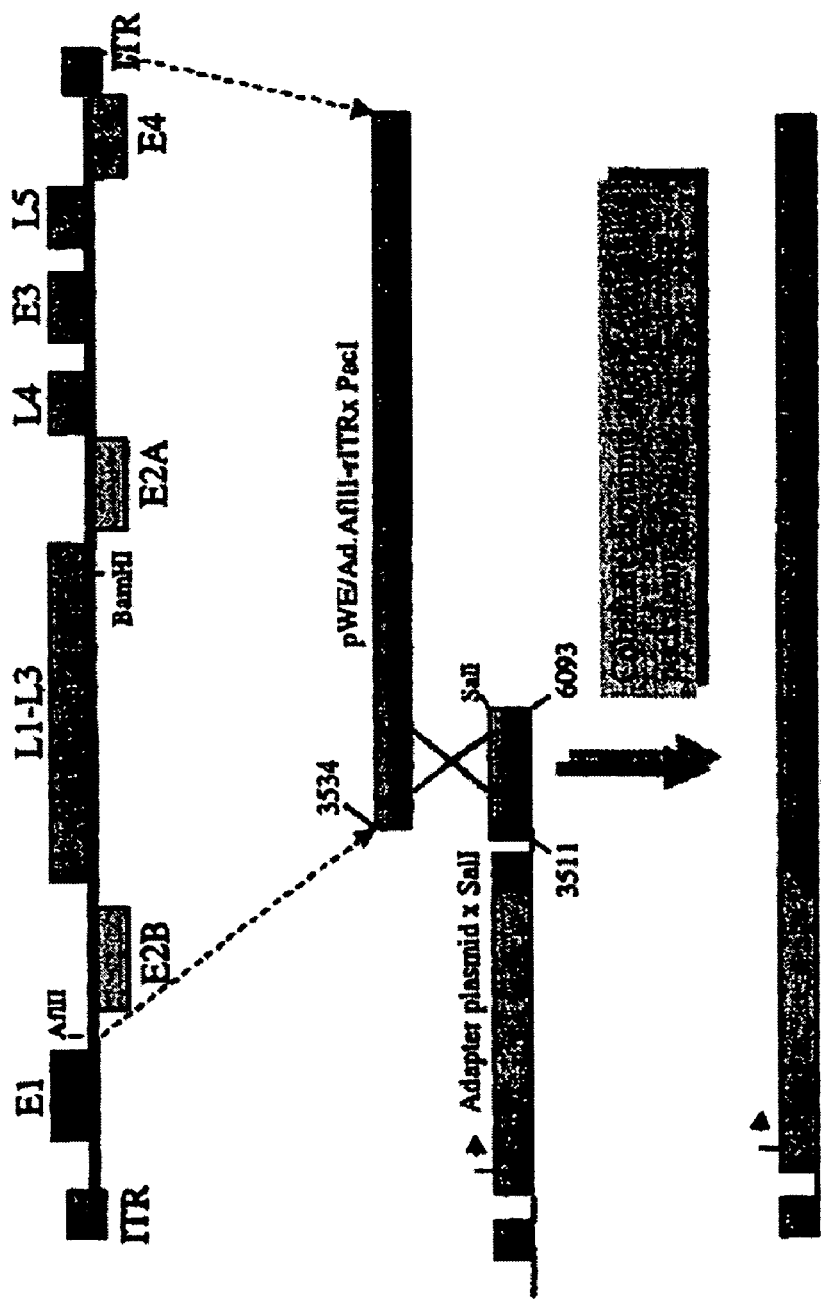
FIG. 4 schematically presents a two plasmid system for the generation of recombinant adenoviruses.

These two DNA molecules are further purified by phenol/chloroform extraction and EtOH precipitation. Co-transfection of these plasmids into an adenovirus packaging cell line, preferably a cell line according to the invention, generates recombinant replication deficient adenoviruses by a one-step homologous recombination between the adapter and the complementing construct (FIG. 4).

Figure 5:
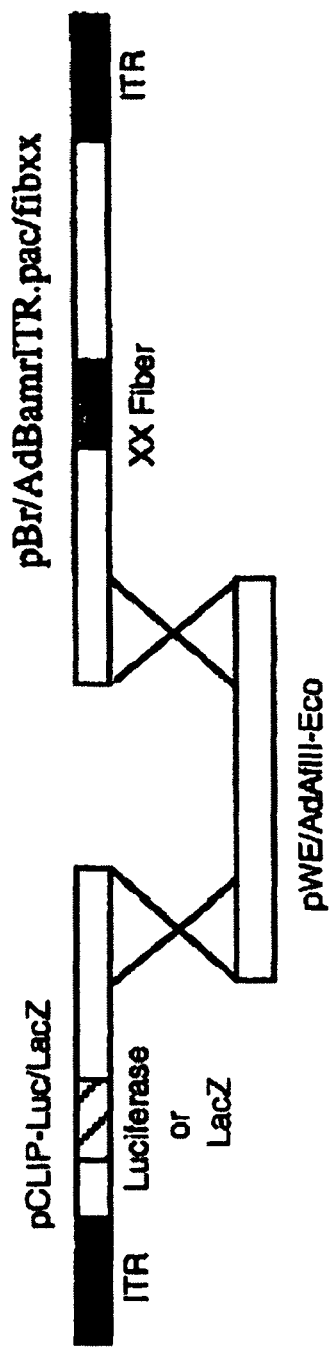
FIG. 5 schematically presents a three plasmid system for the generation of recombinant adenoviruses.

Alternatively, instead of pWE/Ad.AflII-rITR, other fragments can be used, e.g., pBr/Ad.Cla-Bam digested with EcoRI and BamHI or pBr/Ad.AflII-BamHI digested with PacI and BamHI can be combined with pBr/Ad.Sal-rITR digested with SalI. In this case, three plasmids are combined and two homologous recombinations are needed to obtain a recombinant adenovirus (FIG. 5). It is to be understood that those skilled in the art may use other combinations of adapter and complementing plasmids without departing from the present invention.

A general protocol as outlined below and meant as a non-limiting example of the present invention has been performed to produce several recombinant adenoviruses using various adapter plasmids and the Ad.AflIIrITR fragment. Adenovirus packaging cells (PER.C6) were seeded in ~25 cm$^2$ flasks and the next day when they were at ~80% confluency, transfected with a mixture of DNA and lipofectamine agent (Life Techn.) as described by the manufacturer. Routinely, 40 µl lipofectamine, 4 µg adapter plasmid and 4 µg of the complementing adenovirus genome fragment AflII-rITR (or 2 µg of all three plasmids for the double homologous recombination) are used. Under these conditions transient transfection efficiencies of ~50% (48 hrs post transfection) are obtained as determined with control transfections using a pAd/CMV-LacZ adapter. Two days later, cells are passaged to ~80 cm$^2$ flasks and further cultured. Approximately five (for the single homologous recombination) to eleven days (for the double homologous recombination) later a cytopathogenic effect (CPE) is seen, indicating that functional adenovirus has formed. Cells and medium are harvested upon full CPE and recombinant virus is released by freeze-thawing. An extra amplification step in an 80 cm$^2$ flask is routinely performed to increase the yield since at the initial stage the titers are found to be variable despite the occurrence of full CPE. After amplification, viruses are harvested and plaque purified on PER.C6 cells. Individual plaques are tested for viruses with active transgenes.

Besides replacements in the E1 region, it is possible to delete or replace (part of) the E3 region in the adenovirus because E3 functions are not necessary for the replication, packaging and infection of the (recombinant) virus. This creates the opportunity to use a larger insert or to insert more than one gene without exceeding the maximum package size (approximately 105% of wt genome length). This can be done, e.g., by deleting part of the E3 region in the pBr/Ad.Bam-rITR clone by digestion with XbaI and religation. This removes Ad5 wt sequences 28592-30470 including all known E3 coding regions. Another example is the precise replacement of the coding region of gp19K in the E3 region with a polylinker allowing insertion of new sequences. This, 1) leaves all other coding regions intact and 2) obviates the need for a heterologous promoter since the transgene is driven by the E3 promoter and pA sequences, leaving more space for coding sequences.

To this end, the 2.7 kb EcoRI fragment from wt Ad5 containing the 5' part of the E3 region was cloned into the EcoRI site of pBluescript (KS$^-$) (Stratagene). Next, the HindIII site in the polylinker was removed by digestion with EcoRV and HincII and subsequent religation. The resulting clone pBS.Eco-Eco/ad5DIII was used to delete the gp19K coding region. Primers 1 (5'-GGG TAT TAG GCC AA AGG CGC A-3') (SEQ ID NO:52) and 2 (5'-GAT CCC ATG GAA GCT TGG GTG GCG ACC CCA GCG-3') (SEQ ID NO:53) were used to amplify a sequence from pBS.Eco-Eco/Ad5DIII corresponding to sequences 28511 to 28734 in wt Ad5 DNA. Primers 3 (5'-GAT CCC ATG GGG ATC CTT TAC TAA GTT ACA AAG CTA-3') (SEQ ID NO:54) and 4 (5'-GTC GCT GTA GTT GGA CTG G-3') (SEQ ID NO:55) were used on the same DNA to amplify Ad5 sequences from 29217 to 29476. The two resulting PCR fragments were ligated together by virtue of the new introduced NcoI site and subsequently digested with XbaI and MunI. This fragrnent was then ligated into the pBS.Eco-Eco/ad5ΔΔHIII vector that was digested with XbaI (partially) and MunI generating pBS.Eco-Eco/ad5ΔHIII.Δgp19K. To allow insertion of foreign genes into the HindIII and BamHI site, an XbaI deletion was made in pBS.Eco-Eco/ad5ΔHIII.Δgp19K to remove the BamHI site in the Bluescript polylinker. The resulting plasmid pBS.Eco-Eco/ad5ΔHIIIAgp19KΔΔXbaI, contains unique HindIII and BamHI sites corresponding to sequences 28733 (HindIII) and 29218 (BamHI) in Ad5. After introduction of a foreign gene into these sites, either the deleted XbaI fragment is re-introduced, or the insert is recloned into pBS.Eco-Eco/ad5ΔHIII.Δgp19K using HindIII and for example MunI. Using this procedure, we have generated plasmids expressing HSV-TK, hIL-1a, rat IL-3, luciferase or LacZ. The unique SrfI and NotI sites in the pBS.Eco-Eco/ad5ΔHIII.Δgp19K plasmid (with or without inserted gene of interest) are used to transfer the region including the gene of interest into the corresponding region of pBr/Ad.Bam-rITR, yielding construct pBr/Ad.Bam-rITRΔΔgp19K (with or without inserted gene of interest). This construct is used as described supra to produce recombinant adenoviruses. In the viral context, expression of inserted genes is driven by the adenovirus E3 promoter.

Recombinant viruses that are both E1- and E3-deleted are generated by a double homologous recombination procedure as described above for E1-replacement vectors using a plasmid-based system consisting of:
  a) an adapter plasmid for E1 replacement according to the invention, with or without insertion of a first gene of interest,
  b) the pWE/Ad.AflII-EcoRI fragment, and
  c) the pBr/Ad.Bam-rITRΔgp19K plasmid with or without insertion of a second gene of interest.

In addition to manipulations in the E3 region, changes of (parts of) the E4 region can be accomplished easily in pBr/Ad.Bam-rITR. Generation and propagation of such a virus, however, in some cases demands complementation in trans.

Example 2

Generation of Ad5 Based Viruses With Chimaeric Fiber Proteins

The method described infra to generate recombinant adenoviruses by co-transfection of two, or more separate cloned adenoviral sequences. These cloned adenoviral sequences were subsequently used to remove specific Ad5 sequences in order to generate template clones which allow for the easy introduction of DNA sequences derived from other adenovirus serotypes. As an example of these template clones, the construction of plasmids enabling swapping of DNA encoding for fiber protein is given below.

Generation of Adenovirus Template Clones Lacking DNA Encoding Fiber

Figure 6:
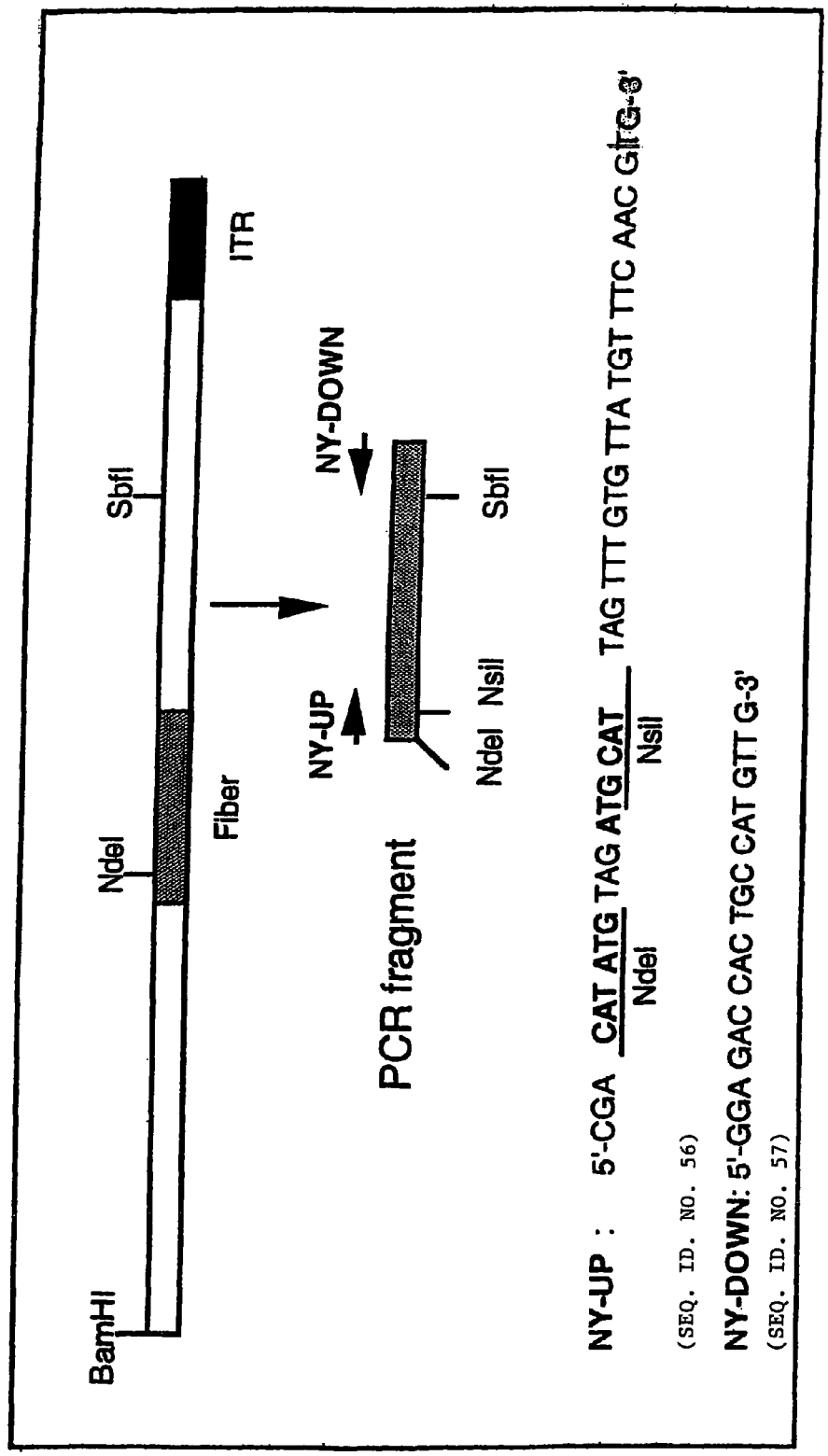
FIG. 6 schematically presents the generation of plasmid pBr/AdBamRDeltaFib in which part of the Adenovirus type 5 fiber DNA is replaced by a short DNA stretch containing a unique NsiI site.

The fiber coding sequence of Ad5 is located between nucleotides 31042 and 32787. To remove the Ad5 DNA encoding fiber we started with construct pBr/Ad.Bam-rITR. First, a NdeI site was removed from this construct. For this purpose, pBr322 plasmid DNA was digested with NdeI after which protruding ends were filled using Klenow enzyme. This pBr322 plasmid was then re-ligated, digested with NdeI and transformed into *E. coli* DH5αα. The obtained pBr/ΔΔNdeI plasmid was digested with ScaI and SalI and the resulting 3198 bp vector fragment was ligated to the 15349 bp ScaI-SalI fragment derived from pBr/Ad.BamrITR, resulting in plasmid pBr/Ad.Bam-rITRΔΔNdeI which hence contained a unique NdeI site. Next a PCR was performed with oligonucleotides NY-up: 5'-CGA CAT ATG TAG ATGCAT TAG TTT GTG TTA TGT TTC AAC GTG-3' (SEQ ID NO:56) and NY-down: 5'-GGA GAC CAC TGC CAT GTT-3' (SEQ ID NO:57) (FIG. 6). During amplification, both a NdeI (bold face) and a NsiI restriction site (underlined) were introduced to facilitate cloning of the amplified fiber DNAs. Amplification consisted of 25 cycles of each 45 sec. at 94° C., 1 min. at 60° C., and 45 sec. at 72° C. The PCR reaction contained 25 pmol of oligonucleotides NY-up or NY-down, 2 mM dNTP, PCR buffer with 1.5 mM MgCl$_2$, and 1 unit of Elongase heat stable polymerase (Gibco, The Netherlands). One-tenth of the PCR product was run on an agarose gel which demonstrated that the expected DNA fragment of ±2200 bp was amplified. This PCR fragment was subsequently purified using Geneclean kit system (Bio101 Inc.). Then, both the construct pBr/Ad.Bam-rITRΔNdeI as well as the PCR product were digested with restriction enzymes NdeI and SbfI. The PCR fragment was subsequently cloned using T4 ligase enzyme into the NdeI and SbfI digested pBr/Ad.Bam-rITRΔNdeI, generating pBr/Ad.BamRΔFib. This plasmid allows insertion of any PCR amplified fiber sequence through the unique NdeI and NsiI sites that are inserted in place of the removed fiber sequence. Viruses can be generated by a double homologous recombination in packaging cells described infra using an adapter plasmid, construct pBr/Ad.AflII-EcoRI digested with PacI and EcoRI and a pBr/Ad.BamRΔFib construct in which heterologous fiber sequences have been inserted. To increase the efficiency of virus generation, the construct pBr/Ad.BamRΔFib was modified to generate a PacI site flanking the right ITR. Hereto, pBr/Ad.BamRΔFib was digested with AvrII and the 5 kb adeno fragment was isolated and introduced into the vector pBr/Ad.Bam-rITR.pac#8 replacing the corresponding AvrII fragment. The resulting construct was named pBr/Ad.BamRΔFib.pac. Once a heterologous fiber sequence is introduced in pBr/Ad.BamRΔFib.pac, the fiber modified right hand adenovirus clone may be introduced into a large cosmid clone as described for pWE/Ad.AflII-rITR in Example 1. Such a large cosmid clone allows generation of adenovirus by only one homologous recombination making the process extremely efficient.

Amplification of Fiber Sequences from Adenovirus Serotypes

To enable amplification of the DNAs encoding fiber protein derived from alternative serotypes degenerate oligonucleotides were synthesized. For this purpose, first known DNA sequences encoding fiber protein of alternative serotypes were aligned to identify conserved regions in both the tail-region as well as the knob-region of the fiber protein. From the alignment, which contained the nucleotide sequence of 19 different serotypes representing all 6 subgroups, (degenerate) oligonucleotides were synthesized (see Table 3). Also shown in table 3 is the combination of oligonucleotides used to amplify the DNA encoding fiber protein of a specific serotype. The amplification reaction (50 µl) contained 2 mM dNTPs, 25 pmol of each oligonucleotide, standard 1× PCR buffer, 1.5 mM MgCl$_2$, and 1 Unit Pwo heat stable polymerase (Boehringer) per reaction. The cycler program contained 20 cycles, each consisting of 30 sec. 94° C., 60 sec. 60-64° C., and 120 sec. at 72° C. One-tenth of the PCR product was run on an agarose gel which demonstrated that a DNA fragment was amplified. Of each different template, two independent PCR reactions were performed after which the independent PCR fragments obtained were sequenced to determine the nucleotide sequence. From 11 different serotypes, the nucleotide sequence could be compared to sequences present in GenBank. Of all other serotypes, the DNA encoding fiber protein was unknown till date and was therefore aligned with known sequences from other subgroup members to determine homology i.e.,sequence divergence. Of the 51 human serotypes known to date, all fiber sequences, except for serotypes 1, 6, and 26, have been amplified and sequenced. The protein sequences of the fiber from different adenovirus serotypes is given in FIG. 7.

Generation of Fiber Chimaeric Adenoviral DNA Constructs

All amplified fiber DNAs as well as the vector (pBr/Ad.BamRΔΔFib) were digested with NdeI and NsiI. The digested DNAs were subsequently run on an agarose gel after which the fragments were isolated from the gel and purified using the Geneclean kit (Bio101 Inc). The PCR fragments were then cloned into the NdeI and NsiI sites of pBr/AdBamRΔΔFib, thus generating pBr/AdBamRFibXX (where XX stands for the serotype number of which the fiber DNA was isolated). So far the fiber sequence of serotypes 5/ 7/ 8/ 9/ 10/ 11/ 12/ 13/ 14/ 16/ 17/ 19/ 21/ 24/ 27/ 28/ 29/ 30/ 32/ 33/ 34/ 35/ 36/ 37/ 38/ 40-S/ 40-L/ 41-S/ 42/45/ 47/ 49/ 51 have been cloned into pBr/AdBamRFibXX. From pBr/AdBamRFibXX (where XX is 5/ 8/ 9/ 10/ 11/ 13/ 16/ 17/ 24/ 27/ 30/ 32/ 33/ 34/ 35/ 38/ 40-S/ 40-L/ 45/ 47/ 49/ 51) an 6 kb AvrII fragment encompassing the fiber sequence was isolated via gelelectrophoresis and GeneClean. This AvrII fragment was subsequently cloned in plasmid pBr/Ad.Bam-rITR.pac (see Example 1) which was digested to completion with AvrII and dephosphorylated as described previously, leading to the generation of the plasmid pBr/Ad.Bam-rITR.pac.fibXX. This plasmid was subsequently used to generate a cosmid clone with a modified fiber using the constructs pWE.pac, pBr/AflII-Bam and pBr/Ad.Bam-rITR.pac.fibXX. This cosmid cloning resulted in the formation of construct pWE/Ad.AflII-rITR/FibXX (where XX stands for the serotype number of which the fiber DNA was isolated).

Generation of pAd5/L420.HSA, pAd5/Clip and pAd5/Clipsal pMLPI.TK was used to make a new vector in which nucleic acid molecules including specific promoter and gene sequences can be easily exchanged.

First, a PCR fragment was generated from pZipΔMo+PyF101(N⁻) template DNA (described in International Patent Application PCT/NL96/00195) with the following primers: LTR-1: 5'-CTG TAC GTA CCA GTG CAC TGG CCT AGG CAT GGA AAA ATA CAT AAC TG-3' (SEQ ID NO:58) and LTR-2: 5'-GCG GAT CCT TCG AAC CAT GGT AAG CTT GGT ACC GCT AGC GTT AAC CGG GCG ACT CAG TCA ATC G-3' (SEQ ID NO:59). Pwo DNA polymerase (Boehringer Mannheim) was used according to manufacturers protocol with the following temperature cycles: once 5 minutes at 95° C.; 3 minutes at 55° C.; and 1 minute at 72° C., and 30 cycles of 1 minute at 95° C., 1 minute at 60° C., 1 minute at 72° C., followed by once 10 minutes at 72° C. The PCR product was then digested with BamHI and ligated into pMLP10 (Levrero et al., 1991; Gene 101, 195-202) digested with PvuII and BamHI, thereby generating vector pLTR10. This vector contains adenoviral sequences from bp 1 up to bp 454 followed by a promoter consisting of a part of the Mo-MuLV LTR having its wild-type enhancer sequences replaced by the enhancer from a mutant polyoma virus (PyF101). The promoter fragment was designated L420. Sequencing confirmed correct amplification of the LTR fragment however the most 5' bases in the PCR fragment were missing so that the PvuII site was not restored. Next, the coding region of the murine HSA gene was inserted. pLTR10 was digested with BstBI followed by Klenow treatment and digestion with NcoI. The HSA gene was obtained by PCR amplification on pUC18-HSA (Kay et al., 1990; J. Immunol. 145, 1952-1959) using the following primers: HSA1, 5'-GCG CCA CCA TGG GCA GAG CGA TGG TGG C-3' (SEQ ID NO:60) and HSA2, 5'-GTT AGA TCT AAG CTT GTC GAC ATC GAT CTA CTA ACA GTA GAG ATG TAG AA-3' (SEQ ID NO:61). The 269 bp amplified fragment was subcloned in a shuttle vector using the NcoI and BglII sites. Sequencing confirmed incorporation of the correct coding sequence of the HSA gene, but with an extra TAG insertion directly following the TAG stop codon. The coding region of the HSA gene, including the TAG duplication was then excised as a NcoI (sticky)-SalI(blunt) fragment and cloned into the 3.5 kb NcoI (sticky)/BstBI(blunt) fragment from pLTR10, resulting in pLTR-HSA10.

Finally, pLTR-HSA10 was digested with EcoRI and BamHI after which the fragment containing the left ITR, packaging signal, L420 promoter and HSA gene was inserted into vector pMLPI.TK digested with the same enzymes and thereby replacing the promoter and gene sequences. This resulted in the new adapter plasmid pAd5/L420-HSA that contains convenient recognition sites for various restriction enzymes around the promoter and gene sequences. SnaBI and AvrII can be combined with HpaI, NheI, KpnI, HindIII to exchange promoter sequences, while the latter sites can be combined with the ClaI or BamHI sites 3' from HSA coding region to replace genes in this construct.

Another adapter plasmid that was designed to allow easy exchange of nucleic acid molecules was made by replacing the promoter, gene and polyA sequences in pAd5/L420-HSA with the CMV promoter, a multiple cloning site, an intron and a polyA signal. For this purpose, pAd5/L420-HSA was digested with AvrII and BglII followed by treatment with Klenow to obtain blunt ends. The 5.1 kb fragment with pBr322 vector and adenoviral sequences was isolated and ligated to a blunt 1570 bp fragment from pcDNA1/amp (Invitrogen) obtained by digestion with HhaI and AvrII followed by treatment with T4 DNA polymerase. This adapter plasmid was named pAd5/Clip. To enable removal of vector sequences from the adenoviral fragment pAd5/Clip was partially digested with EcoRI and the linear fragment was isolated. An oligo of the sequence 5' TTAAGTCGAC-3' (SEQ ID NO:62) was annealed to itself resulting in a linker with a SalI site and EcoRI overhang. The linker was ligated to the partially digested pAd5/Clip vector and clones were selected that had the linker inserted in the EcoRI site 23 bp upstream of the left adenovirus ITR in pAd5/Clip resulting in pAd5/Clipsal.

Generation of pAd5ClipLacZ, pAd5Clip.Luc, pAd5Clip.TK and pAd5Clipsal.Luc

The adapter plasmid pAd5/Clip.LacZ was generated as follows: The E.coli LacZ gene was amplified from the plasmid pMLP.nlsLacZ (EPO Patent Application 95-202 213) by PCR with the primers 5'GGGGTGGCCAGGGTAC-CTCTAGGCTTTTGCAA (SEQ ID NO:63) and 5'GGGGG-GATCCATAAACAAGTTCAGAATCC(SEQ ID NO:64). The PCR reaction was performed Ex Taq (Takara) according to the suppliers protocol at the following amplification program: 5 minutes 94° C., 1 cycle; 45 seconds 94° C. and 30 seconds 60° C. and 2 minutes 72° C., 5 cycles; 45 seconds 94° C. and 30 seconds 65° C. and 2 minutes 72° C., 25 cycles; 10 minutes 72; 45 seconds 94° C. and 30 seconds 60° C. and 2 minutes 72° C., 5 cycles, I cycle. The PCR product was subsequently digested with Kpn1 and BamHI and the digested DNA fragment was ligated into KpnI/BamHI digested pcDNA3 (Invitrogen), giving rise to pcDNA3.nlsLacZ. Next, the plasmid pAd5/Clip was digested with SpeI. The large fragment containing part of the 5' part CMV promoter and the adenoviral sequences was isolated. The plasmid pcDNA3.nlsLacZ was digested with SpeI and the fragment containing the 3' part of the CMV promoter and the lacZ gene was isolated. Subsequently, the fragments were ligated, giving rise to pAd/Clip.LacZ. The reconstitution of the CMV promoter was confirmed by restriction digestion.

The adapter plasmid pAd5/Clip.Luc was generated as follows: The plasmid pCMV.Luc (EPO Patent Application 95-202 213) was digested with HindHI and BamHI. The DNA fragment containing the luciferase gene was isolated. The adapter plasmid pAd5/Clip was digested with HindIII and BamHI, and the large fragment was isolated. Next, the isolated DNA fragments were ligated, giving rise to pAd5/Clip.Luc. The adapter pClipsal.Luc was generated in the same way but using the adapter pClipsal digested with HIII and BamHI as vector fragment. Likewise, the TK containing HIII-BamHI fragment from pCMV.TK (EPO Patent Application 95-202 213) was inserted in pClipsal to generate pAd5/Clip.TK. The presence of the SalI site just upstream of the left ITR enables liberation of vector sequences from the adeno insert. Removal of these vector sequences enhances frequency of vector generation during homologous recombination in PER.C6.

Generation of Recombinant Adenovirus Chimeric for Fiber Protein

To generate recombinant Ad 5virus carrying the fiber of serotype 12, 16,28,40-L, 51, and 5, three constructs, pCLIP.Luc, pWE/AdAflII-Eco and pBr/AdBamrITR.pac/fibXX (XX=12, 16, 28, 40-L, 51, and 5) were transfected into adenovirus producer cells. To generate recombinant Ad 5 virus carrying the fiber of 5/ 7/ 8/ 9/ 10/ 11/ 12/ 13/ 14/ 16/ 17/ 19/ 21/ 24/27/ 28/ 29/ 30/ 32/ 33/ 34/ 35/ 36/ 37/ 38/ 40-S/ 40-L/ 41-S/ 42/45/ 47/ 49/ 51, two constructs pCLIP.Luc and pWE/Ad.AflII-rITR/FibXX were transfected into adenovirus producer cells.

For transfection, 2 µg of pCLIP.Luc, and 4 µg of both pWE/AdAflII-Eco and pBr/AdBamrITR.pac/fibXX (or in case of cosmids: 4 µg of pCLIP.Luc plus 4 µg of pWE/Ad.AflII-rITR/FibXX) were diluted in serum free DMEM to 100 µl total volume. To this DNA suspension 100 µl 1× diluted lipofectamine (Gibco) was added. After 30 minutes at room temperature the DNA-lipofectamine complex solution was added to 2.5 ml of serum-free DMEM which was subsequently added to a T25 cm$^2$ tissue culture flask. This flask contained 2×10$^6$ PER.C6 cells that were seeded 24-hours prior to transfection. Two hours later, the DNA-lipofectamine complex containing medium was diluted once by the addition of 2.4 ml DMEM supplemented with 20% fetal calf serum. Again 24 hours later the medium was replaced by fresh DMEM supplemented with 10% fetal calf serum. Cells were cultured for 6-8 days, subsequently harvested, and freeze/thawed 3 times. Cellular debris was removed by centrifugation for 5 minutes at 3000 rpm room temperature. Of the supernatant (12.5 ml) 3-5 ml was used to infect again infect PER.C6 cells (T80 cm$^2$ tissue culture flasks). This re-infection results in full CPE after 5-6 days after which the adenovirus is harvested as described above. With the generated virus batch two assays were routinely performed. 1) 20 µl virus supernatant, diluted 10-fold by the addition of 1980 µl DMEM was used to infect A549 cells that were seeded 24-hours prior to infection at a concentration of 10$^5$ cells per well of 6-well plates. Forty-eight hours later protein lysates were prepared that were subsequently used to measure marker gene expression (luciferase activity). 2) 20 µl virus supernatant is used to determine the virus titer on human 911 cells. For this purpose, 911 cells are seeded at a concentration of 4×10$^4$ cells per well in 96-well plates. Three to four hours after seeding, the medium was replaced by adenovirus supernatant (dilution range: 2 µl-5×10$^{-9}$ µl). The virus titers of the chimeric fiber Ad5 always exceeded 1×10$^8$ infectious units per ml.

Example 3

Production, Purification, and Titration of Chimeric Adenoviruses

Of the supernatant obtained from transfected PER.C6 cells, typically 10 ml was used to inoculate a 1 liter fermentor which contained 1- 1.5×10$^6$ cells/ ml PER.C6 that were specifically adapted to grow in suspension. Three days after inoculation, the cells were harvested and pelleted by centrifuging for 10 min at 1750 rpm at room temperature. The chimeric adenoviruses present in the pelleted cells were subsequently extracted and purified using the following downstream processing protocol. The pellet was dissolved in 50 ml 10 mm NaPO$_4^-$ and frozen at −20° C. After thawing at 37° C., 5.6 ml deoxycholate (5% w/v) was added afterwhich the solution was homogenated. The solution was subsequently incubated for 15 minutes at 37° C. to crack the cells. After homogenizing the solution, 1875 µl (1M) MgCl$_2^-$ was added and 5 ml 100% glycerol. After the addition of 375 µl DNase (10 mg/ml) the solution was incubated for 30 minutes at 37° C. Cell debris was removed by centrifugation at 1880×g for 30 minutes at room temperature without the brake on. The supernatant was subsequently purified from proteins by loading on 10 ml of FREON. Upon centrifugation for 15 minutes at 2000 rpm without break at room temperature, three bands were visible of which the upper band represents the adenovirus. This band was isolated by pipetting after which it was loaded on a Tris/HCl (1M) buffered caesium chloride block gradient (range: 1.2 to 1.4 gr./ml). Upon centrifugation at 21000 rpm for 2.5 hours at 10° C. the virus was purified from remaining protein and cell debris since the virus, in contrast to the other components, did not migrate into the 1.4 gr./ml cesium chloride solution. The virus band was isolated after which a second purification using a Tris/HCl (1M) buffered continues gradient of 1.33 gr./ml of cesium chloride is performed. After virus loading on top of this gradient the virus was centrifuged for 17 hours at 55000 rpm at 10° C. Subsequently the virus band was isolated and after the addition of 30 µl of sucrose (50 w/v) excess cesium chloride is removed by three rounds of dialysis, each round including of 1 hour. For dialysis the virus is transferred to dialysis slides (Slide-a-lizer, cut off 10000 kDa, Pierce, USA). The buffers used for dialysis are PBS which are supplemented with an increasing concentration of sucrose (round 1 to 3: 30 ml, 60 ml, and 150 ml sucrose (50% w/v)/ 1.5 liter PBS, all supplemented with 7.5 ml 2% (w/v) CaMgCl$_2$). After dialysis, the virus is removed from the slide-a-lizer after which it is aliquoted in portions of 25 and 100 µl upon which the virus is stored at −85° C.

To determine the number of virus particles per milliliter, 50 µl of the virus batch is run on an high performance liquid chromatograph columns (HPLC). The adenovirus is bound to the column (anion exchange) after which it is eluted using a NaCl gradient (range 300-600 mm). By determining the area under the virus peak, the number of virus particles can be calculated. To determine the number of infectious units (IU) per ml present in a virus batch, titrations are performed on 911 cells. For this purpose, $4 \times 10^4$ 911 cells are seeded per well of 96-well plates in rows B, D, and F in a total volume of 100 µl per well. Three hours after seeding the cells are attached to the plastic support after which the medium can be removed. To the cells a volume of 200 µl is added, in duplicate, containing different dilutions of virus (range: $10^2$ times diluted to $2 \times 10^9$). By screening for CPE the highest virus dilution which still renders CPE after 14 days is considered to contain at least one infectious unit. Using this observation, together with the calculated amount of virus volume present in these wells renders the number of infectious units per ml of a given virus batch. The production results i. e., virus particles per ml and IU per ml or those chimeric adenoviruses that were produced so far, are shown in Table 4.

Example 4

Re-directed Infection of Chimeric Adenoviruses

To demonstrate re-directed infection in vitro of the adenoviruses chimeric for fiber protein, a panel of human cell lines of different origins was used. This panel includes, amongst others, human hepatic cells, primary fibroblasts, hemopoietic derived cell lines, primary smooth muscle cells, primary synoviocytes, and primary cells derived from the amniotic fluid such as amniocytes and chorion villi. These cell types were infected with a panel of chimeric adenoviruses which differ in the fiber protein. For this purpose, target cells are seeded at a concentration of $10^5$ cells per well of 6-well plates in 2 ml Dulbecco's modified Eagle's medium (DMEM, Life Technologies, NL) supplemented with 10% Fetal calf serum. Twenty-four hours later the medium is replaced by fresh medium containing the different chimeric adenoviruses at an increasing MOI of 0, 10, 50, 250, 1250, 2500, 5000 (MOI based on virus particles per cell). Approximately 2 hours after the addition of virus the medium containing the virus is discarded, cells are washed once with PBS, and subsequently 2 ml of fresh medium (not containing virus) is added to each well. Forty-eight hours later cells are harvested, washed and pelleted by centrifuging 5 minutes at 1500 rpm. Cells are subsequently lysed in 0.1 ml lysis buffer (1% Triton-X-100, 15% Glycerol, 2 mm EDTA, 2 mm DTT, and 25 mm MgCl$_2$ in Tris-phosphate buffer pH 7.8) after which the total protein concentration of the lysate is measured (Biorad, protein standard II). To determine marker gene expression (luciferase activity) 20 µl of the protein sample is mixed with 100 µl of a luciferase substrate (Luciferine, Promega, NL) and subsequently measured on a Lumat LB 9507 apparatus (EG & G Berthold, NL). The results of these infection experiments, given as the amount of luciferase activity (RLU) per µg protein, are shown in Table 5. These results clearly demonstrate that alteration of the fiber protein results in alteration of the Ad5 host range.

Example 5

Receptor Usage of Fiber Chimeric Adenoviruses

To determine what cellular molecules are used by the fiber chimeric adenoviruses the expression of proteins known to be involved in Ad5 infection i.e., Coxsackie adenovirus receptor (CAR), MHC class I, and integrins ($\Delta v\beta 3$, $\alpha v\beta 5$) was measured. For this purpose, $1 \times 10^5$ target cells were transferred to tubes (4 tubes per cell type) designed for flow cytometry. Cells were washed once with PBS/0.5% BSA after which the cells were pelleted by centrifugation for 5 minutes at 1750 rpm at room temperature. Subsequently, 10 µl of a 100 times diluted $\alpha_v\beta 3$ antibody (Mab 1961, Brunswick Chemie, Amsterdam, NL), a 100 times diluted antibody $\alpha_v\beta 5$ (antibody (Mab 1976, Brunswick Chemie), or 2000 times diluted CAR antibody (a kind gift of Dr. Bergelson, Harvard Medical School, Boston, USA (Hsu et al)) was added to the cell pellet after which the cells were incubated for 30 minutes at 4° C. in a dark environment. After this incubation, cells were washed twice with PBS/0.5% BSA and again pelleted by centrifugation for 5 minutes at 1750 rpm room temperature. To label the cells, 10 µl of rat anti mouse IgG1 labeled with phycoerythrine (PE) was added to the cell pellet upon which the cells were again incubated for 30 minutes at 4° C. in a dark environment. Finally the cells were washed twice with PBS/0.5% BSA and analyzed on a flow cytometer. The results of these experiments are shown in Table 6. Also, in Table 6 the infection efficiency of an adenovirus from subgroup A, B, C, D, and F is incorporated. These data clearly show that infection of a subgroup C adenovirus correlates with expression of CAR. The data also demonstrate that the chimeric adenoviruses carrying a fiber of an adenovirus of subgroup B, D, or F can infect cells that do not express measurable levels of the CAR protein thus being able to infect cells via different (CAR-independent) pathways.

Example 6

Radio-labeling of Adenovirus Particles

To enable tracking of infection of the wild type adenovirus serotypes, these viruses were labeled with radioactive $I^{123}$/ $I^{125}$ or with fluorescent probes prior to infection. Using fluorescent microscopy or by measuring radioactivity, the efficiency of infection of different serotypes into particular cell types is determined.

To demonstrate re-directed infection in vivo of adenovirus chimeric for fiber protein, $1 \times 10^9$ infectious particles were injected via the tail vein into CBA/ca mice (2 mice for each chimeric adenovirus). Detection of adenovirus infection into specific tissues is monitored on two different levels: 1) Binding of chimeric adenovirus is monitored by radioactive labeling the adenovirus (Eisenlohr et al., 1987; Matlin et al., 1981; Richman et al., 1998). One hour after in vivo systemic delivery via the tail vein mice are sacrificed after which preferred is investigated by measuring radioactivity in various organs c.q. tissues. 2) Successful infection is monitored by adenovirus gene expression of the marker gene i.e.,lacZ or luciferase activity. Four days after administration mice are sacrificed after which organs and tissues are isolated. Samples included liver, spleen, gastrointestinal tract, peripheral blood, bone marrow, aorta, muscle etc. Using this strategy, preferred binding of chimeric adenovirus towards tissues of interest can be investigated. Moreover, using this strategy, preferred infection of chimeric adenovirus into specific cells of particular organs can be determined.

80 μCi $I^{123}$ (Cygne BV, NL) or $I^{125}$ (Amersham) was activated by incubation for six minutes at RT in an Iodogen pre-coated tube (Pierce) in 100 μl iodination buffer (25 mm Tris, pH8, 0.4 M NaCl). The Radio-labeling reaction was started by transferring the activated Iodide to an Eppendorf tube containing $1,5.10^{10}$ adenovirus particles in 100 μl iodination buffer. The reaction was allowed to proceed for nine minutes at RT, after which incorporated label was separated from free label by gel filtration, using a Sephadex 25 column (P-10, Pharmacia). To this end, a P-10 column was pre-washed with 10 ml PBS buffer and subsequently loaded with the radio-labeling reaction, supplemented with two ml of iodination buffer. After discarding the first flow-through, the column was eluted with PBS buffer in 0.5 ml steps, and the different fractions were collected in separate tubes. Free label, which is slowed down by the column, was concentrated in fractions 10-16. Radio-labeled virus particles accumulated predominantly in fractions 4, 5 and 6, corresponding to a total eluted volume of 2-3 ml. The radioactivity of these virus-containing fractions was measured and expressed as counts per minute (cpm), resulting in up to $5.10^6$ cpm per $10^{10}$ virus particles.

Several control experiments were conducted to ensure the integrity of the virus particles after the various manipulations. For instance, one reaction was included in which the virus particles underwent identical treatment but with the omission of radioactive Iodide. Eluted virus particles were subsequently used to infect A549 cells. The amount of infected cells was established by the expression of a visual marker gene such as LacZ. In addition, small aliquots of those eluted fractions that represented radio-labeled adenovirus were used to infect A549 cells to test the expression of the transgene, which was taken as an indication for virus viability of the specific virus batch used.

The radio-labeled virus particles can subsequently be used for various in vitro and in vivo studies to determine the affinity for different cell types or for different organs. For in vitro studies, different cell lines such as for instance HUVEC (human umbilical vein endothelial cells) or SMC (smooth muscle cells) are seeded in 24-well plates in the appropriate culture medium, and infected with radio-labeled adenovirus particles at a MOI of 10, 100 and 1000. As a control, cells are incubated with a similar amount of free Iodide. Two hours after infection, cells are extensively washed with PBS buffer, and the remaining radioactivity measured. The amount of radioactivity that remains associated with the cells, corrected for the amount of radioactivity of the control cells incubated with free label, is a direct measure for the amount of virus that is attached to or has penetrated the cells.

Figure 8:
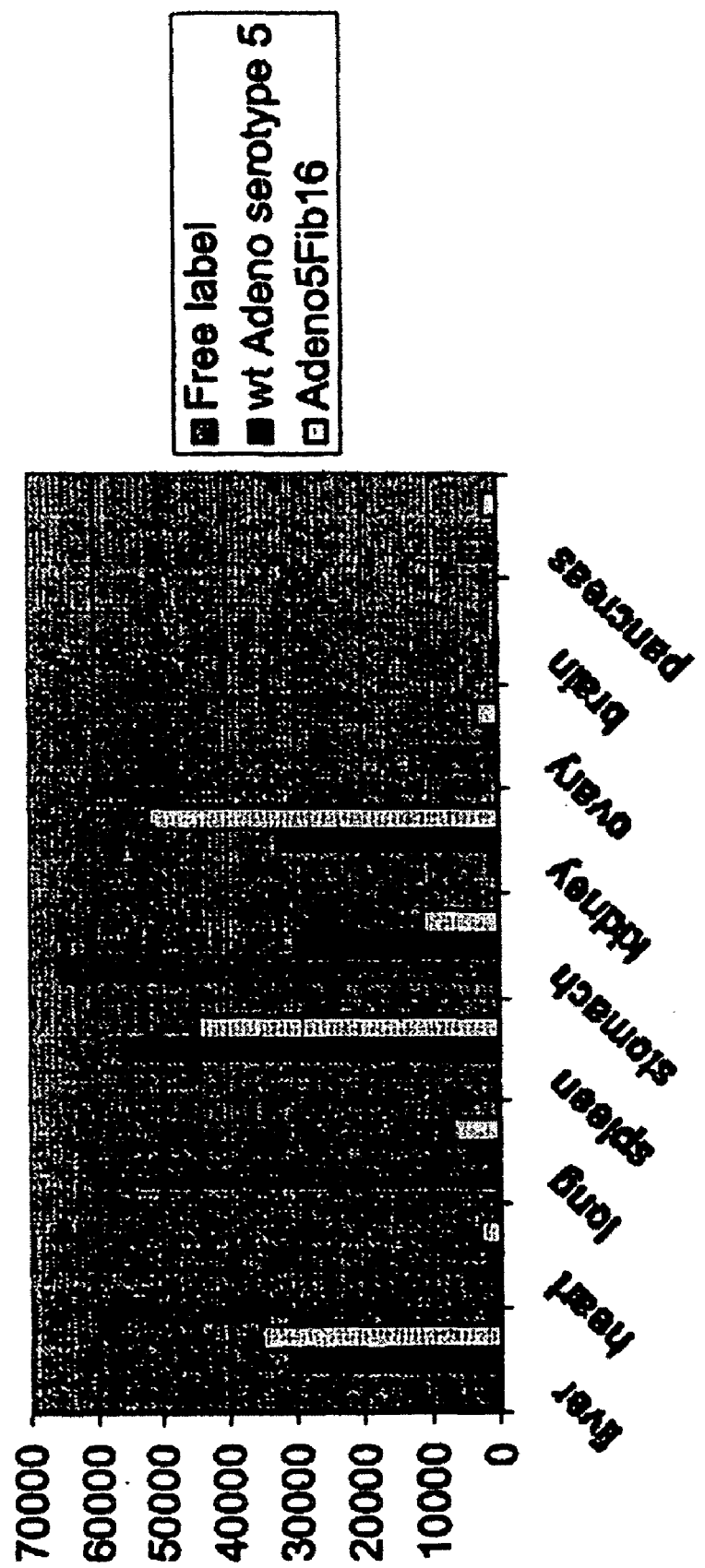
FIG. 8 compares the in vivo bio-distribution of I$^{123}$ labeled Ad5 and an adenovirus chimeric for fiber protein. Radio-labeled adenovirus ($10^{10}$ virus particles, 0.1-2 MBq) was intravenously administered into the tail vein. As a control, a similar amount of free label was injected into the control animal. Rats were sacrificed after one hour and organs calibrated. Radioactivity of the in the figure indicated organs was measured with a scintillation counter and is expressed as counts per minute per gram tissue.
Figure 9:
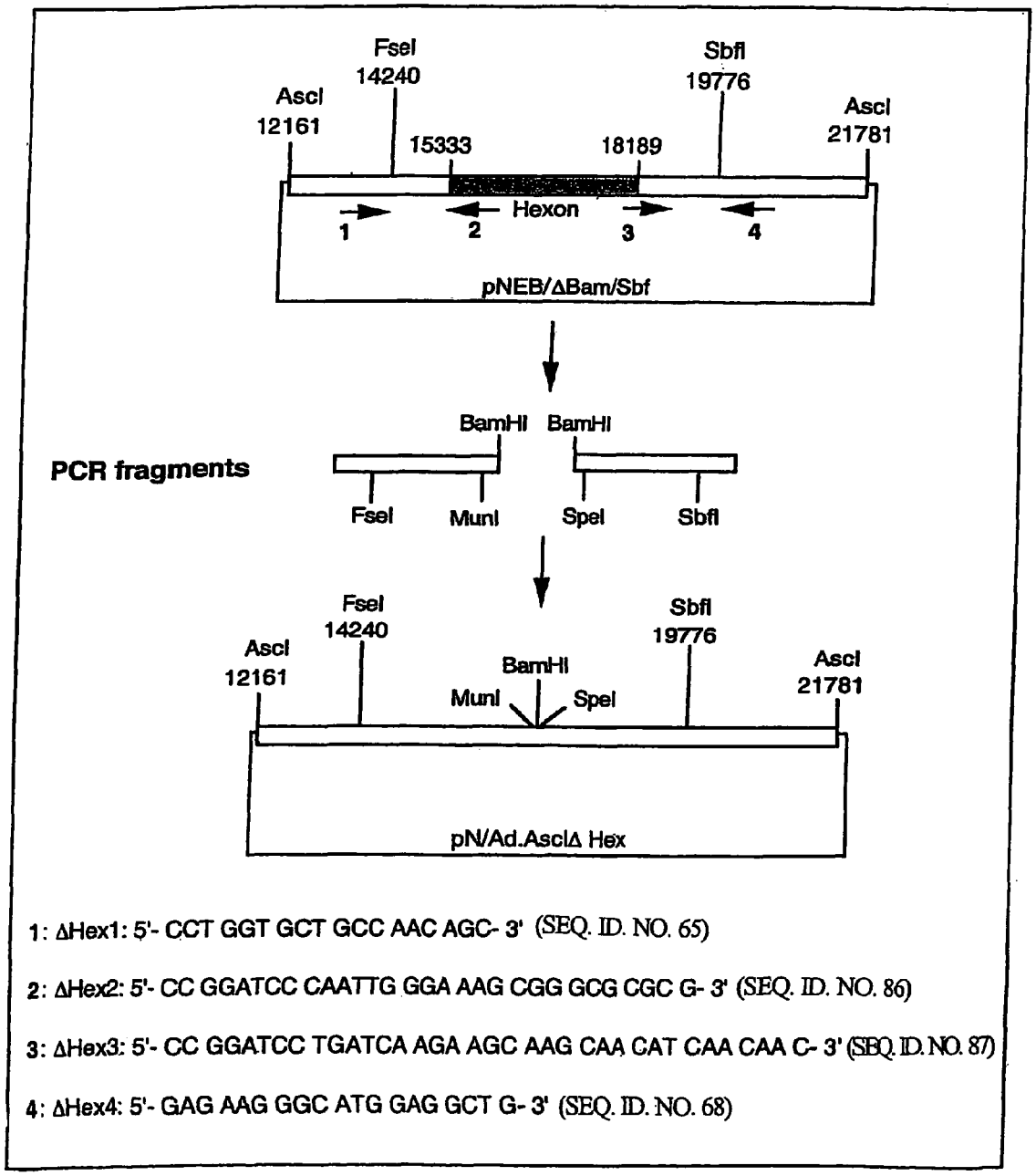
FIG. 9 schematically presents the generation of plasmid pBr/Ad.Eco-PmeΔHexon. Also shown is the sequence of the oligonucleotides delta hex 1-4 used to delete the DNA encoding for the hexon of Ad5 protein.

For in vivo studies, the bio-distribution of adenoviruses that differ only in the origin of their fiber proteins was compared. To this end, rats were placed under general anesthetic and 0.1-2 MBq of radio-labeled adenovirus particles was intravenously (iv) administered into the tail vein. As a control, one rat received a comparable dose of free Iodide only. The animals were subsequently placed onto a gamma scanner and scanned for 10 minutes, to localize the source of the gamma radiation and thus to determine the in vivo bio-distribution of systemically introduced adenovirus. After one hour, animals were sacrificed and the major organs removed for weighing and for accurate quantification of radioactivity using a scintillation counter. The distribution of radioactivity in various organs after iv is expressed as cpm per gram tissue, and is shown in FIG. 8.

Example 7

Infection of Human Primary Cells From Amniotic Fluid

In Table 5 (Example 4) infection results are shown on both amniotic cells and chorion villi. These cell types are isolated from the amniotic fluid and cultured ex vivo under standard conditions (Roest et al., 1996). Such cells are ideal targets to use for prenatal diagnosis. For instance, in some cases (approximately 50-100 yearly) prenatal diagnosis of muscular dystrophin is impossible using standard techniques such as reverse-transcribed PCR or DNA PCR because the mutations in the dystrophin gene are unknown and the level of dystrophin produced in non-differentiated chorionvilli or amnion-villi cells is very low. In these cases isolation and fast differentiation of predominantly chorionvilli cells is performed. These chorionvilli are subsequently infected with a retrovirus (Roest et al., 1996) or an adenovirus carrying the MyoD cDNA (Roest et al., 1999) which, upon transduction, triggers the chorionvilli to differentiate into striated muscle cells within one week. After complete differentiation these cells can then be used for Western analysis, or immunohistochemistry to determine whether the dystrophin protein is expressed. To date, the infection efficiency of chorionvilli cells has been disappointing with only 2-5% of cells transduced with a retrovirus (Roest et al., 1996). Using a serotype 5 adenovirus to deliver the MyoD cDNA to chorionvilli approximately 10%-20% (Roest et al., 1999) of the cells can be transduced but only when using high multiplicity of infection ("MOI") which results in undesired toxicity and thus cell death. The results in Table 5 clearly demonstrate that the Ad5 is not an ideal candidate for transducing chorionvilli cells since only marginal luciferase activity is measured (75 RLU/μg protein) at the highest MOI tested (MOI=5000 virus particles per cell). These results are confirmed using flow cytometry for the presence of the Coxsackie adenovirus receptor (CAR) and integrins which demonstrates that the receptors for Ad5 are only marginally present on chorionvilli (Table 6). Surprisingly, the Ad5 based vector containing a fiber of either subgroup B (fiber 16 and/or 51) or subgroup F (fiber 40-L) both transduce the chorionvilli with high efficiency. The vector which does best, based on luciferase activity is the adenovirus 5 with fiber 40-L which results in 1,688,028 relative light units per μg of protein, >20,000 fold increased transgene expression as compared to Ad5. This vector can thus be used to transduce cells present in the amniotic fluid to allow fast differentiation for purposes described above, for inhibiting gene expression during prenatal development, or to transfer and express nucleic acid of interest to the amniotic fluid.

Example 8

Generation of Ad5 Based Viruses with Chimeric Hexon Protein

The method described infra to generate recombinant adenoviruses by co-transfection of two, or more separate cloned adenovirus sequences. These cloned adenoviral sequences were subsequently used to remove specific Ad5 sequences in order to generate template clones which allow for the easy introduction of DNA sequences derived from other adenovirus serotypes. As an example of these template clones, the construction of plasmids enabling swapping of DNA encoding for hexon protein is given.

Generation of Adenovirus Template Clones Lacking DNA Encoding for Hexon

Hexon coding sequences of Ad5 are located between nucleotides 18841 and 21697. To facilitate easy exchange of hexon coding sequences from alternative adenovirus serotypes into the Ad5 backbone, first a shuttle vector was generated. This subclone, coded pBr/Ad.Eco-PmeI, was generated by first digesting plasmid pBr322 with EcoRI and EcoRV and inserting the 14 kb PmeI-EcoRI fragment from pWE/Ad.AflII-Eco. In this shuttle vector a deletion was made of a 1430 bp SanDI fragment by digestion with SanDI and religation to give pBr/Ad.Eco-PmeI ΔSanDI. The removed fragment contains unique SpeI and MunI sites. From pBr/Ad.Eco-PmeIΔSanDI the Ad5 DNA encoding hexon was deleted. Hereto, the hexon flanking sequences were PCR amplified and linked together thereby generating unique restriction sites replacing the hexon coding region. For these PCR reactions four different oligonucleotides were required:

Δhex1-Δhex4. Δhex1:

(SEQ ID NO:65)

5'-CCT GGT GCT GCC AAC AGC-3'

Δhex2:

(SEQ ID NO:66)

5'-CCG GAT CCA CTA GTG GAA AGC GGG CGC GCG-3'

Δhex3:

(SEQ ID NO:67)

5'-CCG GAT CCA ATT GAG AAG CAA GCA ACA TCA ACA AC-3'

Δhex4:

(SEQ ID NO:68)

5'-GAG AAG GGC ATG GAG GCT G-3'

(See FIG. 9).

The amplified DNA product of ±1100 bp obtained with oligonucleotides Δhex1 and Δhex2 was digested with BamHI and FseI. The amplified DNA product of ±1600 bp obtained with oligonucleotides Δhex3 and Δhex4 was digested with BamHI and SbfI. These digested PCR fragments were subsequently purified from agarose gel and in a tri-part ligation reaction using T4 ligase enzyme linked to pBr/Ad.Eco-PmeI ΔSanDI digested with FseI and SbfI. The resulting construct was coded pBr/Ad.Eco-PmeΔHexon. This construct was sequenced in part to confirm the correct nucleotide sequence and the presence of unique restriction sites MunI and SpeI.

Amplification of Hexon Sequences from Adenovirus Serotypes

To enable amplification of the DNAs encoding hexon protein derived from alternative serotypes degenerate oligonucleotides were synthesized. For this purpose, first known DNA sequences encoding for hexon protein of alternative serotypes were aligned to identify conserved regions in both the N-terminus as well as the C-terminus of the Hexon protein. From the alignment, which contained the nucleotide sequence of 9 different serotypes representing 5 of the 6 known subgroups, (degenerate) oligonucleotides were synthesized. These oligonucleotides were coded HEX-up (5'-GG ACGTGT AAG ATG GCY ACC CCH TCG ATG MTG-3') (SEQ ID NO:69)and HEX-down (5'-CCA TCG ATG GTT ATG TKG TKG CGT TRC CGG C-3') (SEQ ID NO:70). The amplification reaction (50 μl) contained 2 mM dNTPs, 25 pmol of each oligonucleotide, standard 1× PCR buffer, 1.5 mM $MgCl_2$, and 1 Unit Pwo heat stable polymerase (Boehringer) per reaction. The cycler program contained 20 cycles, each consisting of 30 sec. 94° C., 60 sec. 60-64° C., and 120 sec. At 72° C. One-tenth of the PCR product was run on an agarose gel which demonstrated that a DNA fragment was amplified. Of each different template, two independent PCR reactions were performed after which the independent PCR fragments obtained were sequenced to determine the nucleotide sequence. From 9 different serotypes, the nucleotide sequence could be compared to sequences present in GenBank. Of all other serotypes, the nucleotide sequence encoding the Hexon protein is unknown. So far, of each serotype, except for serotypes 1, 8, 13, and 18, the hexon sequence has been PCR amplified. The protein sequence of the hexon of serotypes 34, 35, 36, and 41 is given in FIG. 10.

Generation of Hexon Chimaeric Adenoviral DNA Constructs

All amplified hexon DNAs as well as the vector (pBr/Ad.Eco-PmeΔHexon) were digested with MunI and SpeI. The digested DNAs was subsequently run on a agarose gel after which the fragments were isolated from the gel and purified using the Geneclean kit (Bio101 Inc). The PCR fragments were then cloned into the MunI and SpeI sites of pBr/Ad.Eco-PmeΔHexon, thus generating pBr/Ad.Eco-PmeΔHexXX (where XX stands for the serotype number of which the fiber DNA was isolated). So far the hexon sequence of serotypes 2, 3, 4, 5, 7, 9, 10, 11, 14, 15, 16, 19, 20, 22, 23, 25, 26, 27, 28, 29, 30, 31, 32, 33, 34, 35, 36, 37, 38, 40, 41, 42, 43, 46, 47, 48, 49, 50, 51 have been cloned into pBr/Ad.Eco-PmeΔHexXX. From pBr/Ad.Eco-PmeΔHexXX (where XX is 20, 25, 26, 28, 30, 34, 35) a 9.6 kb AscI fragment encompassing the hexon sequence was isolated via gel electrophoresis and an agarase protocol (Boehringer Mannheim, NL). This AscI fragment was subsequently cloned in cosmid pWE/Ad.AflII-rITRsp (see, Example 1) which was digested to completion with AscI and deposphorylated as described previously. This cosmid cloning resulted in the formation of construct pWE/Ad.AflII-rITR/HexXX (where XX stands for the serotype number of which the hexon DNA was isolated).

Generation of Recombinant Adenovirus Chimeric for Hexon Protein

To generate recombinant Ad 5 virus carrying the hexon of alternative serotypes two constructs, pCLIP.Luc, pWE/Ad.AflII-rITR/HexXX were transfected into adenovirus producer cells. For transfection, 4 μg of pCLIP.Luc, and 4 μg of pWE/Ad.AflII-rITR/HexXX were diluted in serum free DMEM to 100 μl total volume. To this DNA suspension 100 μl ⅔× diluted lipofectamine (Gibco) was added. After 30 minutes at room temperature the DNA-lipofectamine complex solution was added to 2.5 ml of serum-free DMEM which was subsequently added to a T25 $cm^2$ tissue culture flask (cells washed with 5 ml serum free medium prior to addition of DNA-lipofectamine complex). This flask contained $3\times10^6$ PER.C6 cells that were seeded 24-hours prior to transfection. Two hours later, the DNA-lipofectamine complex containing medium was diluted once by the addition of 2.5 ml DMEM supplemented with 20% fetal calf serum. Again 24 hours later the medium was replaced by fresh DMEM supplemented with 10% fetal calf serum. Cells were cultured for 6-8 days, subsequently harvested, and freeze/thawed. Cellular debris was removed by centrifugation for 5 minutes at 3000 rpm room temperature. Of the supernatant (12.5 ml) 3-5 ml was used to again infect PER.C6 cells (T80 $cm^2$ tissue culture flasks).

Re-directed Neutralization Towards Hexon Chimeric Adenovirus

To demonstrate an altered immune response towards chimeric adenoviruses, we first tested 75 sera derived from human patients (25 cancer patients, 50 rheumatoid arthritis patients) for toxicity on human 911 cells. For this purpose, 911 cells were seeded at a concentration of $3 \times 10^4$ cells per well in 96-well microtiter plates. Twenty-four hours later the medium of all wells, except for wells A1-H1, A5-H5, and A9-H9, was replaced by 50 µl DMEM supplemented with 5% fetal calf serum. To wells A1, A2, B1, and B2, 50 µl patient serum 1 was added. Likewise, to wells C1, C2, D1, and D2, 50 µl of patient serum 2 was added etc. Subsequently, 50 µl of wells A2-H2 were transferred to A3-H3 after which 50 µl of wells A3-H3 was transferred to A4-H4. Thus this test schedule resulted in a serum dilution of 0×, 2×, 4×, and 8× for each patient serum. Identical treatment of wells A5-H5 through A8-H8, and A9-H9 through A12-H12 results in 12 sera tested About 60 ml blood was drawn in dry tubes. Within 2 hours of sampling, the blood was centrifuged at 2500 rpm for 10 min. Approximately 30 ml serum were transferred to polypropylene tubes and stored frozen at −20° C. until further use.

Serum was thawed and heat-inactivated at 56° C. for 10 minutes and then aliquoted to prevent repeated cycles of freeze/thawing. Part was used to make five steps of two fold dilutions in medium (DMEM, Gibco BRL) in a quantity enough to fill out approximately 70 96-well plates. Aliquots of undiluted and diluted sera were pipetted in deep well plates (96-well format) and using a programmed platemate dispensed in 100 µl aliquots into 96-well plates. This way the plates were loaded with eight different sera in duplo (100 µl/well) according to the scheme below:

| S1/2 | S1/4 | S1/8 | S1/16 | S1/32 | S5/2 | S5/4 | S5/8 | S5/16 | S5/32 | — | — |
| S1/2 | S1/4 | S1/8 | S1/16 | S1/32 | S5/2 | S5/4 | S5/8 | S5/16 | S5/32 | — | — |
| S2/2 | S2/4 | S2/8 | S2/16 | S2/32 | S6/2 | S6/4 | S6/8 | S6/16 | S6/32 | — | — |
| S2/2 | S2/4 | S2/8 | S2/16 | S2/32 | S6/2 | S6/4 | S6/8 | S6/16 | S6/32 | — | — |
| S3/2 | S3/4 | S3/8 | S3/16 | S3/32 | S7/2 | S7/4 | S7/8 | S7/16 | S7/32 | — | — |
| S3/2 | S3/4 | S3/8 | S3/16 | S3/32 | S7/2 | S7/4 | S7/8 | S7/16 | S7/32 | — | — |
| S4/2 | S4/4 | S3/8 | S3/16 | S3/32 | S8/2 | S8/4 | S8/8 | S8/16 | S8/32 | — | — |
| S4/2 | S4/4 | S3/8 | S3/16 | S3/32 | S8/2 | S8/4 | S8/8 | S8/16 | S8/32 | — | — | per 96-well microtiter plate. From 75 human patient sera tested in total, 25 sera with no apparent toxicity on human 911 cells were subsequently tested for the presence of antibodies capable of neutralizing chimeric adenovirus infection. For this purpose, 96-well microtiter plates were filled with 50 µl DMEM supplemented with 5% fetal calf serum except for wells A1-H1. To wells A1, A2, B1, and B2, 50 µl patient serum 1 was added. Likewise, to wells C1, C2, D1, and D2, 50 µl patient serum 2 was added etc. Subsequently, 50 µl of wells A2-H2 were transferred to wells A3-A4 after which 50 µl of A3-H3 was transferred to A4-H4 etc. until A12-H12 (dilution range: 0- 1/2048). From wells A12-H12, 50 µl was discarded. Next, 50 µl of virus was added after which the microtiter plates were incubated for 1 hour at 37° C. Upon the addition of 50 µl 911 cell-suspension ($3 \times 10^4$ cells/well) plates were incubated for 7-9 days after which neutralizing capacity was scored by the absence, presence, or severity of CPE. As controls during these experiments absence of serum, absence of virus, and absence of serum and virus were taken. Based on these experiments several chimeric viruses are identified towards which little neutralizing antibodies are generated by humans. Similar experiments as described above are performed with wildtype adenovirus serotypes from both human as well as animals to screen for serotypes which are less prone to neutralization due to the host defense system. These experiments although similar are developed in such a way that it allows high throughput screening of many samples at once. This assay is described below.

A High Throughput Assay for the Detection of Neutralizing Activity in Human Serum To enable screening of a large amount of human sera for the presence of neutralizing antibodies against all adenovirus serotypes, an automated 96-wells assay was developed.

Human Sera

A panel of 100 individuals was selected. Volunteers (50% male, 50% female) were healthy individuals between 20 and 60 years old with no restriction for race. All volunteers signed an informed consent form. People professionally involved in adenovirus research were excluded.

Where S1/2 to S8/2 in columns 1 and 6 represent 1× diluted sera and Sx/4, Sx/8, Sx/16 and Sx/32 the twofold serial dilutions. The last plates also contained four wells filled with 100 µl fetal calf serum as a negative control.

Plates were kept at −20° C. until further use.

Preparation of Human Adenovirus Stocks

Prototypes of all known human adenoviruses were inoculated on T25 flasks seeded with PER.C6 cells (Fallaux et al., 1998) and harvested upon full CPE. After freeze/thawing 1-2 ml of the crude lysates were used to inoculate a T80 flask with PER.C6 cells and virus was harvested at full CPE. The time frame between inoculation and occurrence of CPE as well as the amount of virus needed to re-infect a new culture, differed between serotypes. Adenovirus stocks were prepared by freeze/thawing and used to inoculate 3-4 T175 cm$^2$ three-layer flasks with PER.C6 cells. Upon occurrence of CPE, cells were harvested by tapping the flask, pelleted and virus was isolated and purified by a two step CsCl gradient as follows. Cell pellets were dissolved in 50 ml 10 mm NaPO$_4$ buffer (pH 7.2) and frozen at −20° C. After thawing at 37° C., 5.6 ml sodium deoxycholate (5% w/v) was added. The solution was mixed gently and incubated for 5-15 minutes at 37° C. to completely lyse the cells. After homogenizing the solution, 1875 µl 1M MgCl$_2$ was added. After the addition of 375 µl DNase (10 mg/ml) the solution was incubated for 30 minutes at 37° C. Cell debris was removed by centrifugation at 1880×g for 30 minutes at RT without brake. The supernatant was subsequently purified from proteins by extraction with FREON (3×). The cleared supernatant was loaded on a 1M Tris/HCl buffered cesium chloride block gradient (range: 1.2/1.4 gr/ml) and centrifuged at 21000 rpm for 2.5 hours at 10° C. The virus band is isolated after which a second purification using a 1M Tris/HCl buffered continues gradient of 1.33 gr/ml of cesium chloride was performed. The virus was then centrifuged for 17 hours at 55000 rpm at 10° C. The virus band is isolated and sucrose (50% w/v) is added to a final concentration of 1%. Excess CsCl is removed by dialysis (three times 1 hr at RT) in dialysis slides (Slide-a-lizer, cut off 10000 kDa, Pierce, USA) against 1.5 ltr PBS supplemented with CaCl$_2$ (0.9 mm), MgCl$_2$ (0.5 mM) and an increasing concentration of sucrose (1, 2, 5%). After dialysis, the virus is removed from the slide-a-lizer after which it is aliquoted in portions of 25 and 100 µl upon which the virus is stored at −85° C.

To determine the number of virus particles permilliliter, 50 µl of the virus batch is run on a high-pressure liquid chromatograph (HPLC) as described by Shabram et al. (1997). Viruses were eluted using an NaCl gradient ranging from 0 to 600 mm. As depicted in table I, the NaCl concentration by which the viruses were eluted differed significantly among serotypes.

Most human adenoviruses replicated well on PER.C6 cells with a few exceptions. Adenovirus types 8 and 40 were grown on 911 -E4 cells (He et al., 1998). Purified stocks contained between $5 \times 10^{10}$ and $5 \times 10^{12}$ virus particles/ml (VP/ml).

Titration of Purified Human Adenovirus Stocks

Adenoviruses were titrated on PER.C6 cells to determine the amount of virus necessary to obtain full CPE in five days, the length of the neutralization assay. Hereto, 100 µl medium was dispensed into each well of 96-well plates. 25 µl of adenovirus stocks pre-diluted $10^4$, $10^5$, $10^6$ or $10^7$ times were added to column 2 of a 96-well plate and mixed by pipetting up and down 10 times. Then 25 µl was brought from column 2 to column 3 and again mixed. This was repeated until column 11 after which 25 µl from column 11 was discarded. This way serial dilutions in steps of 5 were obtained starting off from a pre-diluted stock. Then $3 \times 10^4$ PER.C6 cells were added in a 100 µl volume and the plates were incubated at 37° C., 5% $CO_2$ for five or six days. CPE was monitored microscopically. The method of Reed and Muensch was used to calculate the cell culture inhibiting dose 50% (CCID50).

In parallel, identical plates were set up that were analyzed using the MTT assay (Promega). In this assay living cells are quantified by colorimetric staining. Hereto, 20 µl MTT (7.5 mgr/ml in PBS) was added to the wells and incubated at 37° C., 5% $CO_2$ for two hours. The supernatant was removed and 100 µl of a 20:1 isopropanol/triton-X100 solution was added to the wells. The plates were put on a 96-wells shaker for 3-5 minutes to solubilize precipitated staining. Absorbance was measured at 540 nm and at 690 nm (background). By this assay wells with proceeding CPE or full CPE can be distinguished.

Neutralization Assay 96-well plates with diluted human serum samples were thawed at 37° C., 5% $CO_2$. Adenovirus stocks diluted to 200 CCID50 per 50 µl were prepared and 50 µl aliquots were added to columns 1-11 of the plates with serum. Plates were incubated for 1 hour at 37° C., 5% $CO_2$. Then 50 µPER.C6 cells at $6 \times 10^5$/ml were dispensed in all wells and incubated for 1 day at 37° C., 5% $CO_2$. Supernatant was removed using fresh pipette tips for each row and 200 µl fresh medium was added to all wells to avoid toxic effects of the serum. Plates were incubated for another 4 days at 37° C., 5% $CO_2$. In addition, parallel control plates were set up in duplo with diluted positive control sera generated in rabbits and specific for each serotype to be tested in rows A and B and with negative control serum (FCS) in rows C and D. Also, in each of the rows E-H a titration was performed as described above with steps of five times dilutions starting with 200 CCID50 of each virus to be tested. On day 5 one of the control plates was analyzed microscopically and with the MTT assay. The experimental titer was calculated from the control titration plate observed microscopically. If CPE was found to be complete, i.e., the first dilution in the control titration experiment analyzed by MTT shows clear cell death, all assay plates were processed. If not, the assay was allowed to proceed for one or more days until full CPE was apparent after which all plates were processed. In most cases the assay was terminated at day 5. A serum sample is regarded to be non-neutralizing when at the highest serum concentration a maximum protection is seen of 40% compared to the controls without serum.

Example 9

Generation of Ad5 Based Viruses With Chimeric Penton Proteins

The method described infra to generate recombinant adenoviruses by co-transfection of two, or more separate cloned adenovirus sequences. These cloned adenoviral sequences were subsequently used to remove specific Ad5 sequences in order to generate template clones which allow for the easy introduction of DNA sequences derived from other adenovirus serotypes. As an example of these template clones, the construction of plasmids enabling swapping of DNA encoding for penton protein is given.

Generation of Adenovirus Template Clones Lacking DNA Encoding for Penton

First a shuttle vector for penton sequences was made by insertion of the 7.2 kb NheI-EcoRV fragrnent from construct pWE/Ad.AflII-EcoRI (described in example 1) into pBr322 digested with the same enzymes. The resulting vector was named pBr/XN. From this plasmid Ad5 penton sequences were deleted and replaced by unique restriction sites that are then used to introduce new penton sequences from other serotypes. Hereto, the left flanking sequences of penton in pBr/XN were PCR amplified using the following primers:

DP5-F:
(SEQ ID NO:71)
5'-CTG TTG CTG CTG CTA ATA GC-3' and

DP5-R:
(SEQ ID NO:72)
5'-CGC GGA TCC TGT ACA ACT AAG GGG AAT ACA AG-3'

DP5-R has an BamHI site (underlined) for ligation to the right flanking sequence and also introduces a unique BsrGI site (bold face) at the 5'-end of the former Ad5 penton region.

The right flanking sequence was amplified using:

DP3-F:
(SEQ ID NO:73)
5'-CGC GGA TCC CTT AAG GCA AGC ATG TCC ATC CTT-3' and

DP3-3R:
(SEQ ID NO:74)
5'-AAA ACA CGT TTT ACG CGT CGA CCT TTC-3'

DP3-F has an BamHI site (underlined) for ligation to the left flanking sequence and also introduces a unique AflII site (bold face) at the 3'-end of the former Ad5 penton region.

The two resulting PCR fragments were digested with BamHI and ligated together. Then this ligation mixture was digested with AvrII and BglII. pBr/XN was also digested with AvrII and BglII and the vector fragment was ligated to the digested ligated PCR fragments. The resulting clone was named pBr/Ad.Δpenton. Penton coding sequences from serotypes other than Ad5 were PCR amplified such that the 5' and 3' ends contained the BsrGI and AflII sites respectively. Introduction of these heterologous penton sequences in pBr/Ad- Δpenton generates constructs named pBr/Ad.pentonXX where XX represents the number of the serotype corresponding to the serotype used to amplify the inserted penton sequences. Subsequently, the new penton sequences were introduced in the pWE/Ad.AflII-rITR construct by exchanging the common FseI fragment. Importantly, in stead of pWE/Ad.AflII-rITR it is also possible to insert the FseI fragment from pBr/Ad.pentonXX into a pWE/Ad.AflII-rITR/HexXX or an pWE/Ad.AflII-rITR/FibXX vector having a modified hexon and/or fiber sequence respectively. In this way the plasmid-based system to generate adenoviruses enables flexible design of any adenovirus with any desired characteristic concerning efficiency and specificity of infection of the target cell as well as immunogenicity.

Amplification of Penton Sequences from Adenovirus Serotypes

To enable amplification of the DNAs encoding penton protein derived from alternative serotypes oligonucleotides were synthesized. Of each adenovirus subgroup the penton sequence of only one member is known to date. Therefore, oligonucleotides were designed based on the known sequences Thus, for amplification of penton sequences from subgroup C oligonucleotides P5-for (5'-gctcgatgtacaatgcg-gcgcgcggcgatgtat-3') (SEQ ID NO:75) and P5-rev (5'-gctc-gacttaagtcaaaaagtgcggctcgatag-3') (SEQ ID NO:76) were used For the amplification of penton sequences from subgroup B oligonucleotides P3-for (5'gctcgatgtacaatgaggagac-gagccgtgcta-3') (SEQ ID NO:77) and P3-rev (5'-gctcgact-taagttagaaaagtgcggcttgaaag-3') (SEQ ID NO:78) were used. For the amplification of penton sequences from subgroup D oligonucleotides P17-for (5'gctcgatgtacaatgaggcgtgcggtg-gtgtcttc-3') (SEQ ID NO:79) and P17-rev (5'-gctcgacttaagt-tagaaggtgcg actggaaagc-3') (SEQ ID NO:81) were used. For the amplification of penton sequences from subgroup F oligonucleotides PF-for (5'-gctcgatgtacaatgagacgtgcggtgg-gagtg-3') (SEQ ID NO:82) and PF-rev (5'-gctcga cttaagt-taaaacgtgcggctagacag-3') (SEQ ID NO:83) were used. All above described forward oligonucleotides contain a BsrGI restriction site at their 5'-end and all reverse oligonucleotides contain an AflII restriction site at the 5'-end.

The amplification reaction (50 µl) contained 2 mm dNTPs, 25 pmol of each oligonucleotide, standard 1× PCR buffer, 1.5 mm $MgCl_2$, and 1 Unit Pwo heat stable polymerase (Boehringer) per reaction. The cycler program contained 20 cycles, each consisting of 30 sec. 94° C., 60 sec. 60-64° C., and 120 sec. At 72° C. One-tenth of the PCR product was run on an agarose gel which demonstrated that a DNA fragment was amplified. Of each different template, two independent PCR reactions were performed after which the independent PCR fragments obtained are sequenced to determine the nucleotide sequence. Of the 51 human serotypes 20 penton sequences have been amplified.

Generation of Penton Chimeric Adenoviral DNA Constructs

All amplified penton DNAs as well as the vector (pBr/Ad.Δpenton) were digested with BsrGI and AflII. The digested DNAs was subsequently run on a agarose gel after which the fragments were isolated from the gel and purified using the Geneclean kit (Bio101 Inc). The PCR fragments were then cloned into the BsrGI and AflII sites of pBr/Ad-.Δpenton, thus generating pBr/Ad.pentonXX (where XX stands for the serotype number of which the penton DNA was isolated). So far the penton sequence of serotypes 2, 3, 5, 6, 7, 11, 21, 26, 35, 39, 40, 41, 42, 47, 48, 49 and 51 have been cloned into pBr/Ad.pentonXX . From pBr/Ad.pentonXX an 5.1 kb FseI fragment encompassing the penton sequence was isolated via gel electrophoresis and Geneclean. This FseI fragment was subsequently cloned in cosmid pWE/Ad.AflII-rITR (see, Example 1) which was digested to completion with FseI and dephosphorylated as described previously. This cosmid cloning resulted in the formation of construct pWE/Ad.AflII-rITR/PentonXX (where XX stands for the serotype number of which the penton DNA was isolated).

Generation of Recombinant Adenovirus Chimaeric for Penton Protein

To generate recombinant Ad 5 virus carrying the Penton of alternative serotypes two constructs, pCLIP.Luc and pWE/Ad.AflII-rITR/PenXX were transfected into adenovirus producer cells.

For transfection, 4 µg of pCLIP.Luc and 4 µg of pWE/Ad.AflII-rITR/PentonXX) were diluted in serum free DMEM to 100 µl total volume. To this DNA suspension 100 µl 1× diluted lipofectamine (Gibco) was added. After 30 minutes at room temperature the DNA-lipofectamine complex solution was added to 2.5 ml of serum-free DMEM which was subsequently added to a T25 cm tissue culture flask. This flask contained $2×10^6$ PER.C6 cells that were seeded 24-hours prior to transfection. Two hours later, the DNA-lipofectamine complex containing medium was diluted once by the addition of 2.5 ml DMEM supplemented with 20% fetal calf serum. Again 24 hours later the medium was replaced by fresh DMEM supplemented with 10% fetal calf serum. Cells were cultured for 6-8 days, subsequently harvested, and freeze/thawed 3 times. Cellular debris was removed by centrifugation for 5 minutes at 3000 rpm room temperature. Of the supernatant (12.5 ml) 3-5 ml was used to infect again infect PER.C6 cells (T80 $cm^2$ tissue culture flasks). This re-infection results in full CPE after 5-6 days after which the adenovirus is harvested as described above.

The described Examples 1-9 encompass the construction of recombinant adenoviral vectors, chimaeric for either fiber protein or hexon protein which results in an altered infection host range or altered immune response towards adenoviral vectors. These chimaeric adenoviral vectors are generated for the purpose of gene transfer and recombinant DNA vaccines. It must be stressed that in a manner analogous as described under Examples 1-9, chimeric adenoviral vectors are constructed for penton and can be constructed for all other adenovirus proteins including but not limited to DNA encoding for small proteins required for adenovirus assembly and sequences required for adenovirus replication. Moreover, it must be emphasized that with this technology double, triple, quadruple, etc. chimeric adenoviral vectors can be constructed with the aim to combine parts of existing adenovirus serotypes to generate adenoviral vectors with preferred characteristics for any given target cell or target disease.

Legends to Tables

Table 1: Summary of the classification of known human adenovirus serotypes based upon the principle of hemagglutination.

Table 2: Association of human adenovirus serotypes with human disease.

Table 3: Oligonucleotides and degenerate oligonucleotides used for the amplification of DNA encoding for fiber protein derived from alternative human adenovirus serotypes. Bold letters in oligonucleotides A-E represent an NdeI restriction site. Bold letters in oligonucleotides 1-6 and 8 represent an NsiI restriction site. Bold letters in oligonucleotide 7 represent a PacI restriction site.

Table 4: Production results of fiber chimeric adenoviruses. The number of virus particles per ml were determined using HPLC. The number of infectious units (IU) per milliliter were determined through titration on human 911 cells. For infection experiments, the number of virus particles per milliliter is taken from all chimeric adenoviruses since IU/ ml reflects a receptor mediated process.

Table 5: Transduction results of human cell lines and primary cells. A549: Human lung carcinoma cell line (ATCC, CCL-1185). K562: Human erythroid leukemia (ATCC, CCL-243). SupT1: Human Lymphoblast hybrid B and T (ATCC, CRL-1991). GM09503: Human primary fibroblasts. HEPG2: Human liver carcinoma (ATCC, HB8065). CEM: human lymphoblast cells (ATCC, CRL-1992). HeLa: Human cervix carcinoma (ATCC, CCL-2). Primary amniocytes and chorionvilli cells were obtained from department of antropogenetics, Leiden, NL. Primary Smooth muscle cells and synoviocytes were obtained from TNO-PG, Leiden, The Netherlands. Shown are the luciferase activity (in relative light units (RLU) per μg protein) measurements of cells infected at MOI 5000 virus particles per cell.

Table 6: Expression of integrins $\alpha_v\beta3$ and $\alpha_v\beta5$, the Coxsackie adenovirus receptor (CAR), and MHC class I on the membranes of target cells. In addition to the cells described in table 5: HUVEC: human umbilical vein endothelial cells were obtained from TNO-PG, Leiden, The Netherlands. Shown is the percentage of cells expressing either molecule on their membrane. The Ad5 based vector carrying a fiber of one representative of each subgroup and the efficiency of infection is shown on the right of the table. ND: not determined. 0% means undetectable expression of the molecule on the membrane of the cell using flow cytometry. 100% means high expression of the molecule on the cell membrane.

REFERENCES

Arnberg N., Mei Y. and Wadell G., 1997. Fiber genes of adenoviruses with tropism for the eye and the genital tract. *Virology* 227: 239-244.

Bout A., 1997. Gene therapy, p. 167-182. In: D. J. A. Crommelin and R. D. Sindelar (ed.), *Pharmaceutical Biotechnology*, Harwood Academic Publishers.

Bout, A. 1996. Prospects for human hene therapy. *Eur. J. Drug Met. And Pharma.* 2, 175-179.

Blaese et al., *Cancer Gene Ther.*, 2 (1995):291-297).

Brody and Crystal, *Ann. N.Y. Acad. Sci.* 716(1994):90-101.

Chroboczek J., Ruigrok R. W. H., and Cusack S., 1995. Adenovirus fiber, p. 163-200. In: W. Doerfler and P. Bohm (ed.), *The molecular repertoire of adenoviruses, I.* Springer-Verlag, Berlin.

Defer C., Belin M., Caillet-Boudin M. and Boulanger P., 1990. Human adenovirus-host cell interactions; comparative study with members of subgroup B and C. *Journal of Virology* 64 (8): 3661-3673.

De Jong, J. C., Wermenbol, A. G., Verweij-Uijterwaal, M. W., Slaterus, K. W., Wertheim-van Dillen, P., van Doornum, G. J. J., Khoo, S. H., and Hierholzer, J. C. (1998) Adenoviruses from HIV-infected patients, including two new candidate serotypes Ad50 and Ad51 of Subgenus D and B1 respectively. In preparation.

Eisenlohr, L. C., Gerard, W., and Hackett, C. J. (1987). Role of receptor-binding activity of the viral hemagglutin molecule in the presentation of influenza virus antigens to helper T-cells. *Journal of Virology* 61, 1375-1383

Eiz B and Pring-Okerblom P., 1997. Molecular characterization of the type-specific g-determinant located on the adenovirus fiber. *Journal of Virology* 71: 6576-6581.

Francki, R. I. B., Fauquet, C. M., Knudson, D. L. and Brown, F. (1991) Classification and nomenclature of viruses. Fifth report of the international Committee on taxonomy of viruses. *Arch. Virol. Suppl.* 2, 140-144

GahÈry-SÈgard H., Farace F., Godfrin D., Gaston J., Lengagne R., Tursz T., Boulanger P. and Guillet J., 1998. Immune response to recombinant capsid proteins of adenovirus in humans: antifiber and anti-penton base antibodies have a synergistic effect on neutralizing activity. *Journal of Virology* 72: 2388-2397.

Gall J., Kass-Eisler A., Leinwand L. and Falck-Pedersen E., 1996. Adenovirus type 5 and 7 capsid chimera: fiber replacement alters receptor tropism without affecting primary immune neutralization epitopes. *Journal of Virology* 70 (4): 2116-2123.

Greber, U. F., Willets, M., Webster, P., and Helenius, A. (1993). Stepwise dismanteling of adenovirus 2 during entry into cells. *Cell* 75, 477-486.

Hynes, R. O. (1992) Integrins: versatility, modulation and signalling in cell adhesion. *Cell* 69, 11-25

Herz and Gerard, *Proc. Natl. Acad. Sci. (USA)*, 96 (1993): 2812-2816

Hierholzer, J. C. (1992) Adenovirus in the immunocompromised host. *Clin. Microbiol Rev.* 5, 262-274.

Hierholzer, J. C., Wigand, R., Anderson, L. J., Adrian, T., and Gold, J. W. M. (1988) Adenoviruses from patients with AIDS: a plethora of serotypes and a description of five new serotypes of subgenus D (types43-47). *J. Infect. Dis.* 158, 804-813.

Ishibashi, M. and Yasue (1983) in *Adenoviruses of Animals*, Chapter 12, p497-561

Kay, R., Takei, F., and Humphries, R. K. (1990). Expression- cloning of a cDNA encoding M1/69-J11d heat-stable antigens. *J. Immunol.* 145 (6), 1952-1959

Khoo, S. H., Bailey, A. S., De Jong, J. C., and Mandal, B. K. (1995). Adenovirus infections in human immunodeficiency virus-positive patients: Clinical features and molecular epidemiology. *J. Infect. Dis* 172, 629-637

Kidd, A. H., Chrboczek, J., Cusack, S., and Ruigrok, R. W.IH. (1993) Adenovirus type 40 virions containtwo distinct fibers. *Virology* 192, 73-84.

Krasnykh V. N., Mikheeva G. V., Douglas J. T. and Curiel D. T., 1996. Generation of recombinant adenovirus vectors with modified fibers for altering viral tropism. *Journal of Virology* 70(10): 6839-6846.

Krasnykh V., Dmitriev I., Mikheeva G., Miller C. R., Belousova N. and Curiel D. T.,1998. Characterization of an adenovirus vector containing a heterologous peptide epitope in the HI loop of the fiber knob. *Journal of Virology* 72(3): 1844-1852.

Leopold, P. L., Ferris, B., Grinberg, I., Worgall, S., Hackett, N. R., and Crystal, R. G. (1998). Fluorescent virions: Dynamic tracking of the pathway of adenoviral vectors in living cells. *Hum. Gene Ther.* 9, 367-378.

Levrero, M., Barban, V., Manteca, S., Ballay, A., Balsamo, C., Avantaggiata, M. L., Natoli, G., Skellekens, H., Tiollais, P., and Perricaudet, M. (1991 (.Defective and non-defective adenovirus vectors for expression foreign genes in vitro and in vivo. *Gene* 101, 195-202.

Matlin, K. S., Reggio, H., Helenius, A., and Simons, K. (1981). Infectious entry pathway of influenza virus in a canine kidney cell line. *J. Cell Biol.* 91, 601-613

Morgan, C., Rozenkrantz, H. S., and Mednis, B. (1969 (Structure and development of viruses as observed in the electron microscope.X. Entry and uncoating of adenovirus. *J. Virol* 4, 777-796.

Roest, P. A. M., Bout, M., van der Tuijn, A. C., Ginjaar, I. B., Bakker, E., Hogervorst, F. B. L., van Ommen, G-J. B., den Dunnen, J. T. (1996). *J. Med. Genet.* 33, 935-939.

Roest P. A. M., van der Tuijn, A. C., Ginjaar, I. B., Hoeben, R. C., Hogervorst, F. B. L., Bakker, E, den Dunnen, J. T. van Ommen, G-J. B. (1996). *Neuromusc. Disord.* 6 (no. 3), 195-202.

Roest P. A. M., van der Tuijn, A. C., Ginjaar, I. B., Hoeben, R. C., Hogervorst, F. B. L., Bakker, E, den Dunnen, J. T.van Ommen, G-J. B. (1999). *Lancet* 353, 727-728.

Richman, D. D., Hostetler, K. Y., Yazaki, P. J., and Clark, S. (1986). Fate of influenza A virion proteins after entry into subcellular fractions of LLC cells and the effect of amantadine. *Virology* 151, 200-210

Stevenson S. C., Rollence M., White B., Weaver L. and McClelland A., 1995. Human adenovirus serotypes 3 and 5 bind to two different cellular receptors via the fiber head domain. *Journal of Virology* 69(5): 2850-2857.

Stevenson S. C., Rollence M., Marshall-Neff J. and McClelland A., 1997. Selective targeting of human cells by a chimaeric adenovirus vector containing a modified fiber protein. *Journal of Virology* 71(6): 4782-4790.

Signas, G., Akusjarvi, G., and Petterson, U. (1985). Adenovirus 3 fiberpolypeptide gene: Complications for the structure of the fiber protein. *Journal of Virology*. 53, 672-678.

Stouten, P. W. F., Sander, C., Ruigrok, R. W. H., and Cusack, S. (1992) New triple helical model for the shaft of the adenovirus fiber. *J. Mol. Biol.* 226, 1073-1084.

Schulick, A. H., Vassalli, G., Dunn, P. F., Dong, G., Rade, J. J., Zamarron, C. and Dichek, D. A. (1997). Established immunity precludes adenovirus-mediated gene transfer in rat carotid arteries.

Schnurr, D and Dondero, M. E. (1993) Two new candidate adenovirus serotypes *Intervirol.* 36, 79-83

Svensson, V. and Persson, R. (1984). Entry of adenovirus 2 into Hela cells. *Journal of Virology.* 51, 687-694.

Varga, M. J., Weibull, C., and Everitt, E. (1991). Infectious entry pathway of adenovirus type 2. *Journal of Virology* 65, 6061-6070.

Wickham T. J., Carrion M. E. and Kovesdi I., 1995. Targeting of adenovirus penton base to new receptors through replacement of its RGD motif with other receptor-specific peptide motifs. *Gene Therapy* 2: 750-756.

Wickham T. J., Segal, D. M., Roelvink, P. W., Carrion M. E., Lizonova, A., Lee, G-M., and Kovesdi, I. (1996). Targeted adenovirus gene transfer to endothelial and smooth muscle cells by using bispecific antibodies. *Journal of Virology.* 70 (10), 6831-6838

Wickham, T. J., Mathias, P., Cherish, D. A., and Nemerow, G. R. (1993) Integrins avb3 and avb5 promote adenovirus internalisation but not virus attachment. *Cell* 73, 309-319

TABLE 1

| Subgroup | serotypes | hemagglutination rhesus | hemagglutination rat |
|---|---|---|---|
| A | 12, 18, 31 | − | +/− |
| B | 3, 7, 11, 14, 16, 21, 34, 35, 51 | + | − |
| C | 1, 2, 5, 6 | − | +/−c |
| D | 8-10, 13, 15, 17, 19, 20, 22-30, 32, 33, 36-39, 42-47, 49, 50 | +/− | + |
| E | 4 | − | +/− |
| F | 40, 41 | − | +/− |

TABLE 2

| Syndrom | Subgenus | Serotype |
|---|---|---|
| Respiratory illness | A | 31 |
| | B | 3, 7, 11, 14, 21, 34, 35, 51 |
| | C | 1, 2, 5, 6 |
| | D | 39, 42-48 |
| | E | 4 |
| Keratoconjunctivitis (eye) | B | 11 |
| | D | 8, 19, 37, 50 |
| Hemorrhagic cystitis (Kidney) | B | 7, 11, 14, 16, 21, 34, 35 |
| And urogenital tract infections | C | 5 |
| | D | 39, 42-48 |
| Sexual transmission | C | 2 |
| | D | 19, 37 |
| Gastroenteritis | A | 31 |
| | B | 3 |
| | C | 1, 2, 5 |
| | D | 28 |
| | F | 40, 41 |
| CNS disease | A | 12, 31 |
| | B | 3, 7 |
| | C | 2, 5, 6 |
| | D | 32, 49 |
| Hepatitis | A | 31 |
| | C | 1, 2, 5 |
| Disseminated | A | 31 |
| | B | 3, 7, 11, 21 |
| | D | 30, 43-47 |
| None (???) | A | 18 |
| | D | 9, 10, 13, 15, 17, 20, 22-29, 33, 36, 38 |

TABLE 3

| Serotype | Tail oligonucleotide | Knob oligonucleotide |
|---|---|---|
| 4 | A | 1 |
| 8 | B | 2 |
| 9 | B | 2 |
| 12 | E | 3 |
| 16 | C | 4 |
| 19p | B | 2 |
| 28 | B | 2 |
| 32 | B | 2 |
| 36 | B | 2 |
| 37 | B | 2 |
| 40-1 | D | 5 |
| 40-2 | D | 6 |

TABLE 3-continued

| Serotype | Tail oligonucleotide | Knob oligonucleotide |
|---|---|---|
| 41-s | D | 5 |
| 41-1 | D | 7 |
| 49 | B | 2 |
| 50 | B | 2 |
| 51 | C | 8 |

A: 5'-CCC GTG TAT CCA TAT GAT GCA GAC AAC GAC CGA CC-3' (SEQ ID NO:1)

B: 5'-CCC GTC TAC CCA TAT GGC TAC GCG CGG-3' (SEQ ID NO:2)

C: 5'-CCK GTS TAC CCA TAT GAA GAT GAA AGC-3' (SEQ ID NO:3)

D: 5'-CCC GTC TAC CCA TAT GAC ACC TYC TCA ACT C-3' (SEQ ID NO:4)

E: 5'-CCC GTT TAC CCA TAT GAC CCA TTT GAC ACA TCA GAC-3' (SEQ ID NO:5)

1: 5'-CCG ATG CAT TTA TTG TTG GGC TAT ATA GGA-3' (SEQ ID NO:6)

2: 5'-CCG ATG CAT TYA TTC TTG GGC RAT ATA GGA-3' (SEQ ID NO:7)

3: 5'-CCG ATG CAT TTA TTC TTG GGR AAT GTA WGA AAA GGA-3' (SEQ ID NO:8)

4: 5'-CCG ATG CAT TCA GTC ATC TTC TCT GAT ATA-3' (SEQ ID NO:9)

5: 5'-CCG ATG CAT TTA TTG TTC AGT TAT GTA GCA-3' (SEQ ID NO:10)

6: 5'-GCC ATG CAT TTA TTG TTC TGT TAC ATA AGA-3' (SEQ ID NO:11)

7: 5'-CCG TTA ATT AAG CCC TTA TTG TTC TGT TAC ATA AGA A-3' (SEQ ID NO:12)

8: 5'-CCG ATG CAT TCA GTC ATC YTC TWT AAT ATA-3' (SEQ ID NO:13)

TABLE 4

| Adenovirus | Virus particles/ml | Infectious units/ml |
|---|---|---|
| Ad5Fib5 | $2.2 \times 10^{12}$ | $6.8 \times 10^{11}$ |
| Ad5Fib12 | $4.4 \times 10^{12}$ | $1.9 \times 10^{12}$ |
| Ad5Fib16 | $1.4 \times 10^{12}$ | $3.0 \times 10^{10}$ |
| Ad5Fib17 | $9.3 \times 10^{11}$ | $9.5 \times 10^{9}$ |
| Ad5Fib28 | $5.4 \times 10^{10}$ | $2.8 \times 10^{8}$ |
| Ad5Fib32 | $2.0 \times 10^{12}$ | $1.1 \times 10^{12}$ |
| Ad5Fib40-S | $3.2 \times 10^{10}$ | $1.0 \times 10^{10}$ |
| Ad5Fib40-L | $2.0 \times 10^{12}$ | $6.4 \times 10^{11}$ |
| Ad5Fib49 | $1.2 \times 10^{12}$ | $4.3 \times 10^{11}$ |
| Ad5Fib51 | $5.1 \times 10^{12}$ | $1.0 \times 10^{12}$ |

TABLE 5

| | Celline | | | | | | | | |
|---|---|---|---|---|---|---|---|---|---|
| | Ad5Fiber5 | Ad5Fiber12 | Ad5Fiber16 | Ad5Fiber28 | Ad5Fiber32 | Ad5Fiber40-S | Ad5Fiber40-L | Ad5Fiber49 | Ad5Fiber51 |
| A549 | 54186 | 2 | 283339 | 3556 | 46635 | 84562 | 407130 | 2 | 18337 |
| K562 | 1 | 5 | 109688 | 7915 | 30958 | 1086 | 1907 | 1524 | 172569 |
| SupT1 | 3926082 | 606032 | 14553005 | 855043 | 80834 | ND | 686546 | 77 | 1266653 |
| GM09503 | 506 | 4 | 117094 | 1858 | 39652 | 52759 | 609 | 4 | 106309 |
| 1⁰ chorion-villi | 75 | 147 | 1026757 | 203114 | 9756 | ND | 1688026 | 49 | 1512035 |
| 1⁰ Amnion-villi | 8420131 | 4975463 | 6991792 | 37512 | 3313879 | ND | 5250524 | 4081 | 5785404 |
| HEPG2 | 108612409 | 11428921 | 19315715 | 962463 | 3844661 | ND | 90713451 | 23894 | 8003123 |
| HeLa | 6838148 | 510784 | 776984 | 13571 | 15600 | 1551397 | 1694919 | 103 | 163415 |
| CEM | 93 | 6 | 1600 | 0 | 69 | 9 | 18 | 6.5 | 53 |
| Synoviocytes | 103 | ND | 9936417 | ND | ND | ND | ND | ND | ND |
| Smooth muscle cells | 19019 | 664 | 816381 | 621 | ND | ND | 38632 | ND | ND |

TABLE 6

| | | | | | subgroup A | Subgroup B | Subgroup C | Subgroup D | Subgroup F |
|---|---|---|---|---|---|---|---|---|---|
| | | | | | | Celline | | | |
| | a,b3 | a,b5 | CAR | MHC class I | Ad5Fiber12 | Ad5Fiber16 | Ad5Fiber5 | Ad5Fiber 32 | Ad5Fiber40-L |
| A549 | 17% | 98% | 100% | ND | Low | High | High | High | High |
| K562 | 12% | 55% | 0% | 15% | Low | High | Low | High | High |
| GM09503 | 20% | 50% | 0% | 100% | Low | High | Low | High | Low |
| CEM | 0% | 0% | 3% | 100% | Low | High | Low | Low | Low |
| SupT1 | 5% | 1% | 70% | 100% | High | High | High | High | High |

TABLE 6-continued

| | | | | | subgroup A | Subgroup B Celline | Subgroup C | Subgroup D | Subgroup F |
|---|---|---|---|---|---|---|---|---|---|
| | $a_vb3$ | $a_vb5$ | CAR | MHC class I | Ad5Fiber12 | Ad5Fiber16 | Ad5Fiber5 | Ad5Fiber 32 | Ad5Fiber40-L |
| Smooth muscle cells | 100% | 70% | 0% | 15% | Low | High | Low | ND | Low |
| HUVEC | 100% | 15% | 10% | 90% | ND | High | Low | ND | ND |
| Synoviocytes | 30% | 40% | 0% | 100% | ND | High | Low | ND | ND |
| 1° chorionvilli | 100% | 0% | 12% | 100% | Low | High | Low | Low | High |
| HepG2 | 0% | 10% | 100% | 80% | High | High | High | High | High |

What is claimed is:

1. A recombinant chimaeric adenovirus of serotype 5 with an altered tropism as compared to wild-type adenovirus serotype 5, said recombinant adenovirus comprising:
   a fiber protein comprising the knob domain of a fiber protein from an adenoviral serotype selected from the group consisting of: adenovirus serotype 32, 49, and 51.

2. The recombinant chimaeric adenovirus of claim 1, wherein said adenovirus further comprises:
   at least a part of a penton or a hexon protein, or both, from a third adenovirus serotype; and
   wherein said third adenovirus serotype may be the same as or different from the serotype of the knob domain.

3. An isolated vector encoding a recombinant chimaeric adenovirus of serotype 5 with an altered tropism as compared to a wild type adenovirus serotype 5, said isolated vector comprising: at least one ITR, a packaging signal, a nucleotide sequence of interest, and a nucleic acid encoding a fiber protein, said nucleic acid comprising: a nucleic acid sequence encoding at least the knob domain of a fiber protein from an adenoviral serotype selected from the group consisting of adenovirus serotype 32, 49, and 51.

4. The isolated vector of claim 3, wherein the isolated vector is a plasmid.

5. The isolated vector of claim 3, wherein said nucleic acid encoding a fiber protein further comprises a nucleotide sequence encoding a part of the tail of the fiber protein of adenovirus serotype 5.

* * * * *

UNITED STATES PATENT AND TRADEMARK OFFICE
CERTIFICATE OF CORRECTION

| | |
|---|---|
| PATENT NO. | : 7,749,493 B2 |
| APPLICATION NO. | : 11/207626 |
| DATED | : July 6, 2010 |
| INVENTOR(S) | : Menzo Havenga, Ronald Vogels and Abraham Bout |

It is certified that error appears in the above-identified patent and that said Letters Patent is hereby corrected as shown below:

On the title page:
In ITEM (56) References Cited OTHER PUBLICATIONS

| | | | |
|---|---|---|---|
| Page 2 | 2$^{nd}$ COLUMN | 20$^{th}$ entry | change "inactivatedadenovirus" to --inactivated adenovirus-- |
| Page 3 | 1$^{st}$ COLUMN | 2$^{nd}$ entry | change "SerotypeSpecific" to --Serotype Specific-- |
| Page 3 | 1$^{st}$ COLUMN | 6$^{th}$ entry | change "transferringpolylysine-mediated" to --transferring polylysine-mediated-- |
| Page 3 | 1st COLUMN | 8$^{th}$ entry | change "VirusInfected" to --Virus Infected-- |
| Page 3 | 2$^{nd}$ COLUMN | 11$^{th}$ entry | change "FiberProtein" to --Fiber Protein-- |
| Page 3 | 2$^{nd}$ COLUMN | 19$^{th}$ entry | change "adenovirusmediated" to --adenovirus mediated-- |
| Page 3 | 2$^{nd}$ COLUMN | 21$^{st}$ entry | change "Typespecific" to --Type-specific-- |
| Page 4 | 1$^{st}$ COLUMN | 2$^{nd}$ entry | change "Adenovirus1 1," to --Adenovirus 11,-- |
| Page 4 | 1$^{st}$ COLUMN | 9$^{th}$ entry | change "internet<URL:htpp://" to --Internet, URL:http://-- |
| Page 4 | 1$^{st}$ COLUMN | 9$^{th}$ entry | change "www. mw.com/cgi-bin/dictionary," to --www.m-w.com/cgi-bin/dictionary,-- |
| Page 4 | 1$^{st}$ COLUMN | 11$^{th}$ entry | change "Conjugatemediated" to --Conjugate mediated-- |
| Page 4 | 1$^{st}$ COLUMN | 18$^{th}$ entry | change "BaculovirusExpressed" to --Baculovirus Expressed-- |
| Page 4 | 1$^{st}$ COLUMN | 23$^{rd}$ entry | change "pages, XP00266251" to --XP00266251-- |
| Page 4 | 2$^{nd}$ COLUMN | 6$^{th}$ entry | change "antbody" to --antibody-- |
| Page 4 | 2$^{nd}$ COLUMN | 15$^{th}$ entry | change "Differen" to --Different-- |
| Page 4 | 2$^{nd}$ COLUMN | 23$^{rd}$ entry | change "transferringpolylysine/" to --transferring polylysine/-- |
| Page 5 | 1$^{st}$ COLUMN | 3$^{rd}$ entry | change "pages, abstract only," to --abstract only,-- |

Signed and Sealed this
Twenty-fifth Day of January, 2011

David J. Kappos
*Director of the United States Patent and Trademark Office*

CERTIFICATE OF CORRECTION (continued)
U.S. Pat. No. 7,749,493 B2

In the specification:

| | | |
|---|---|---|
| COLUMN 16 | LINE 26 | change "(Gibco," to --(GIBCO®,-- |
| COLUMN 19 | LINE 58 | change "(Gibco)" to --(GIBCO®)-- |
| COLUMN 20 | LINE 47 | change "FREON." to --FREON®.-- |
| COLUMN 26 | LINE 47 | change "(Gibco)" to --(GIBCO®)-- |
| COLUMN 28 | LINE 8 | change "Gibco" to --GIBCO®-- |
| COLUMN 28 | LINE 56 | change "FREON" to --FREON®-- |
| COLUMN 28 | LINE 65 | change "(Slide-a-lizer," to --(Slide-a-lyzer®,-- |
| COLUMN 31 | LINE 27 | change "used" to --used.-- |
| COLUMN 31 | LINE 60 | change "Geneclean" to --GENECLEAN®-- |
| COLUMN 32 | LINE 1 | change "Geneclean." to --GENECLEAN®.-- |
| COLUMN 32 | LINE 18 | change "(Gibco)" to --(GIBCO®)-- |